United States Patent
Lee et al.

(10) Patent No.: US 12,209,093 B2
(45) Date of Patent: Jan. 28, 2025

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hyo-Jung Lee, Gyeonggi-do (KR); Young-Kwang Kim, Gyeonggi-do (KR); Jin-Ri Hong, Gyeonggi-do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 949 days.

(21) Appl. No.: 17/175,142

(22) Filed: Feb. 12, 2021

(65) Prior Publication Data

US 2021/0261560 A1     Aug. 26, 2021

(30) Foreign Application Priority Data

Feb. 17, 2020 (KR) .................. 10-2020-0018865

(51) Int. Cl.
| | | |
|---|---|---|
| *C07D 491/052* | (2006.01) | |
| *C07D 493/04* | (2006.01) | |
| *C07D 495/04* | (2006.01) | |
| *C07D 519/00* | (2006.01) | |
| *H10K 50/15* | (2023.01) | |
| *H10K 50/16* | (2023.01) | |
| *H10K 50/17* | (2023.01) | |
| *H10K 50/18* | (2023.01) | |
| *H10K 85/30* | (2023.01) | |
| *H10K 85/60* | (2023.01) | |

(52) U.S. Cl.
CPC ....... *C07D 491/052* (2013.01); *C07D 493/04* (2013.01); *C07D 495/04* (2013.01); *C07D 519/00* (2013.01); *H10K 85/342* (2023.02); *H10K 85/615* (2023.02); *H10K 85/633* (2023.02); *H10K 85/636* (2023.02); *H10K 85/654* (2023.02); *H10K 85/6574* (2023.02); *H10K 85/6576* (2023.02); *H10K 50/15* (2023.02); *H10K 50/16* (2023.02); *H10K 50/171* (2023.02); *H10K 50/18* (2023.02)

(58) Field of Classification Search
CPC .................... C07D 491/048; C07D 513/02
See application file for complete search history.

(56) References Cited

U.S. PATENT DOCUMENTS

| | | | | |
|---|---|---|---|---|
| 2018/0022991 A1* | 1/2018 | Kang | ........... | H10K 85/654 252/301.16 |
| 2020/0207713 A1* | 7/2020 | Lee | ........... | C07D 209/80 |
| 2021/0261560 A1* | 8/2021 | Lee | ........... | H10K 85/342 |
| 2022/0045281 A1* | 2/2022 | Hong | ........... | C07D 403/10 |
| 2022/0059777 A1* | 2/2022 | Lee | ........... | C07D 491/06 |
| 2022/0089610 A1* | 3/2022 | Mo | ........... | H10K 85/6572 |
| 2023/0126428 A1* | 4/2023 | Kim | ........... | C07D 209/80 257/40 |
| 2023/0141435 A1* | 5/2023 | Jung | ........... | H10K 85/633 257/40 |

FOREIGN PATENT DOCUMENTS

| | | | | |
|---|---|---|---|---|
| CN | 106866498 A | | 6/2017 | |
| KR | 20220060358 A | * | 5/2022 | ........... C07D 491/06 |

OTHER PUBLICATIONS

Machine Translation of KR 20220060358, 2024 (Year: 2024).*

* cited by examiner

*Primary Examiner* — Liam J Heincer
(74) *Attorney, Agent, or Firm* — G. Creston Campbell

(57) ABSTRACT

The present disclosure relates to an organic electroluminescent compound and an organic electroluminescent device comprising the same. By comprising the organic electroluminescent compound according to the present disclosure, an organic electroluminescent device having low driving voltage and/or high luminous efficiency can be provided.

6 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and organic electroluminescent device comprising the same.

BACKGROUND ART

The TPD/Alq$_3$ bilayer small molecule organic electroluminescent device (OLED) with green-emission, which is constituted with a light-emitting layer and a charge transport layer, was first developed by Tang, et al., of Eastman Kodak in 1987. Thereafter, the studies on an OLED have been rapidly commercialized.

The most important factor determining luminous efficiency in an OLED is light-emitting materials. Until now, fluorescent materials have been widely used as light-emitting materials. However, in view of electroluminescent mechanisms, since phosphorescent light-emitting materials theoretically enhance luminous efficiency by four (4) times compared to fluorescent light-emitting materials, phosphorescent light-emitting materials have been widely researched. Until now, Iridium(III) complexes have been widely known as phosphorescent light-emitting materials, including bis(2-(2-benzothienyl)-pyridinato-N,C-3')iridium (acetylacetonate) [(acac)Ir(btp)$_2$], tris(2-phenylpyridine) iridium [Ir(ppy)$_3$] and bis(4,6-difluorophenylpyridinato-N, C2)picolinato iridium (Firpic) as red-, green-, and blue-emitting materials, respectively.

In the prior art, 4,4'-N,N'-dicarbazol-biphenyl (CBP) is the most widely known phosphorescent host material. Recently, Pioneer (Japan) et al., developed a high performance OLED using bathocuproine (BCP) and aluminum (III)bis(2-methyl-8-quinolinate)(4-phenylphenolate) (BAlq), etc., as host materials, which were known as hole blocking materials.

However, although the conventional materials provide good luminous characteristics, they have the following disadvantages: (1) Due to their low glass transition temperature and poor thermal stability, their degradation may occur during a high-temperature deposition process in a vacuum, and the lifespan of the device may be shortened. (2) The power efficiency of the OLED is given by [(π/voltage)× current efficiency], and the power efficiency is inversely proportional to the voltage. Although the OLED comprising phosphorescent host materials provides higher current efficiency (cd/A) than one comprising fluorescent materials, a significantly high driving voltage is necessary. Thus, there is no merit in terms of power efficiency (lm/W). (3) Also, the operational lifespan of the OLED is short, and it is still necessary to improve luminous efficiency.

In order to improve luminous efficiency, operating voltage and/or lifetime, various materials or concepts for an organic layer of an OLED have been proposed, but they have not been satisfactory in practical use.

DISCLOSURE OF INVENTION

Technical Problem

The object of the present disclosure is firstly, to provide an organic electroluminescent compound which is effective to produce an organic electroluminescent device having low driving voltage and/or high luminous efficiency, and secondly, to provide an organic electroluminescent device comprising the organic electroluminescent compound.

Solution to Problem

As a result of intensive studies to solve the technical problem above, the present inventors found that the aforementioned objective can be achieved by an organic electroluminescent compound represented by the following formula 1, so that the present invention was completed.

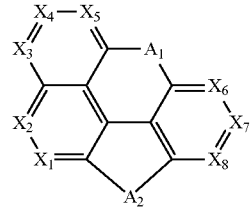

(1)

In formula 1,

A$_1$ and A$_2$ each independently represent, N-L$_1$-Ar$_1$, O, or S;

X$_1$ to X$_8$ each independently represent, N or CR$_1$;

L$_1$ represents a single bond, a substituted or unsubstituted (C6-C30)arylene, or a substituted or unsubstituted (3- to 30-membered)heteroarylene;

Ar$_1$ and R$_1$ each independently represent, hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and an (C6-C30) aromatic ring, or -L$_a$-N—(Ar$_a$)(Ar$_b$); or may be linked to the adjacent substituent to form a ring(s);

L$_a$ represents a single bond, a substituted or unsubstituted (C6-C30)arylene, or a substituted or unsubstituted (3- to 30-membered)heteroarylene; and Ar$_a$ and Ar$_b$ each independently represent, hydrogen, a substituted or unsubstituted (C1-C30)alkyl, a substituted or unsubstituted (C2-C30)alkenyl, a substituted or unsubstituted fused ring of (C3-C30) aliphatic ring and an (C6-C30) aromatic ring, a substituted or unsubstituted (C6-C30)aryl, or a substituted or unsubstituted (3- to 30-membered)heteroaryl;

with the proviso that when at least one of A$_1$ and A$_2$ represent(s) N-L$_1$-Ar$_1$, X$_1$ to X$_8$ each independently represent, N or CR$_1$, and when both of A$_1$ and A$_2$ are not N-L$_1$-Ar$_1$, at least one of X$_1$ to X$_8$ represent(s) CR$_1$.

Advantageous Effects of Invention

By comprising an organic electroluminescent compound according to the present disclosure, an organic electroluminescent device having low driving voltage and/or high luminous efficiency can be prepared.

MODE FOR THE INVENTION

Hereinafter, the present disclosure will be described in detail. However, the following description is intended to explain the invention, and is not meant in any way to restrict the scope of the invention.

The present disclosure relates to an organic electroluminescent compound represented by the formula 1, an organic electroluminescent material comprising the organic electroluminescent compound, and an organic electroluminescent device comprising the organic electroluminescent compound.

The term "organic electroluminescent compound" in the present disclosure means a compound that may be used in an organic electroluminescent device, and may be comprised in any material layer constituting an organic electroluminescent device, as necessary.

Herein, "organic electroluminescent material" means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (containing host and dopant materials), an electron buffer material, a hole blocking material, an electron transport material, or an electron injection material, etc.

Herein, "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, and tert-butyl, etc. Herein, the term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. Herein, "(C6-C30)aryl(ene)" is a monocyclic or fused ring radical derived from an aromatic hydrocarbon having 6 to 30 ring backbone carbon atoms, in which the number of the ring backbone carbon atoms is preferably 6 to 20, more preferably 6 to 15, may be partially saturated, and comprise a spiro structure. Examples of the aryl specifically include phenyl, biphenyl, terphenyl, quaterphenyl, naphthyl, binaphthyl, phenylnaphthyl, naphthylphenyl, fluorenyl, phenylfluorenyl, dimethylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cumenyl, spiro[fluorene-fluorene]yl, spiro[fluorene-benzofluorene]yl, azulenyl, etc. More specifically, the aryl may be o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenyl, 4"-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, etc. Herein, "(3- to 30-membered)heteroaryl(ene)" is an aryl having 3 to 30 ring backbone atoms which the number of ring backbone atoms is preferably 5 to 25, including at least one, preferably 1 to 4 heteroatoms selected from the group consisting of B, N, O, S, Si, P, and Ge. The above heteroaryl may be a monocyclic ring, or a fused ring condensed with at least one benzene ring; and may be partially saturated. Also, the above heteroaryl herein may be one formed by linking at least one heteroaryl or aryl group to a heteroaryl group via a single bond(s). Examples of the heteroaryl specifically may include a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazolyl, benzocarbazolyl, dibenzocarbazolyl, phenoxazinyl, phenanthridinyl, benzodioxolyl, indolizidinyl, acrylidinyl, silafluorenyl, germafluorenyl, etc. More specifically, the heteroaryl may be 1-pyrrolyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyridinyl, 3-imidazopyridinyl, 5-imidazopyridinyl, 6-imidazopyridinyl, 7-imidazopyridinyl, 8-imidazopyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acrylidinyl, 2-acrylidinyl, 3-acrylidinyl, 4-acrylidinyl, 9-acrylidinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, etc. Herein, "Halogen" includes F, Cl, Br, and I.

In addition, "ortho (o)," "meta (m)," and "para (p)" are meant to signify the substitution position of all substituents. Ortho position is a compound with substituents, which are adjacent to each other, e.g., at the 1 and 2 positions on benzene. Meta position is the next substitution position of the immediately adjacent substitution position, e.g., a compound with substituents at the 1 and 3 positions on benzene. Para position is the next substitution position of the meta position, e.g., a compound with substituents at the 1 and 4 positions on benzene.

Herein, the term "a ring formed in linking to an adjacent substituent" means a substituted or unsubstituted (3- to 30-membered) mono- or polycyclic, alicyclic, aromatic ring, or a combination thereof, formed by linking or fusing two or more adjacent substituents, preferably may be a substituted or unsubstituted (3- to 26-membered) mono- or polycyclic, alicyclic, aromatic ring, or a combination thereof. Further, the formed ring may be included at least one heteroatom selected from the group consisting of B, N, O, S, Si and P, preferably at least one heteroatom selected from the group consisting of N, O and S. According to one embodiment of the present disclosure, the number of atoms in the ring skeleton is 5 to 20; according to another embodiment of the present disclosure, the number of atoms in the ring skeleton is 5 to 15. The linked or fused ring may be, for example, a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring, etc.

In addition, "substituted" in the expression "substituted or unsubstituted" described in of the present disclosure means that a hydrogen atom in a certain functional group is replaced with another atom or functional group, i.e., a substituent. The substituent of the substituted (C1-C30) alkyl, the substituted (C2-C30)alkenyl, the substituted (C6-C30)aryl(ene), the substituted (3- to 30-membered)heteroaryl(ene), the substituted (C3-C30)cycloalkyl, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, and the substituted fused ring of (C3-C30) aliphatic ring and the (C6-C30) aromatic ring, each independently are at least one selected from the group consisting of deuterium, halogen, cyano, carboxyl, nitro, hydroxy, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered)heterocycloalkyl, (C6-C30)aryloxy, (C6-C30)arylthio, (5- to 30-membered)heteroaryl unsubstituted or substituted with (C6-C30)aryl, (C6-C30)aryl unsubstituted or substituted with (5- to 30-membered)heteroaryl, tri(C1-C30)alkylsilyl, tri(C6-C30)arylsilyl, di(C1-C30)alkyl(C6-C30)arylsilyl, (C1-C30)alkyldi(C6-C30)arylsilyl, a fused ring of an (C3-C30) aliphatic ring and an (C6-C30) aromatic ring, amino, mono- or di-(C1-C30)alkylamino, mono- or di-(C2-C30)alkenylamino, (C1-C30)alkyl(C2-C30)alkenylamino, a substituted or unsubstituted mono- or di-(C6-C30)arylamino, (C1-C30)alkyl(C6-C30)arylamino, mono- or di-(3- to 30-membered)heteroarylamino, (C1-C30)alkyl(3- to 30-membered)heteroarylamino, (C2-C30)alkenyl(C6-C30)arylamino, (C2-C30)alkenyl(3- to 30-membered)heteroarylamino, (C6-C30)aryl(3- to 30-membered)heteroarylamino, (C1-C30)alkylcarbonyl, (C1-C30)alkoxycarbonyl, (C6-C30)arylcarbonyl, di(C6-C30)arylboronyl, di(C1-C30)alkylboronyl, (C1-C30)alkyl(C6-C30)arylboronyl, (C6-C30)ar(C1-C30)alkyl, and (C1-C30)alkyl(C6-C30)aryl. For example, the substituent may be phenyl, naphthyl, p-biphenyl, m-biphenyl, or triazinyl, etc.

Hereinafter, the organic electroluminescent compound according to one embodiment will be described.

The organic electroluminescent compound according to one embodiment is represented by the following formula 1.

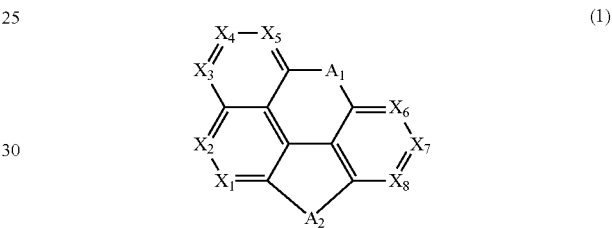

(1)

In formula 1

$A_1$ and $A_2$ each independently represent, N-$L_1$-$Ar_1$, O, or S;

$X_1$ to $X_8$ each independently represent, N or $CR_1$;

$L_1$ represents a single bond, a substituted or unsubstituted (C6-C30)arylene, or a substituted or unsubstituted (3- to 30-membered)heteroarylene;

$Ar_1$ and $R_1$ each independently represent, hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and an (C6-C30) aromatic ring, or -$L_a$-N—($Ar_a$)($Ar_b$); or may be linked to the adjacent substituent to form a ring(s);

$L_a$ represents a single bond, a substituted or unsubstituted (C6-C30)arylene, or a substituted or unsubstituted (3- to 30-membered)heteroarylene; and $Ar_a$ and $Ar_b$ each independently represent, hydrogen, a substituted or unsubstituted (C1-C30)alkyl, a substituted or unsubstituted (C2-C30)alkenyl, a substituted or unsubstituted fused ring of (C3-C30) aliphatic ring and an (C6-C30) aromatic ring, a substituted or unsubstituted (C6-C30)aryl, or a substituted or unsubstituted (3- to 30-membered)heteroaryl;

with the proviso that when at least one of $A_1$ and $A_2$ represent(s) N-$L_1$-$Ar_1$, $X_1$ to $X_8$ each independently represent, N or $CR_1$, and when both of $A_1$ and $A_2$ are not N-$L_1$-$Ar_1$, at least one of $X_1$ to $X_5$ represent(s) $CR_1$.

In one embodiment, $A_1$ and $A_2$ each independently represent N-$L_1$-$Ar_1$, O, or S, for example, $A_1$ may be O or S, and $A_2$ may be N-$L_1$-$Ar_1$, O, or S.

In one embodiment, $L_a$ may be a single bond or a substituted or unsubstituted (C6-C30)arylene, preferably, a single bond or a substituted or unsubstituted (C6-C25) arylene, more preferably, a single bond or a substituted or unsubstituted (C6-C18)arylene. For example, $L_a$ may be a single bond, or a substituted or unsubstituted phenylene, or a substituted or unsubstituted biphenylene.

In one embodiment, $Ar_a$ and $Ar_b$ each independently may be a substituted or unsubstituted (C6-C30)aryl or a substituted or unsubstituted (5- to 30-membered)heteroaryl, preferably a substituted or unsubstituted (C6-C25)aryl or a substituted or unsubstituted (5- to 25-membered)heteroaryl, more preferably a substituted or unsubstituted (C6-C18)aryl or a substituted or unsubstituted (5- to 18-membered)heteroaryl. For example, $Ar_a$ and $Ar_b$ each independently may be a substituted or unsubstituted phenyl, a substituted or unsubstituted p-biphenyl, a substituted or unsubstituted m-biphenyl, a substituted or unsubstituted o-biphenyl, a substituted or unsubstituted naphthyl, a substituted or unsubstituted fluorenyl, or a substituted or unsubstituted carbazolyl.

According to one embodiment, the organic electroluminescent compound of formula 1 may be represented by any one of the following formulas 2-1 to 2-6.

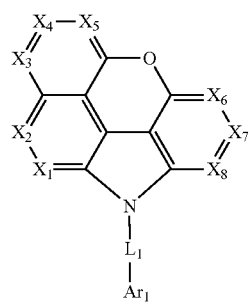

(2-1)

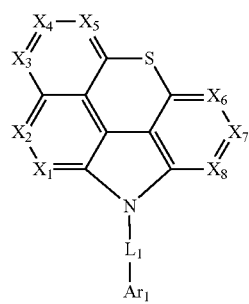

(2-2)

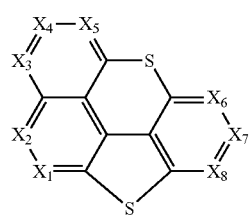

(2-3)

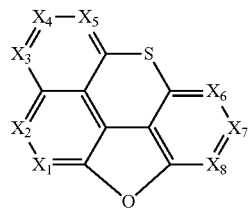

(2-4)

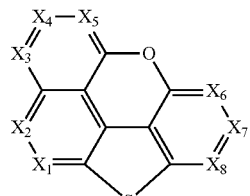

(2-5)

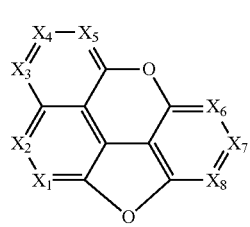

(2-6)

In formulas 2-1 to 2-6, $X_1$ to $X_8$, $L_1$, and $Ar_1$ each independently are as defined in the formula 1.

In one embodiment, $L_1$ may be a single bond, a substituted or unsubstituted (C6-C30)arylene, or a substituted or unsubstituted (5- to 30-membered)heteroarylene, preferably, a single bond, a substituted or unsubstituted (C6-C25)arylene, or a substituted or unsubstituted (5- to 25-membered)heteroarylene, more preferably, a single bond, a substituted or Unsubstituted (C6-C18)arylene, or a substituted or Unsubstituted (5- to 18-membered)heteroarylene. For example, $L_1$ may be a single bond, or a substituted or unsubstituted phenylene, a substituted or unsubstituted naphthylene, a substituted or unsubstituted quinazolinylene, a substituted or unsubstituted quinoxalinylene, a Substituted or unsubstituted benzoquinazolinylene, a substituted or unsubstituted benzothienopyrimidylene, or a substituted or Unsubstituted benzofuropyrimidylene.

In one embodiment, $Ar_1$ may be a substituted or unsubstituted (C6-C30)aryl, a substituted or unsubstituted (3- to 30-membered)heteroaryl, or -$L_a$-N—($Ar_a$)($Ar_b$), preferably, a substituted or unsubstituted (C6-C25)aryl, a substituted or unsubstituted (5- to 30-membered)heteroaryl, a substituted or unsubstituted mono- or di-(C6-C30)arylamino, or a substituted or unsubstituted (C6-C30)aryl(5- to 30-membered)heteroarylamino, more preferably, a substituted or unsubstituted (C6-C18)aryl, (5- to 25-membered)heteroaryl unsubstituted or substituted with at least one substituted or unsubstituted (C6-C18)aryl, a substituted or unsubstituted di(C6-C25)arylamino, or a substituted or unsubstituted (C6-C25)aryl(5- to 25-membered)heteroarylamino. For example, $Ar_1$ may be a substituted or unsubstituted phenyl, a substituted or unsubstituted naphthyl, a substituted or unsubstituted p-biphenyl, a substituted or unsubstituted m-biphenyl, a substituted or unsubstituted triazinyl, a substituted or unsubstituted quinazolyl, a substituted or unsubstituted quinoxalyl, a substituted or unsubstituted benzoquinazolyl, a substituted or unsubstituted benzothienopyrimidyl, or a substituted or unsubstituted benzofuropyrimidyl; or an amino substituted with at least one of a substituted or unsubstituted phenyl, a substituted or unsubstituted p-biphenyl, a substituted or unsubstituted m-biphenyl, a substituted or unsubstituted o-biphenyl, a substituted or unsubstituted naphthyl, a substituted or unsubstituted fluorenyl, and a substituted or unsubstituted carbazolyl.

In the organic electroluminescent compound represented by formulas 2-1 and 2-2 above according to one embodiment, $L_1$ may be a single bond, a substituted or unsubstituted (C6-C30)arylene, or a substituted or unsubstituted (5- to 30-membered)heteroarylene; and $Ar_1$ may be a substituted or unsubstituted (C6-C30)aryl or a substituted or unsubstituted (5- to 30-membered)heteroaryl, or a substituted or unsubstituted fused ring of (C5-C18) aliphatic ring and an (C6-C18) aromatic ring.

In one embodiment, $X_1$ to $X_8$ each independently may be N or $CR_1$, preferably, all of $X_1$ to $X_8$ may be $CR_1$. In this case, $R_1$ according to one embodiment each independently may be hydrogen, a substituted or unsubstituted (C6-C30)aryl, or a substituted or unsubstituted (3- to 30-membered)heteroaryl; or $-L_a$-N—$(Ar_a)(Ar_b)$, preferably, hydrogen, a substituted or unsubstituted (C6-C25)aryl, or a substituted or unsubstituted (5- to 25-membered)heteroaryl; or $-L_a$-N—$(Ar_a)(Ar_b)$, in which $L_a$ may be a single bond or a substituted or unsubstituted (C6-C25)arylene, and $Ar_a$ and $Ar_b$ each independently may be a substituted or unsubstituted (C6-C25)aryl, or a substituted or unsubstituted (5- to 25-membered)heteroaryl, more preferably, hydrogen, (C6-C18)aryl unsubstituted or substituted with at least one substituted or unsubstituted (5- to 18-membered)heteroaryl, or (5- to 25-membered)heteroaryl unsubstituted or substituted with at least one substituted or unsubstituted (C6-C18)aryl; or $-L_a$N—$(Ar_a)(Ar_b)$, in which $L_a$ may be a single bond or a substituted or unsubstituted (C6-C18)arylene, and $Ar_a$ and $Ar_b$ each independently may be a substituted or unsubstituted (C6-C18)aryl, or a substituted or unsubstituted (5- to 18-membered)heteroaryl. For example, $R_1$ may be hydrogen, or a substituted or unsubstituted phenyl, a substituted or unsubstituted naphthyl, a substituted or unsubstituted triazinyl, a substituted or unsubstituted quinazolinyl, a substituted or unsubstituted quinoxalinyl, a substituted or unsubstituted benzoquinazolinyl, a substituted or unsubstituted benzothienopyrimidyl, or a substituted or unsubstituted benzofuropyrimidyl; or $-L_a$-N—$(Ar_a)(Ar_b)$, in which $L_a$ may be a substituted or unsubstituted phenylene, and $Ar_a$ and $Ar_b$ each independently may be a substituted or unsubstituted phenyl, a substituted or unsubstituted p-biphenyl, a substituted or unsubstituted m-biphenyl, a substituted or unsubstituted naphthyl, a substituted or unsubstituted fluorenyl, or a substituted or unsubstituted carbazolyl.

In the organic electroluminescent compound represented by formula 1 above according to one embodiment, when at least one of $A_1$ and $A_2$ represent(s) $N-L_1-Ar_1$, $X_1$ to $X_8$ each independently represent, N or $CR_1$, and when both of $A_1$ and $A_2$ are not $N-L_1-Ar_1$, at least one of $X_1$ to $X_8$ represent(s) $CR_1$.

According to one embodiment, the organic electroluminescent compound represented by formula 1 above may be more specifically illustrated by the following compounds, but is not limited thereto,

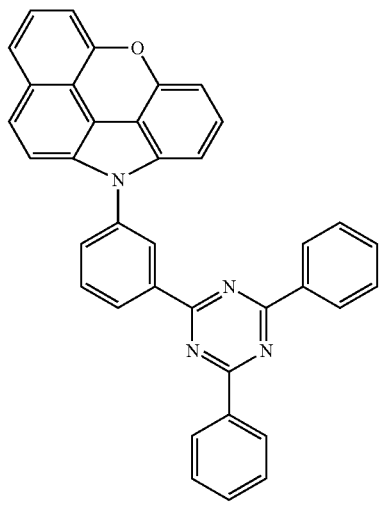

C-1

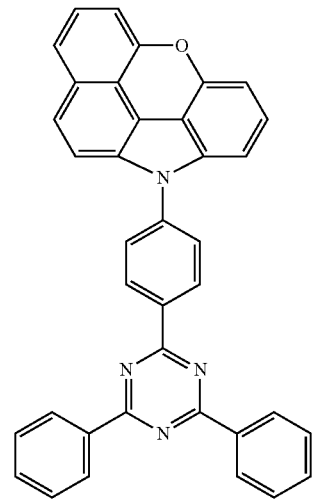

C-2

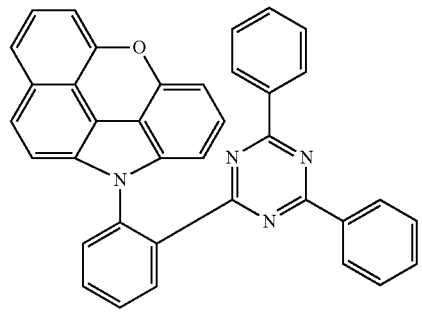

C-3

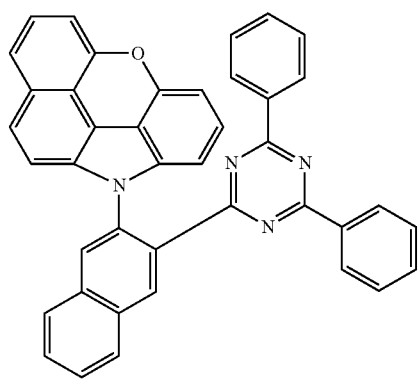
C-4
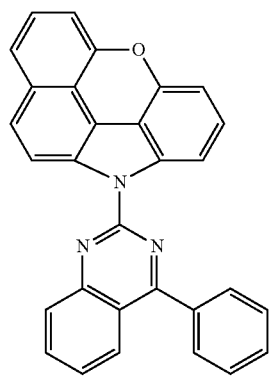
C-7
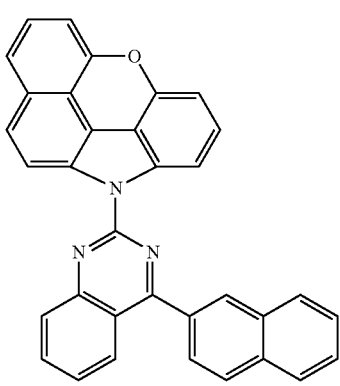
C-8
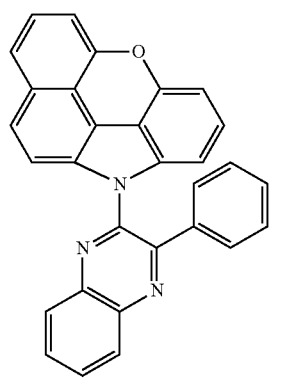
C-9
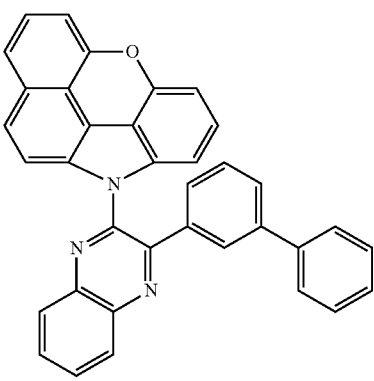
C-10

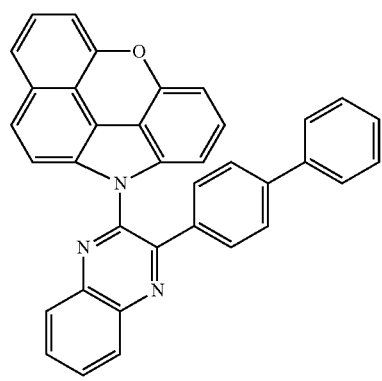
C-11
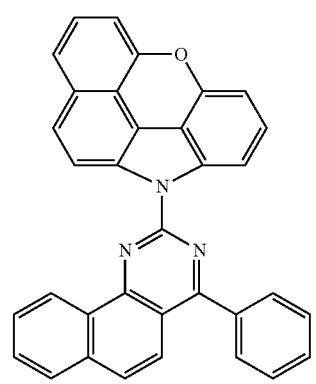
C-12
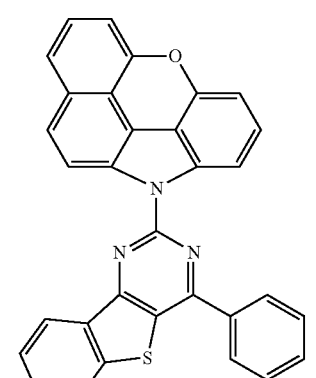
C-13
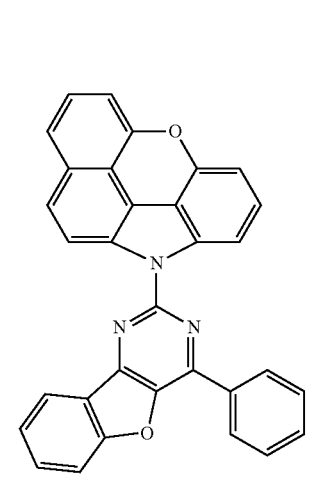
C-14
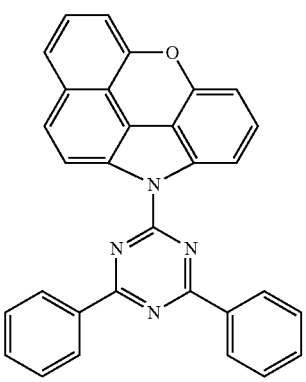
C-15
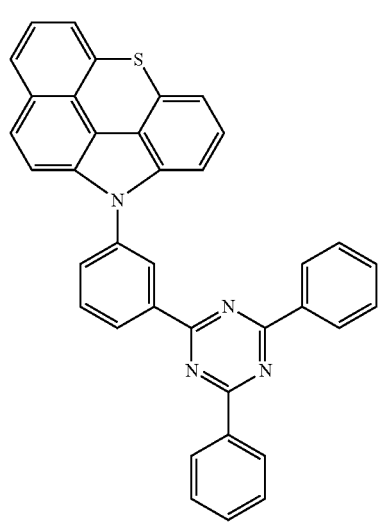
C-16
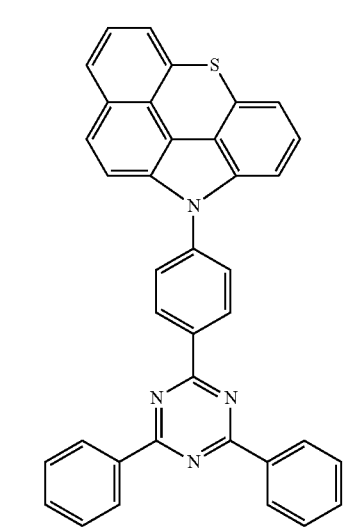
C-17

C-18
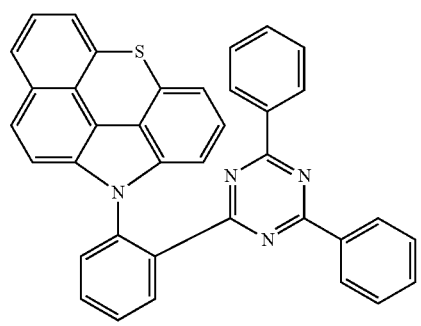
C-19
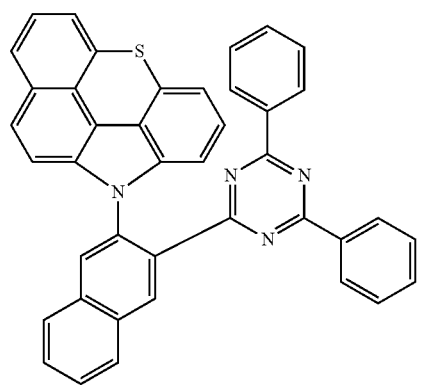
C-20
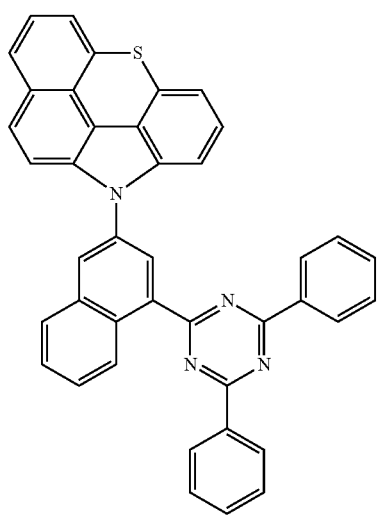
C-21
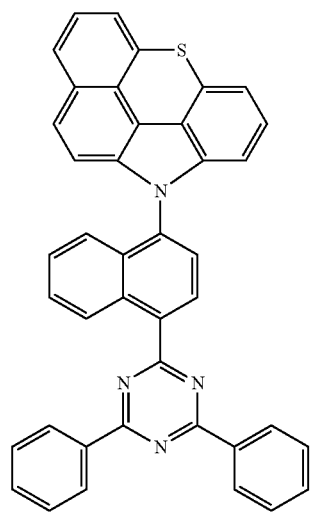
C-22
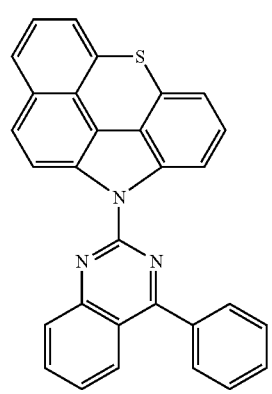
C-23
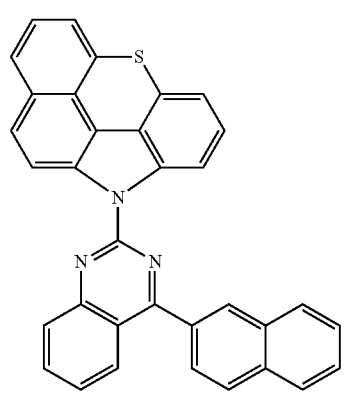

C-24
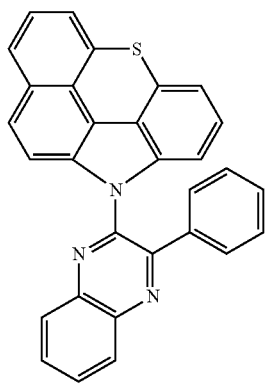
C-25
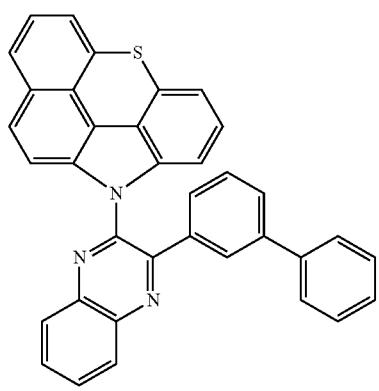
C-26
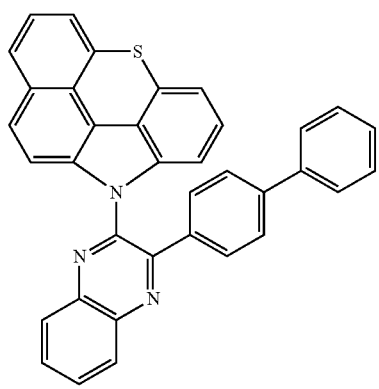
C-27
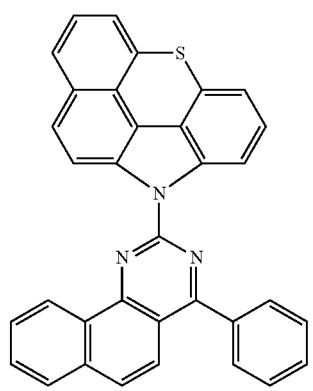
C-28
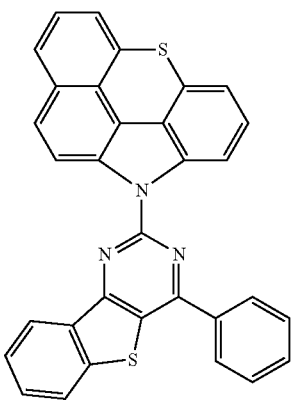
C-29
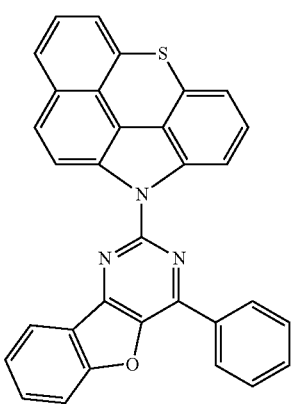
C-30
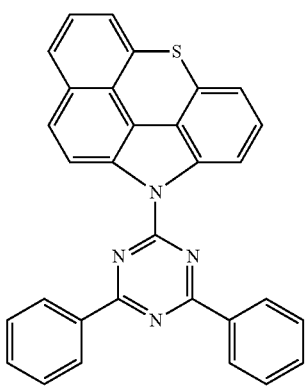

C-31 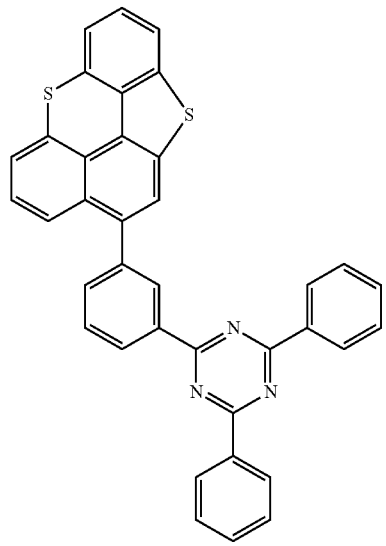
C-34 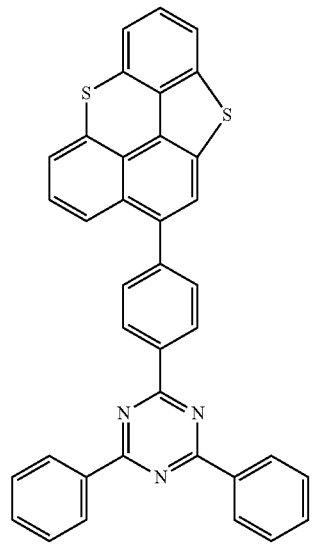
C-32 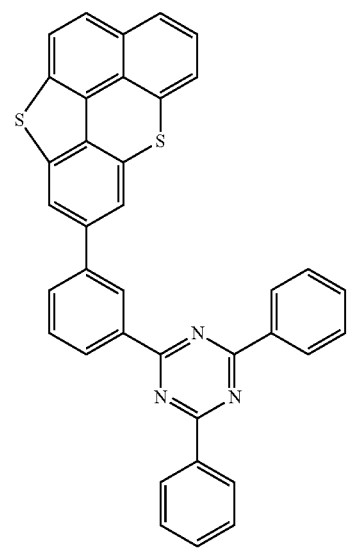
C-35 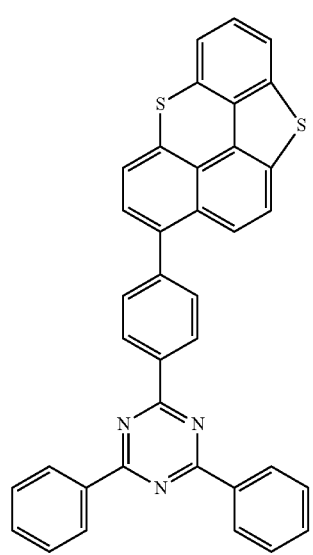
C-33
C-36 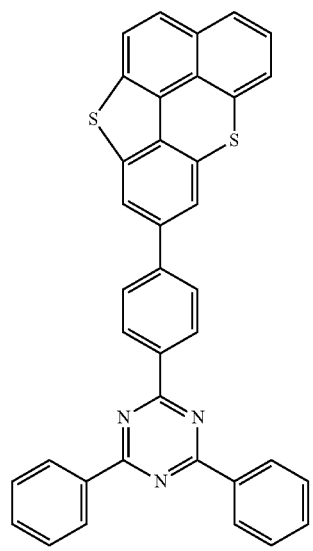

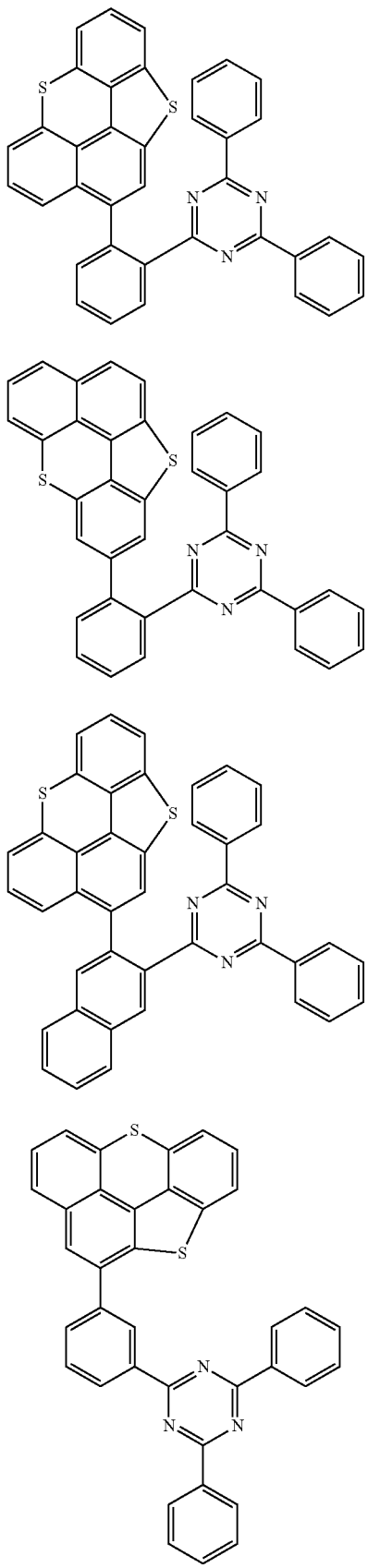
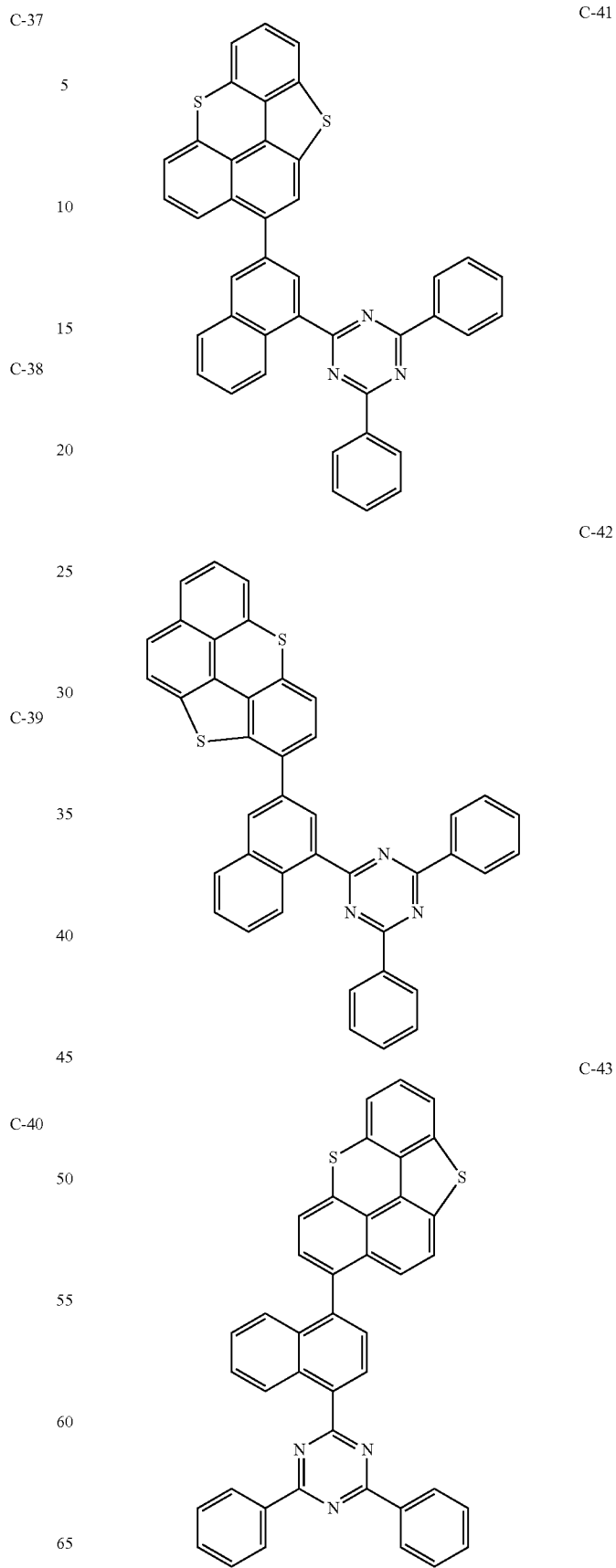

C-44
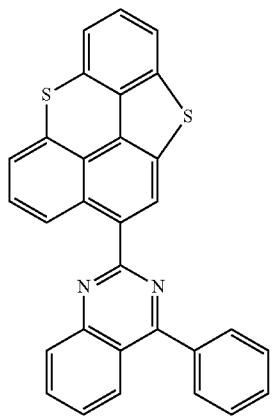
C-45
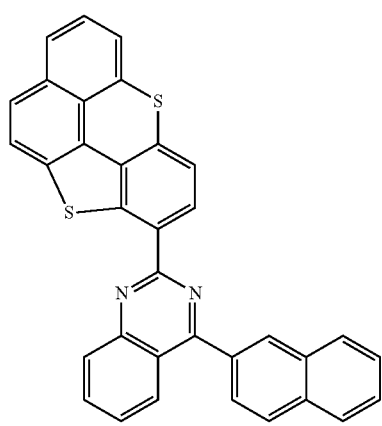
C-46
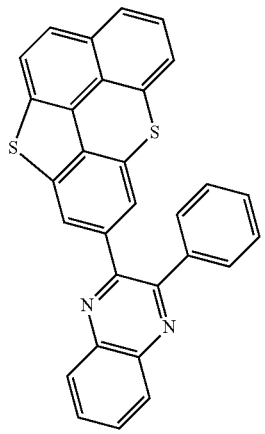
C-47
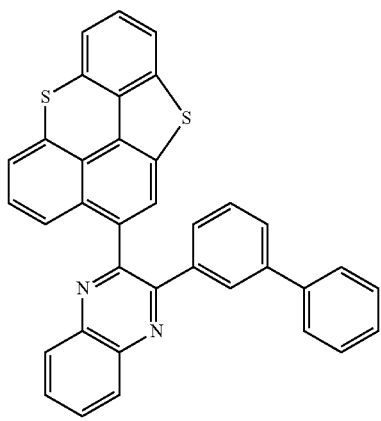
C-48
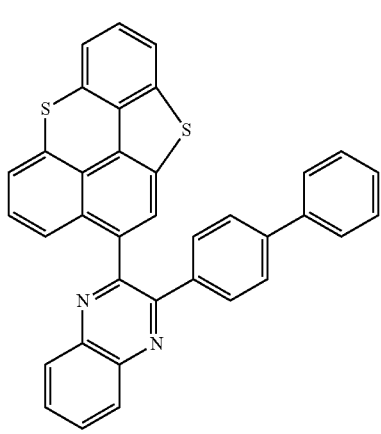
C-49
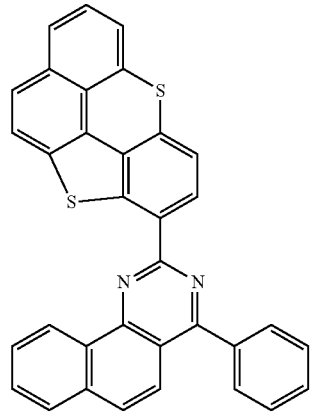

C-50
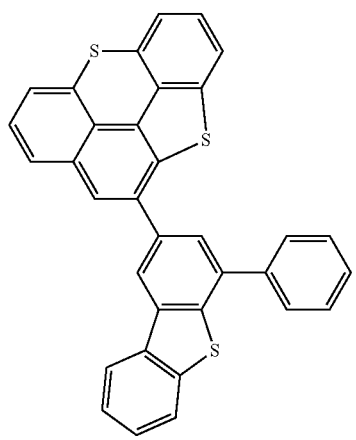
C-51
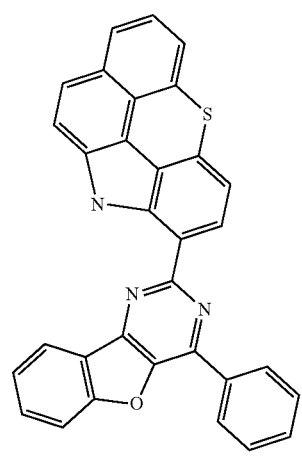
C-52
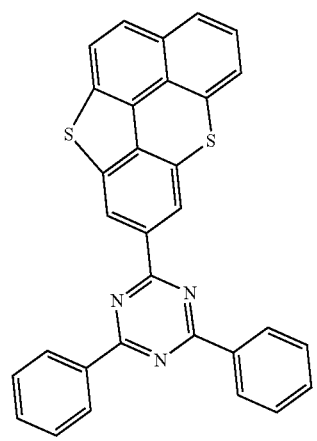
C-53
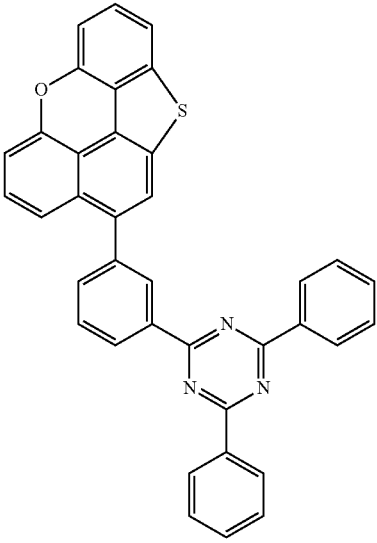
C-54
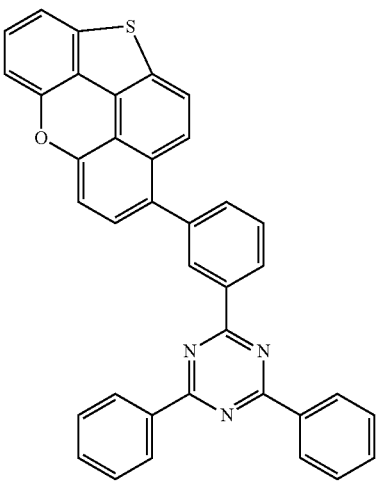
C-55
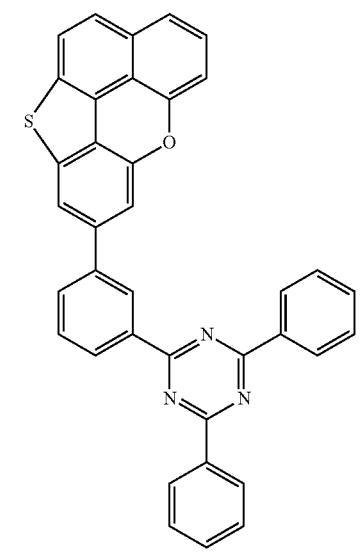

C-56
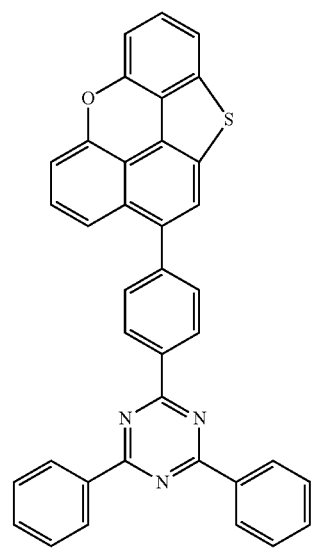
C-57
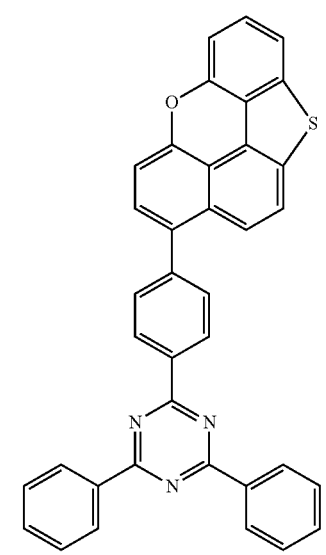
C-58
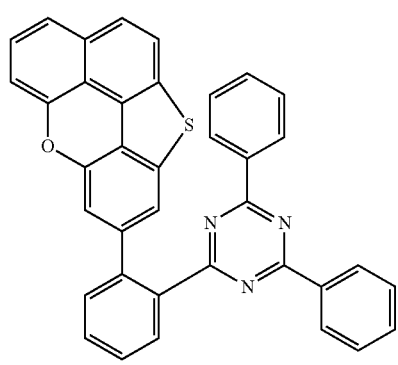
C-59
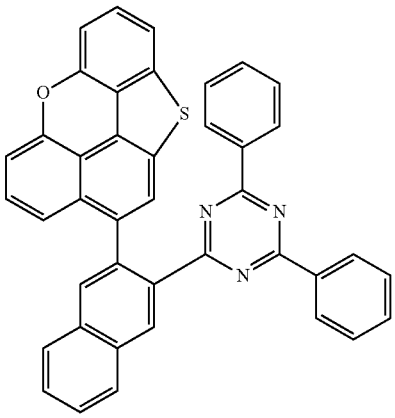
C-60
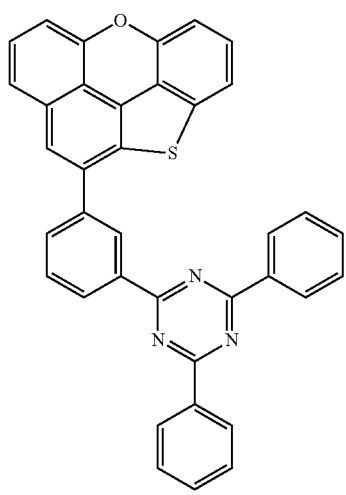
C-61
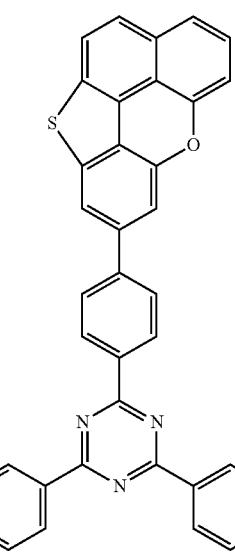

C-62
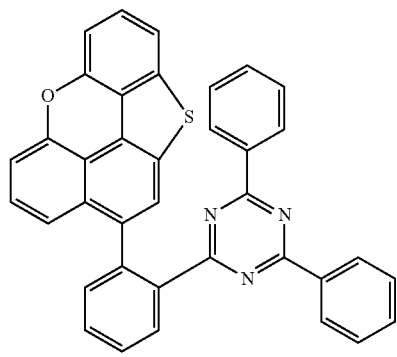
C-63
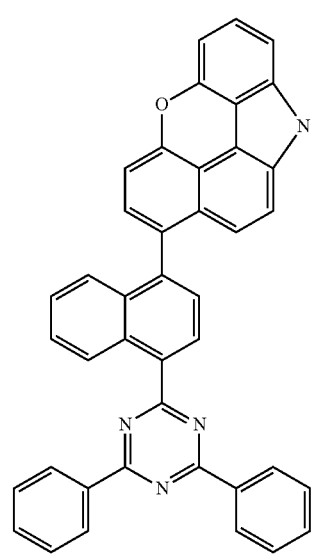
C-64
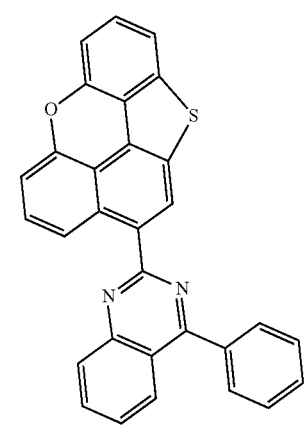
C-65
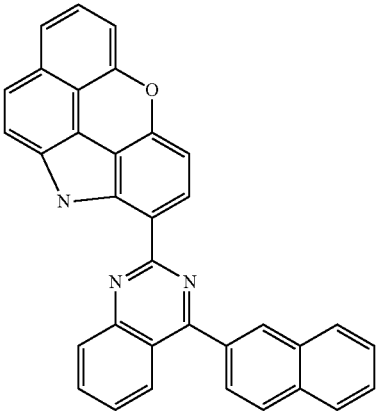
C-66
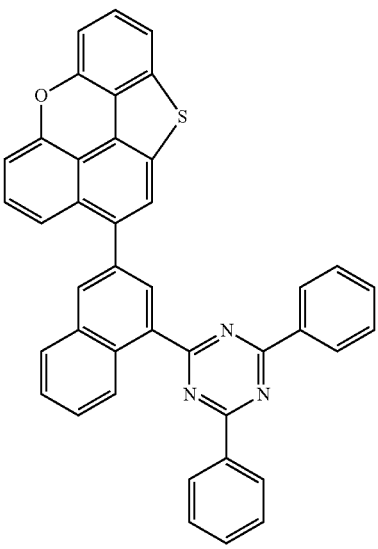
C-67
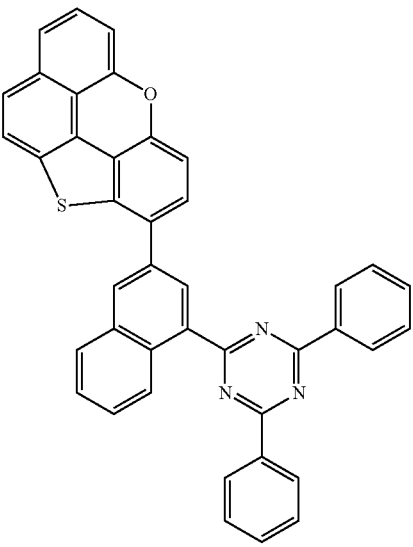

-continued
C-68
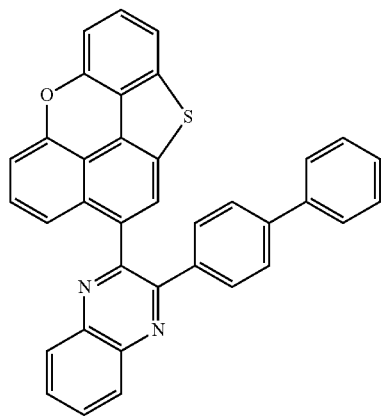
C-69
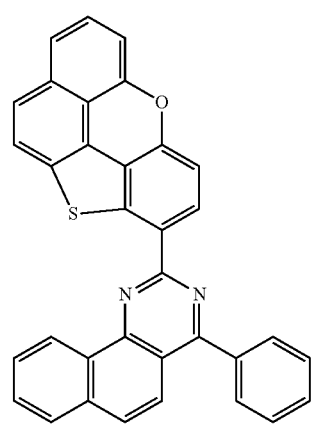
C-70
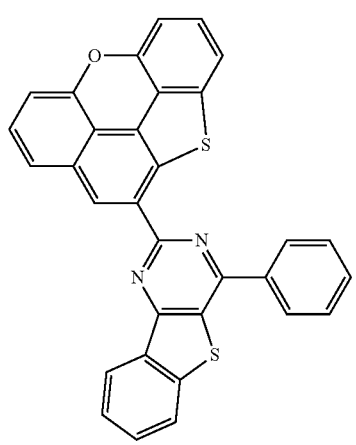
-continued
C-71
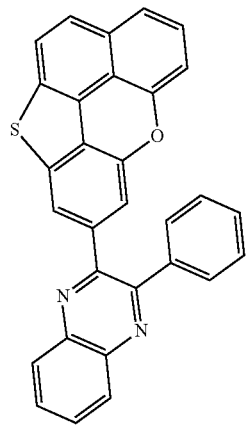
C-72
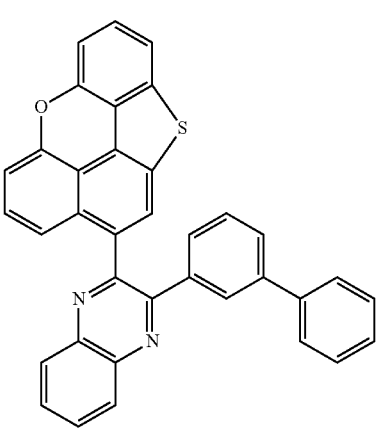
C-73
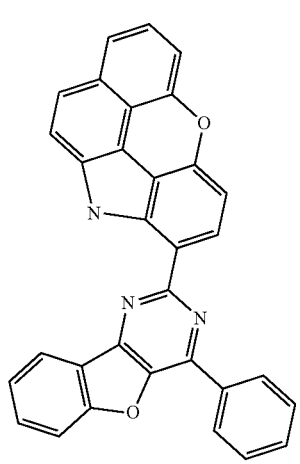

C-74
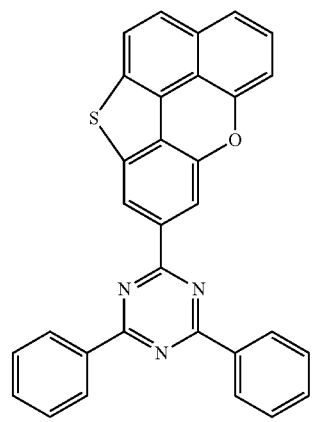
C-75
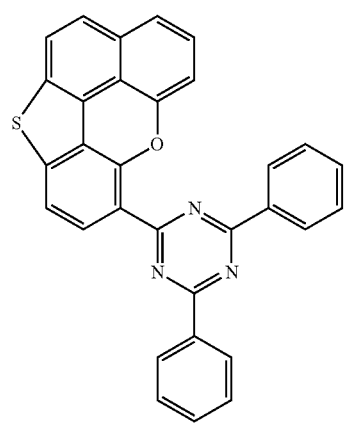
C-76
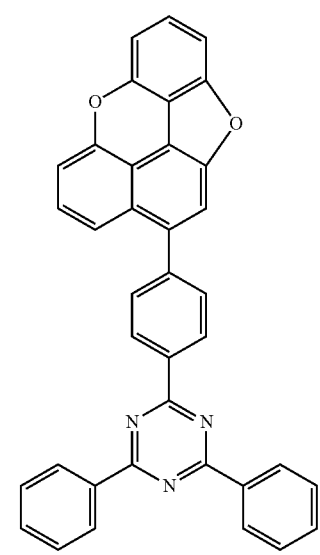
C-77
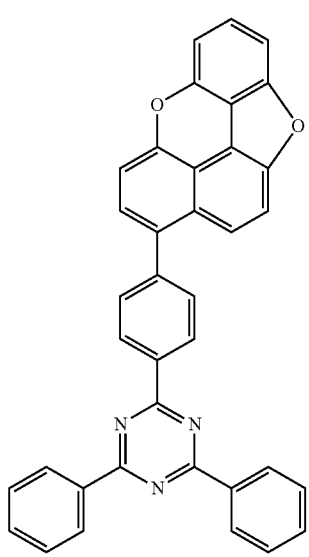
C-78
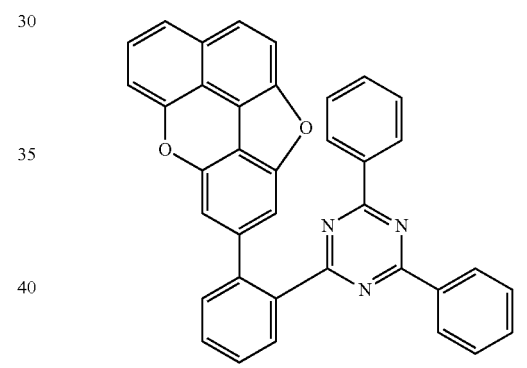
C-79
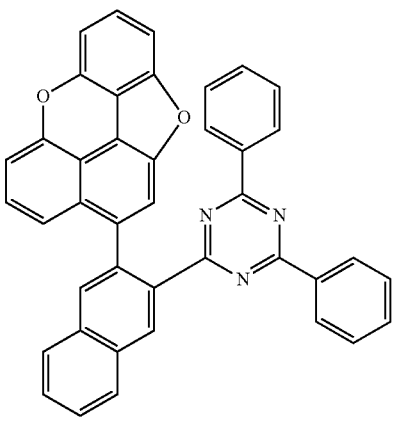

C-80
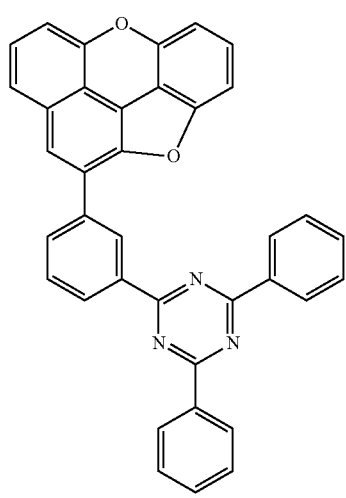
C-81
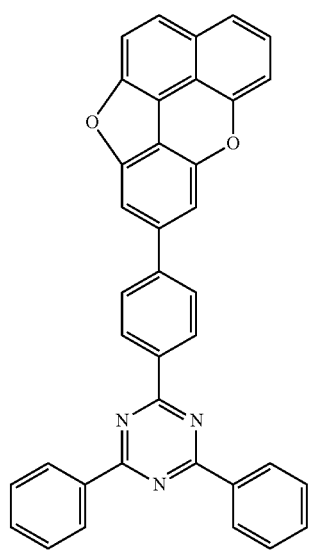
C-82
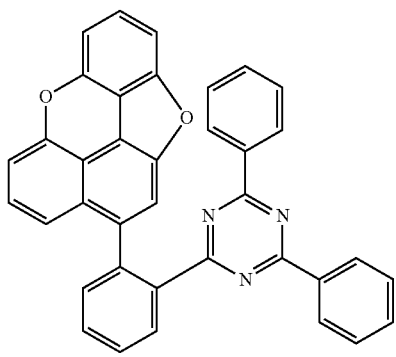
C-83
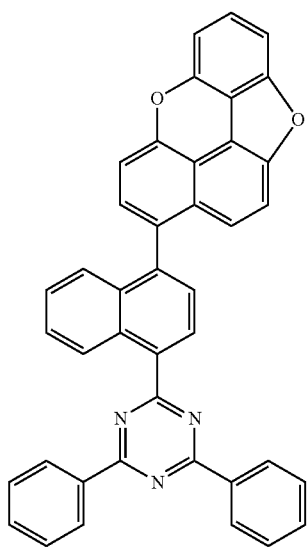
C-84
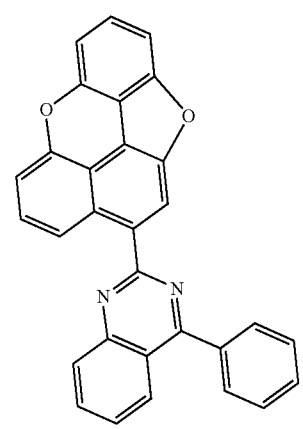
C-85
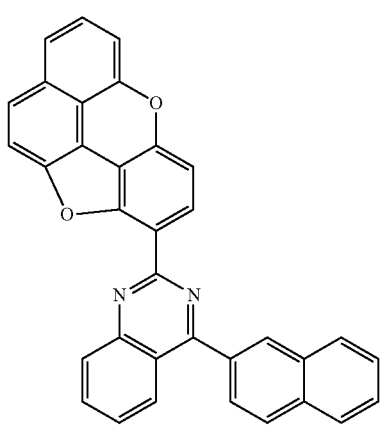

C-86 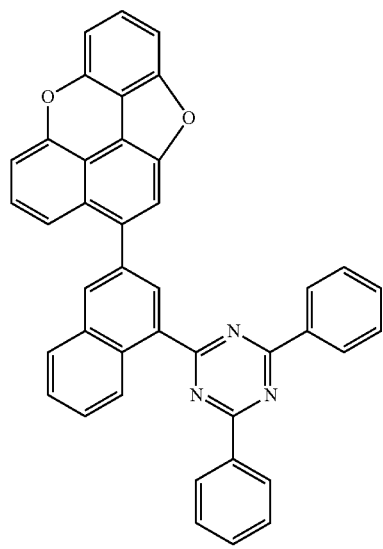
C-87 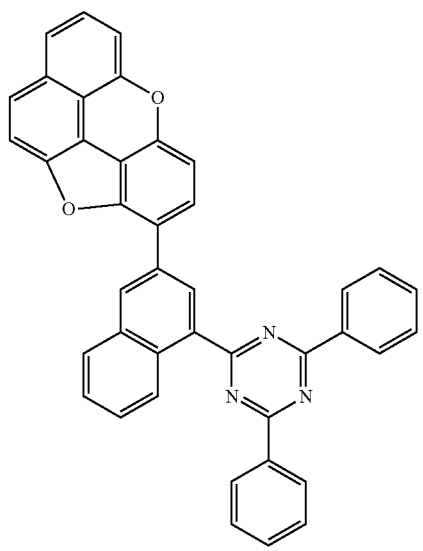
C-88 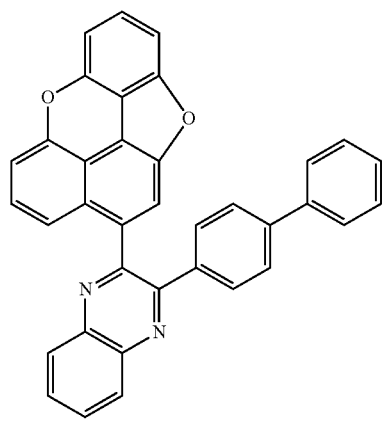
C-89 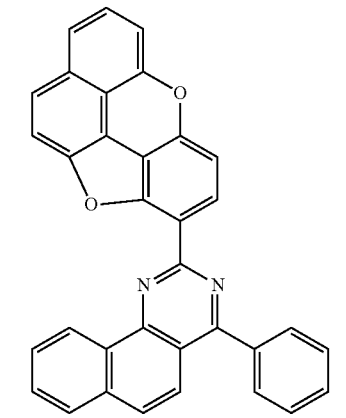
C-90 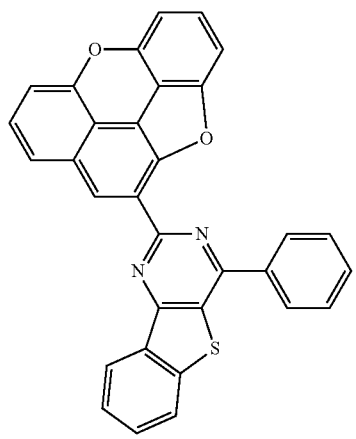
C-91 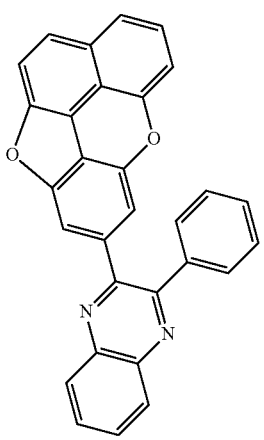

C-92
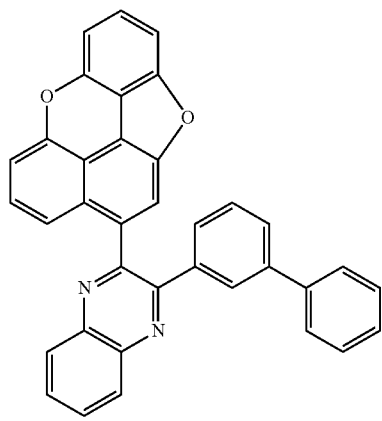
C-93
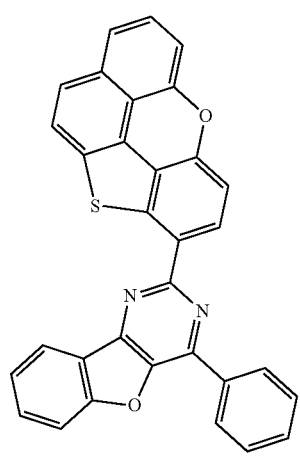
C-94
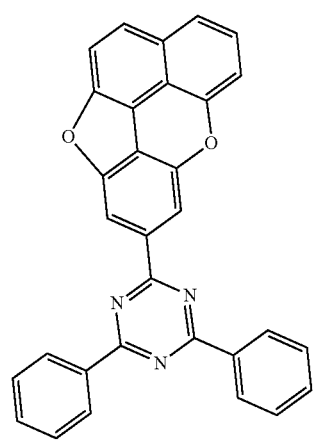
C-95
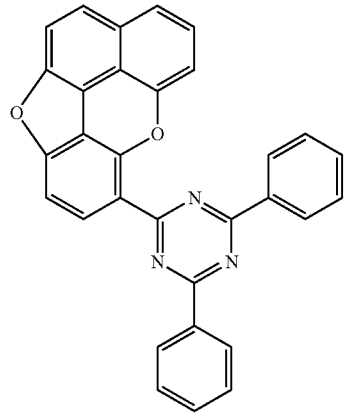
C-96
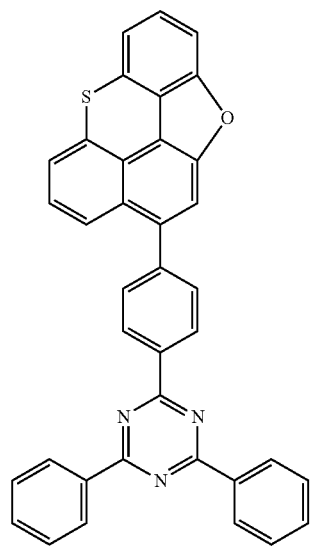
C-97
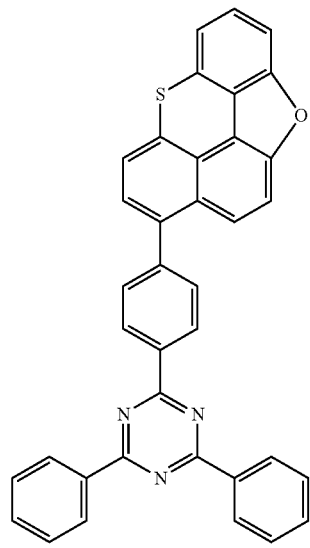

C-98
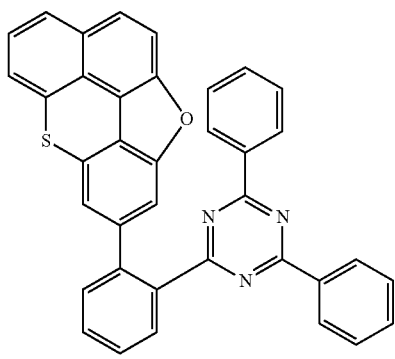
C-99
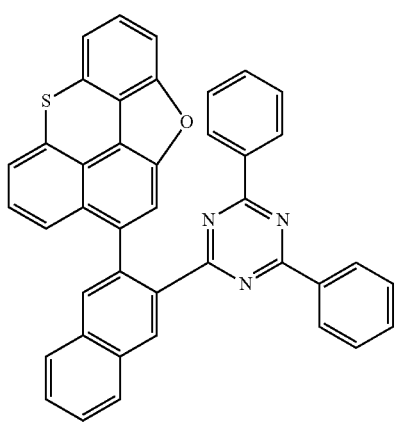
C-100
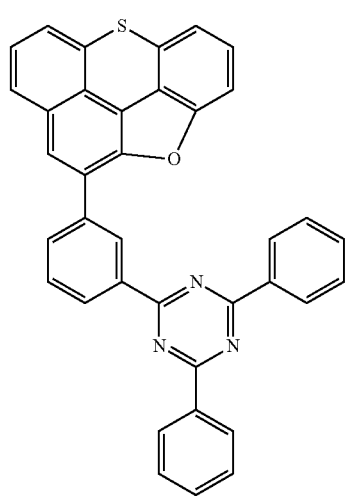
C-101
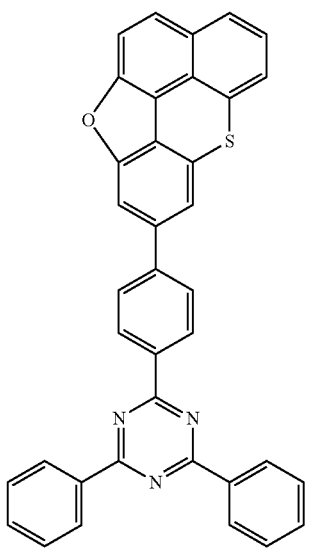
C-102
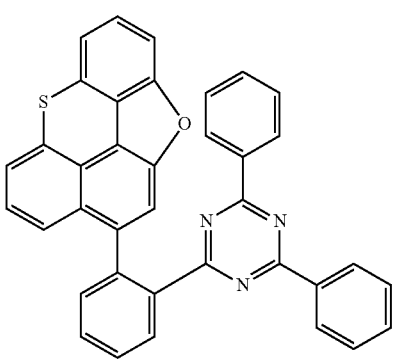
C-103
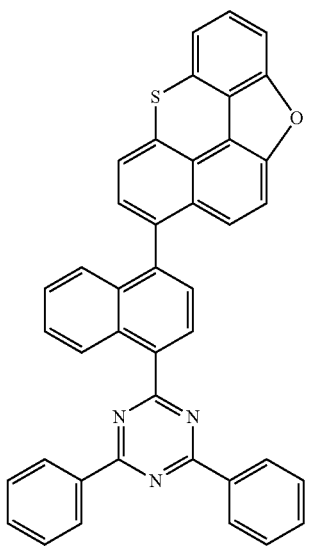

C-104
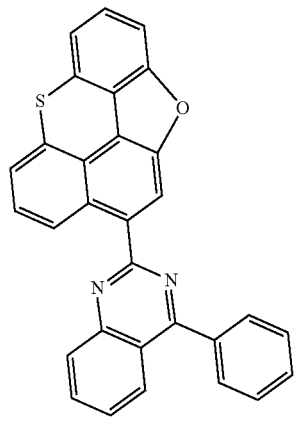
C-105
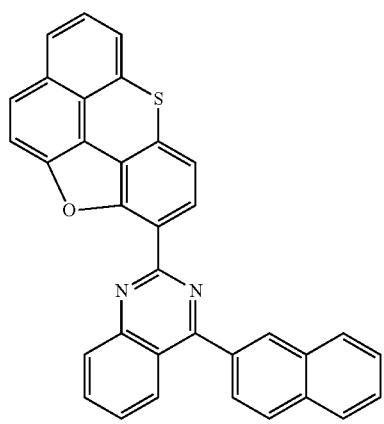
C-106
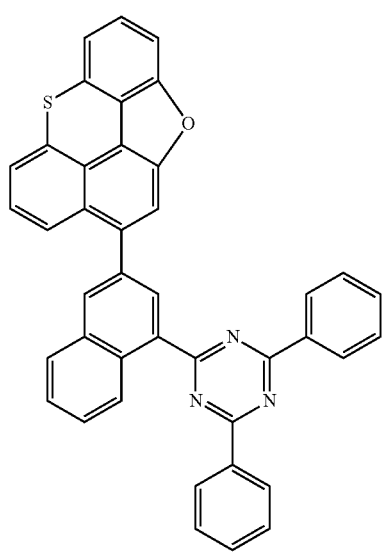
C-107
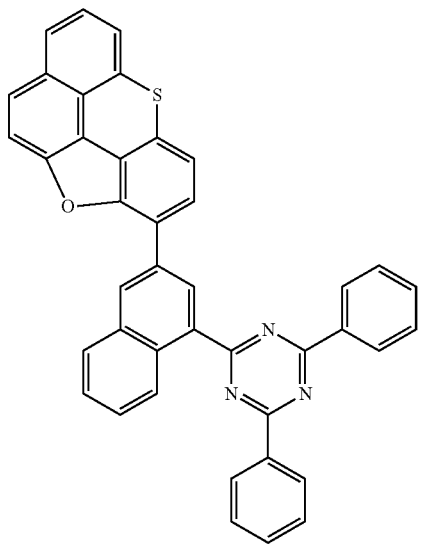
C-108
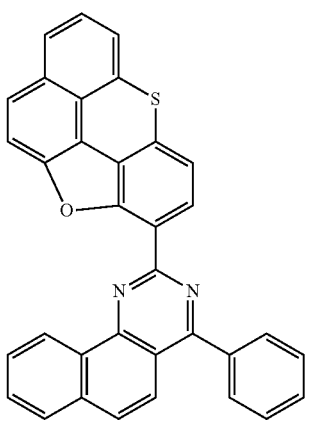
C-109

C-110
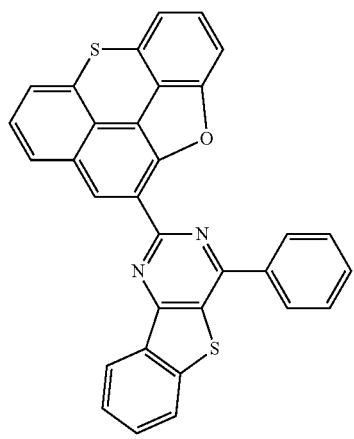
C-111
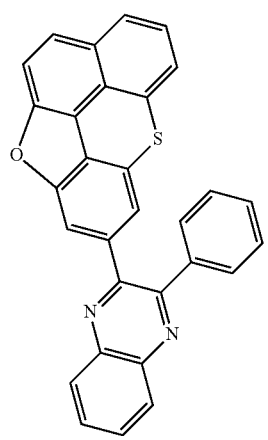
C-112
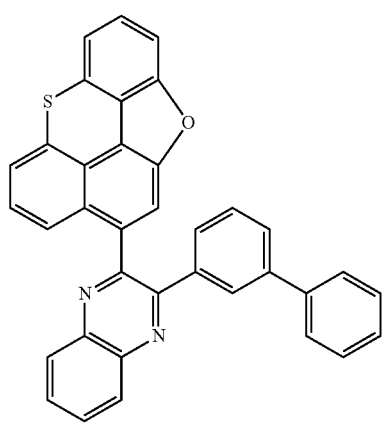
C-113
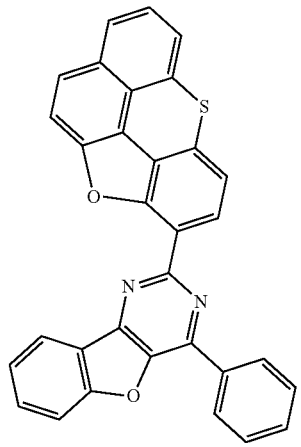
C-114
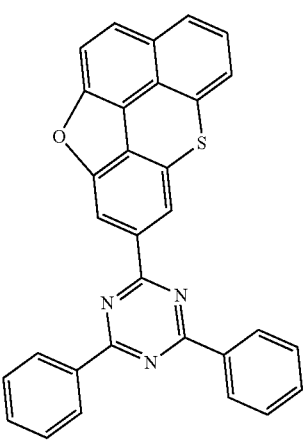
C-115
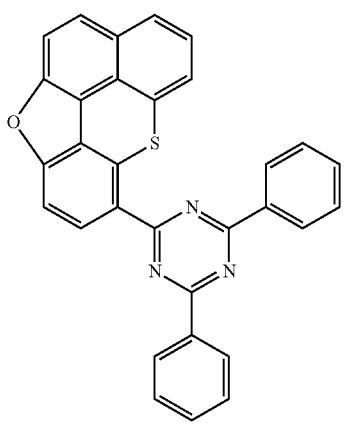

C-116
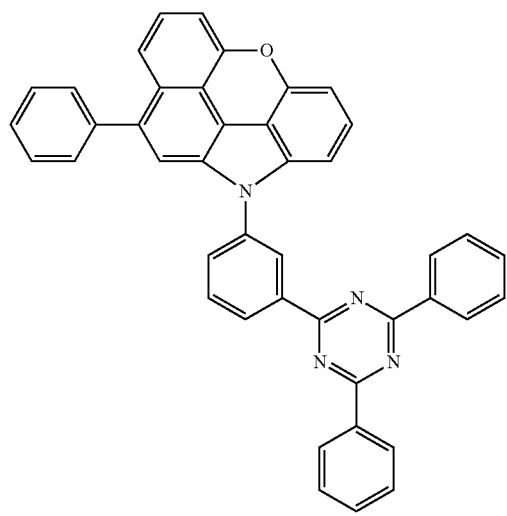
C-117
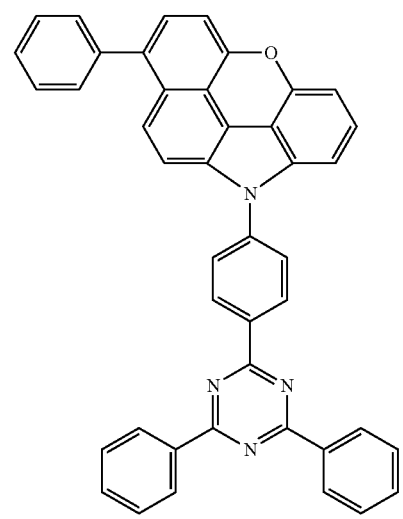
C-118
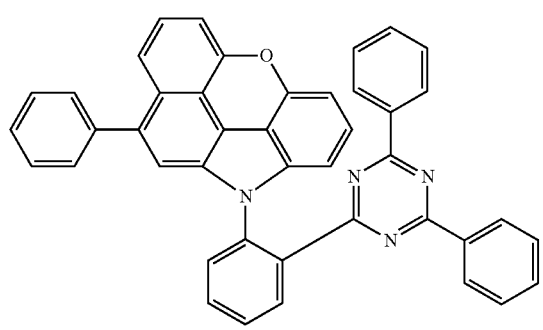
C-119
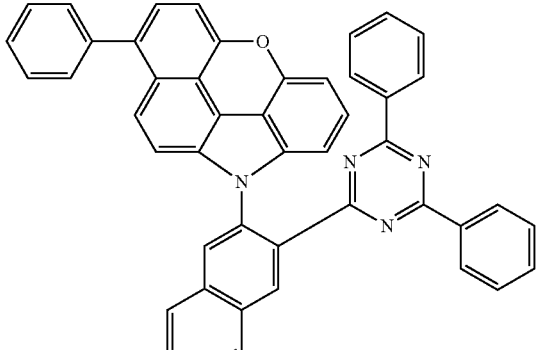
C-120
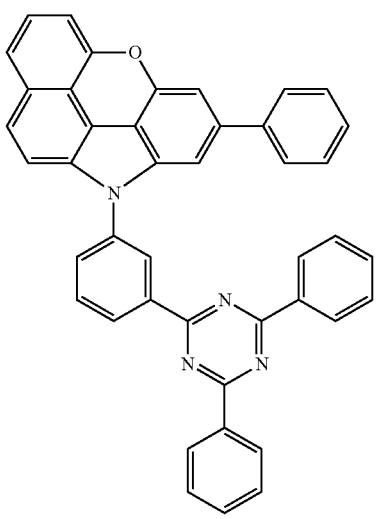
C-121
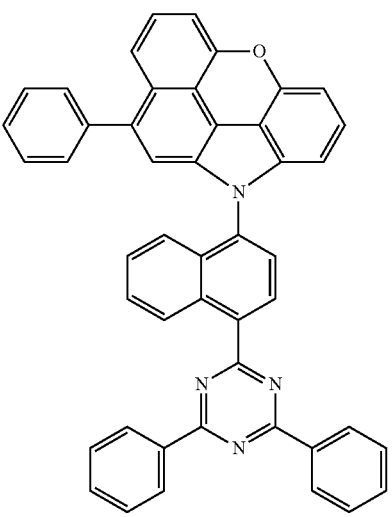

49
-continued
C-122
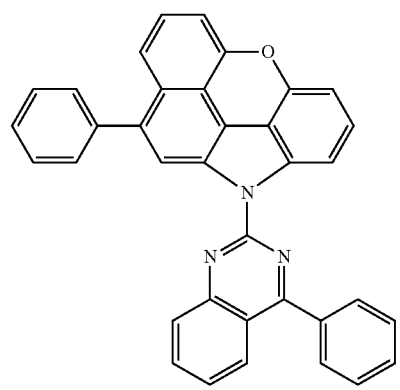
C-123
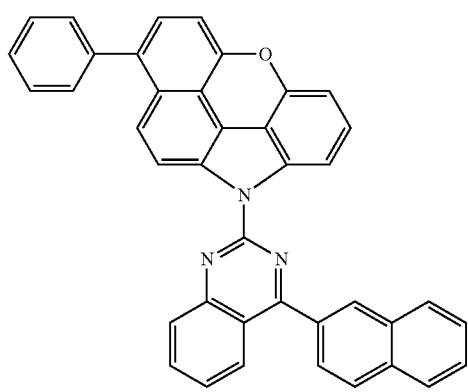
C-124
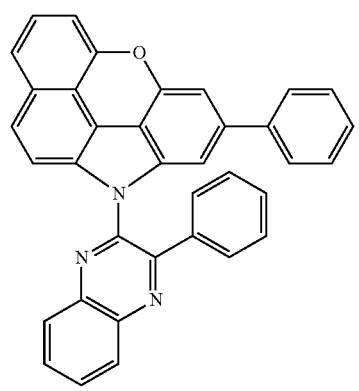
C-125
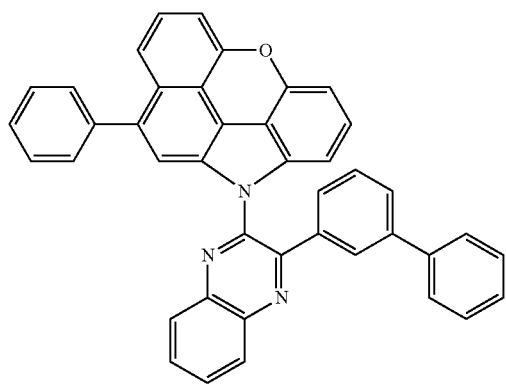
50
-continued
C-126
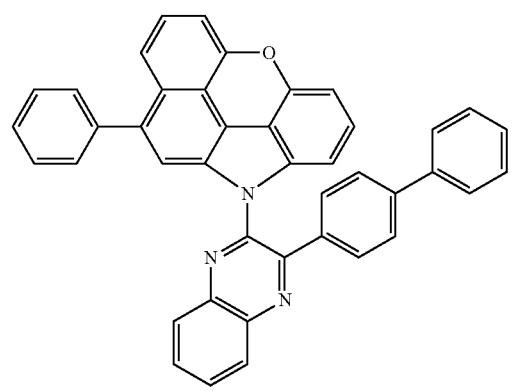
C-127
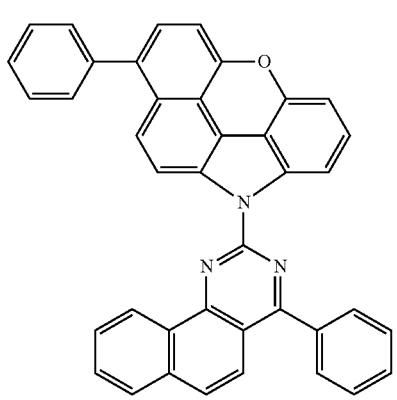
C-128
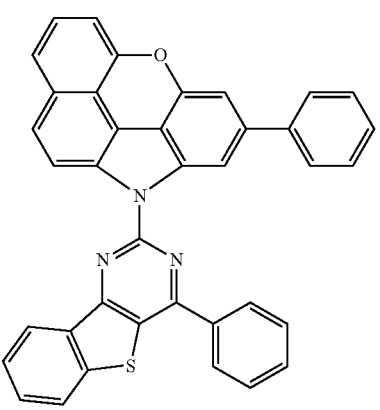
C-129
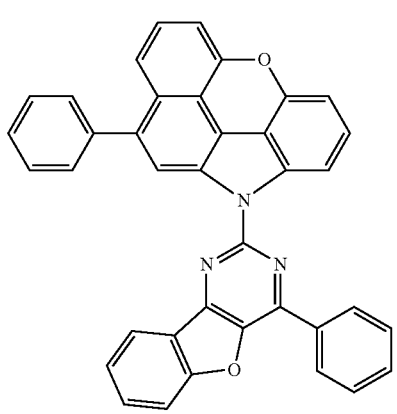

C-130
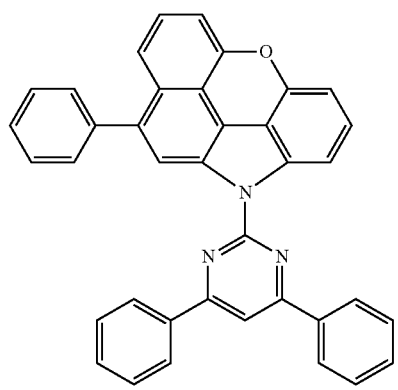
C-131
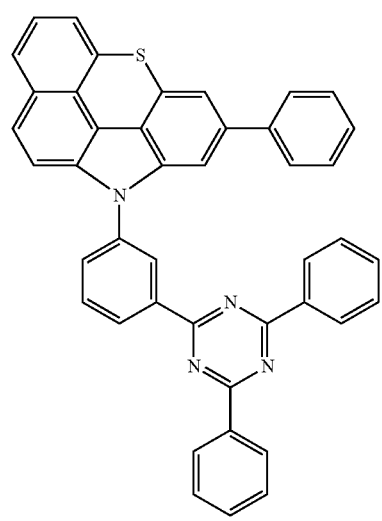
C-132
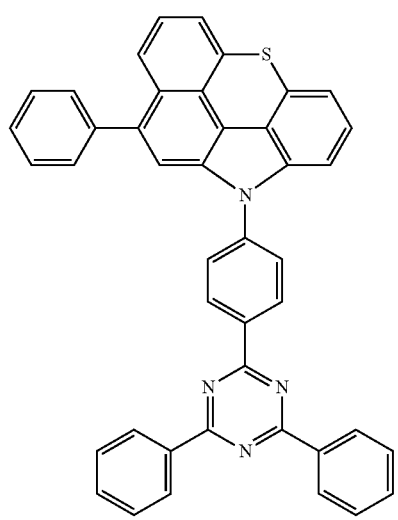
C-133
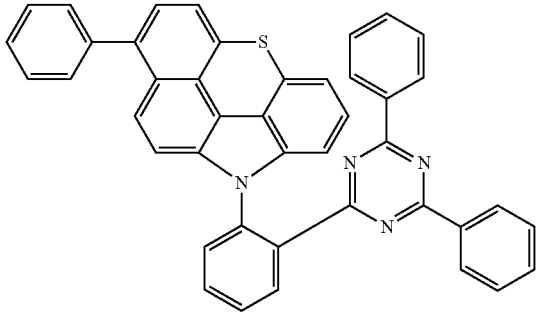
C-134
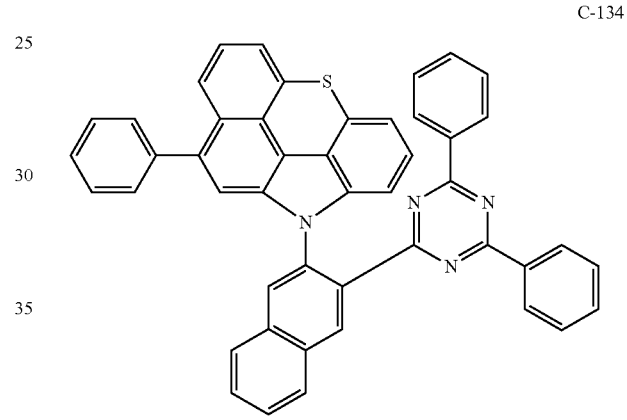
C-135
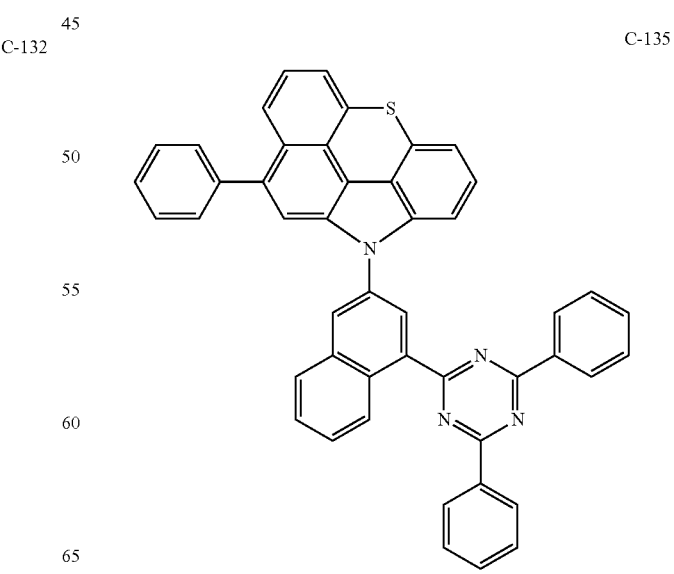

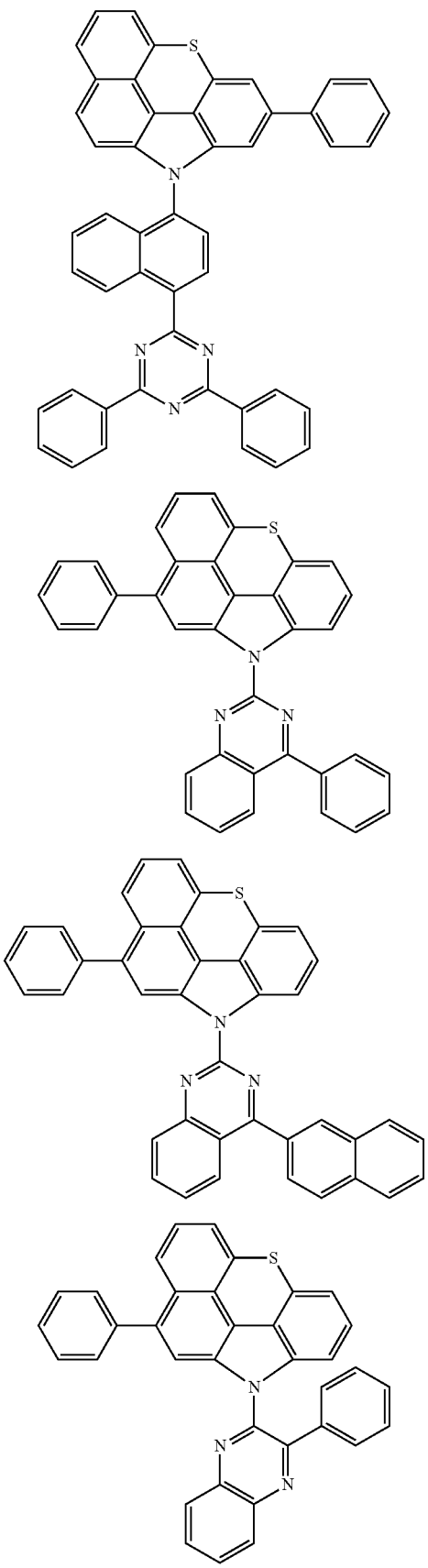
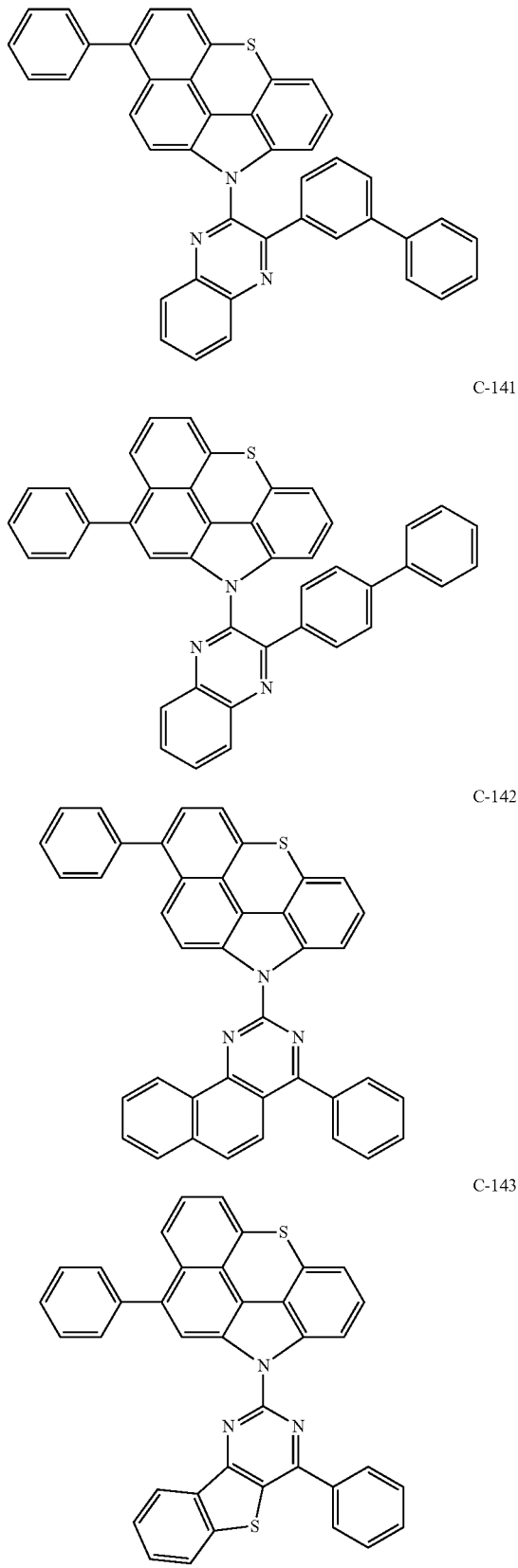

C-144
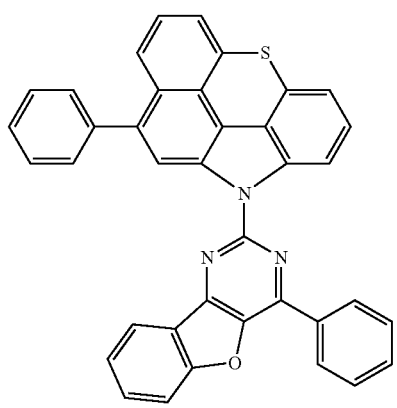
C-147
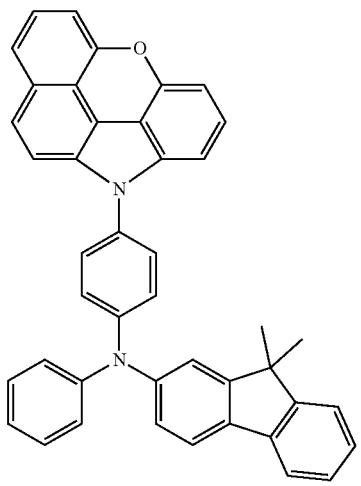
C-145
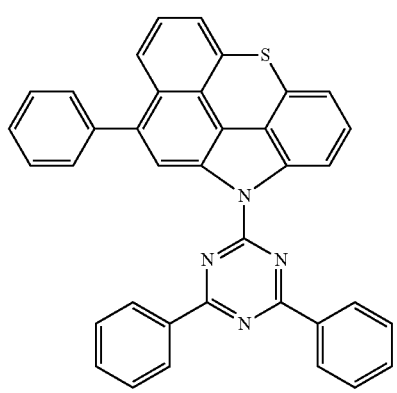
C-148
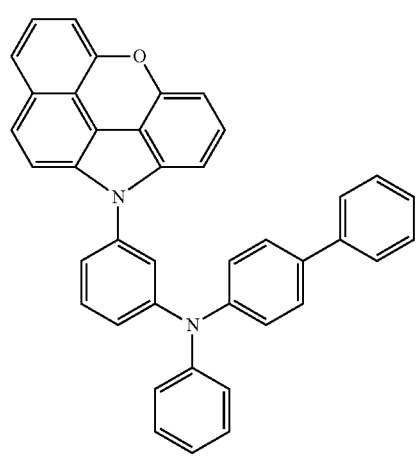
C-146
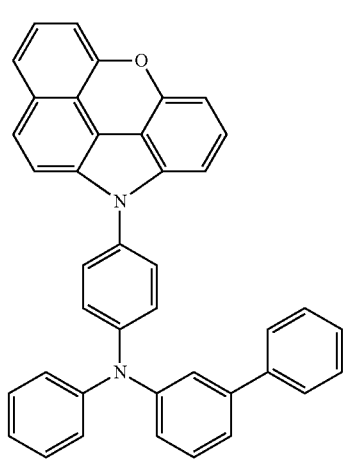
C-149
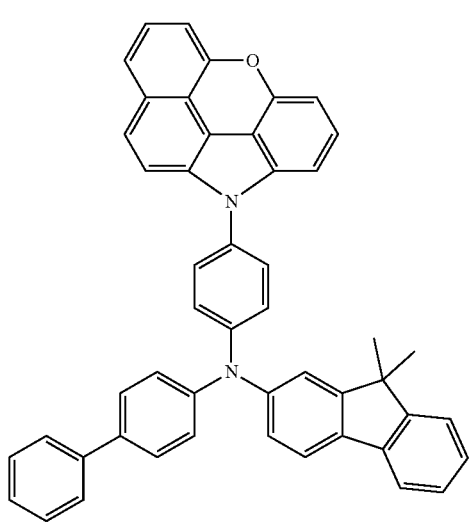

C-150 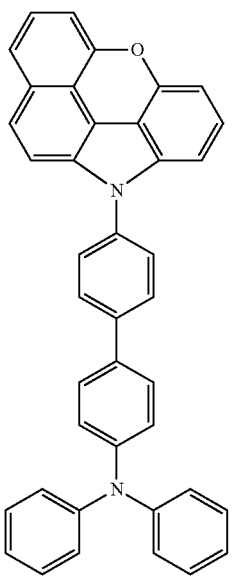
C-151 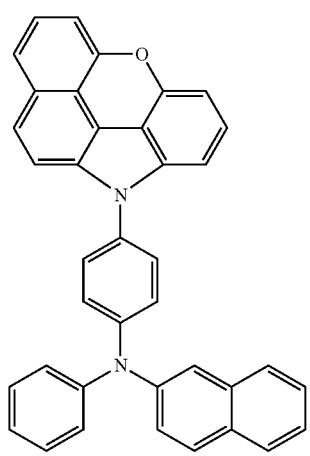
C-152 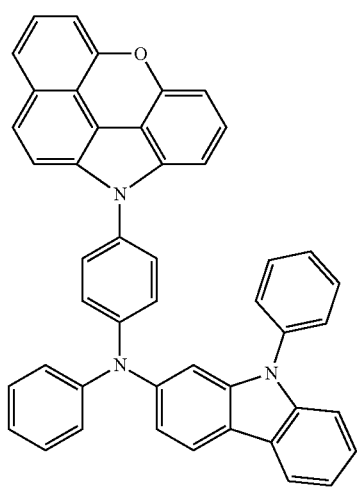
C-153 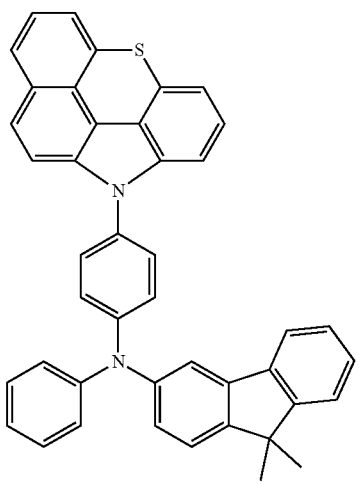
C-154 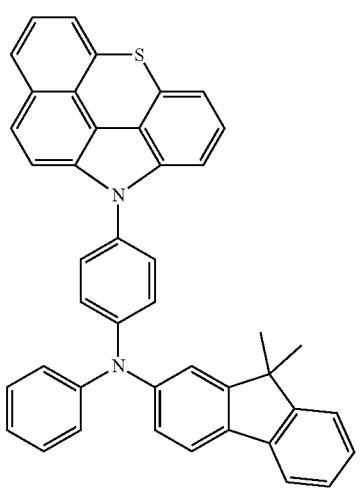
C-155 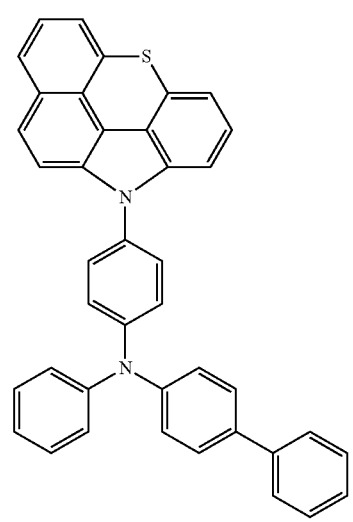

C-156
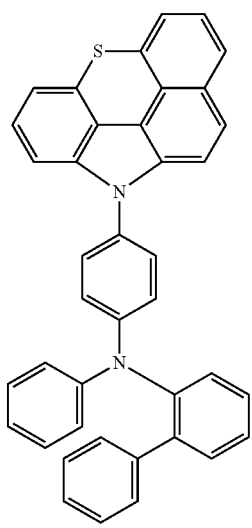
C-157
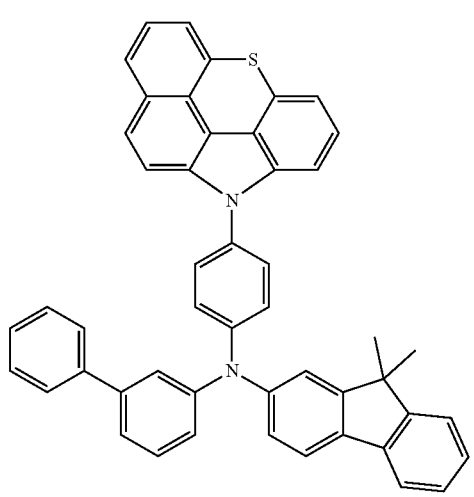
C-158
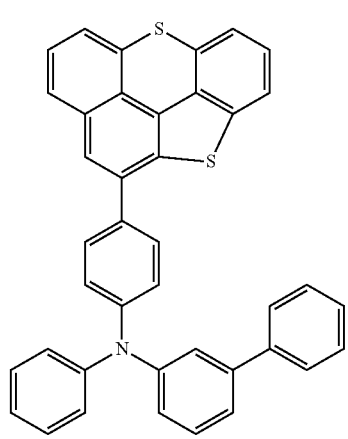
C-159
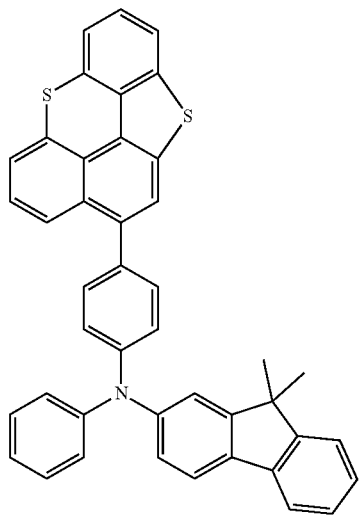
C-160
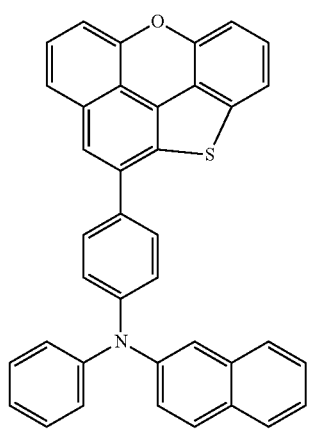
C-161

C-162
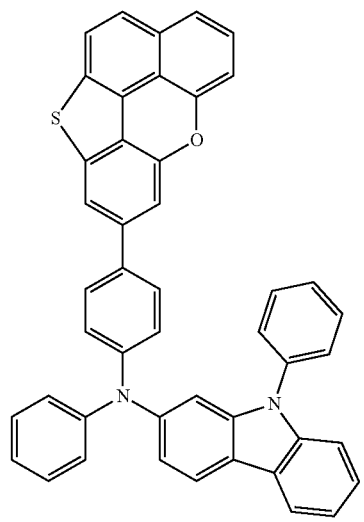
C-163
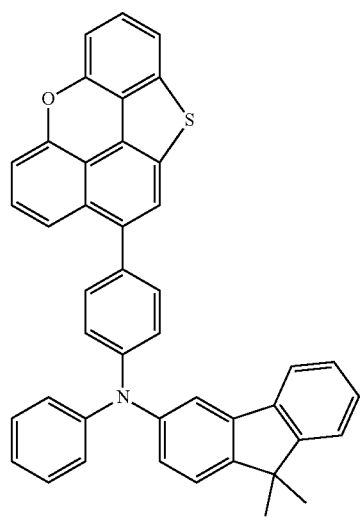
C-164
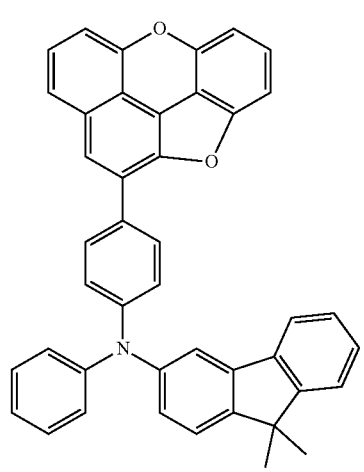
C-165
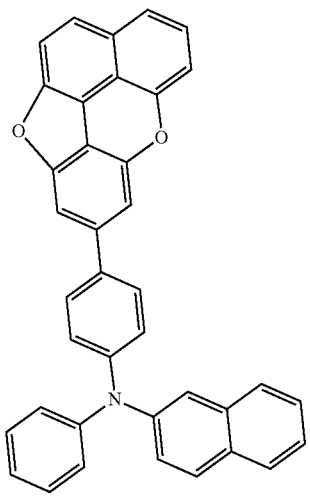
C-166
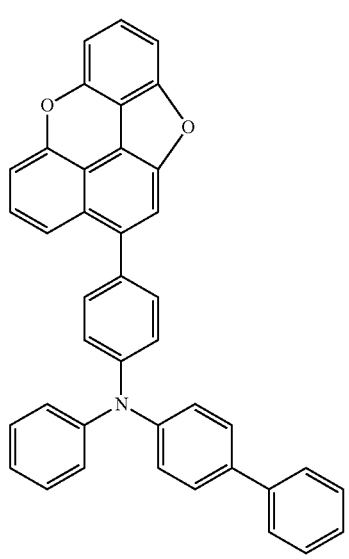
C-167
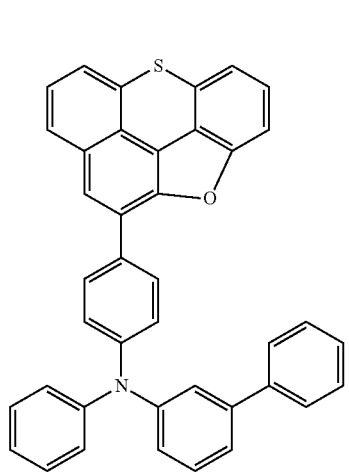

63
-continued
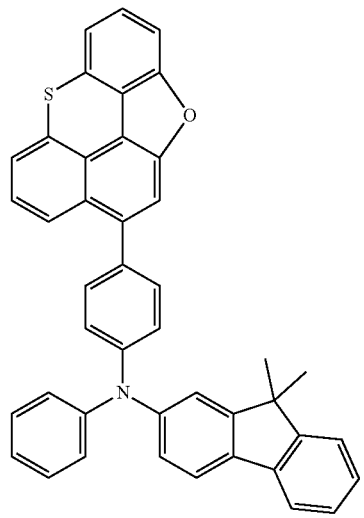
C-168
64
-continued
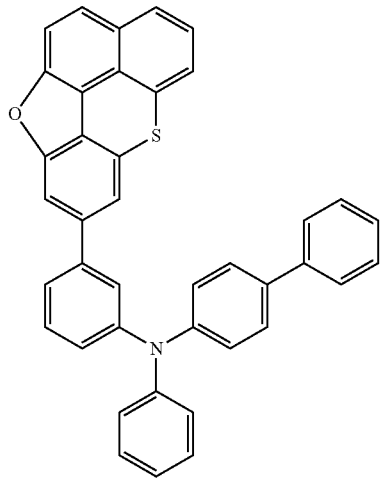
C-169
The organic electroluminescent compound represented by the formula 1 according to the present disclosure may be produced as represented by the following reaction schemes 1 to 8, but is not limited thereto; they may further be produced by a synthetic method known to a person skilled in the art.
[Reaction Scheme 1]
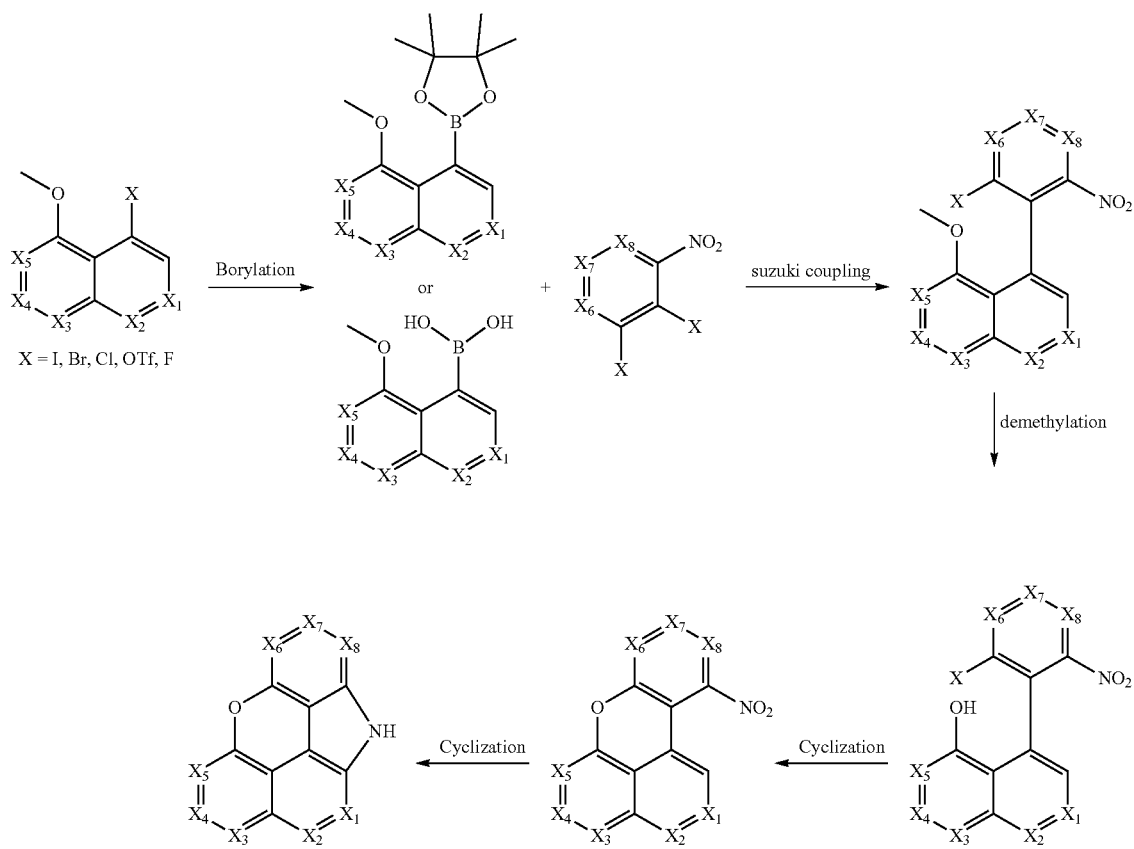

[Reaction Scheme 2]
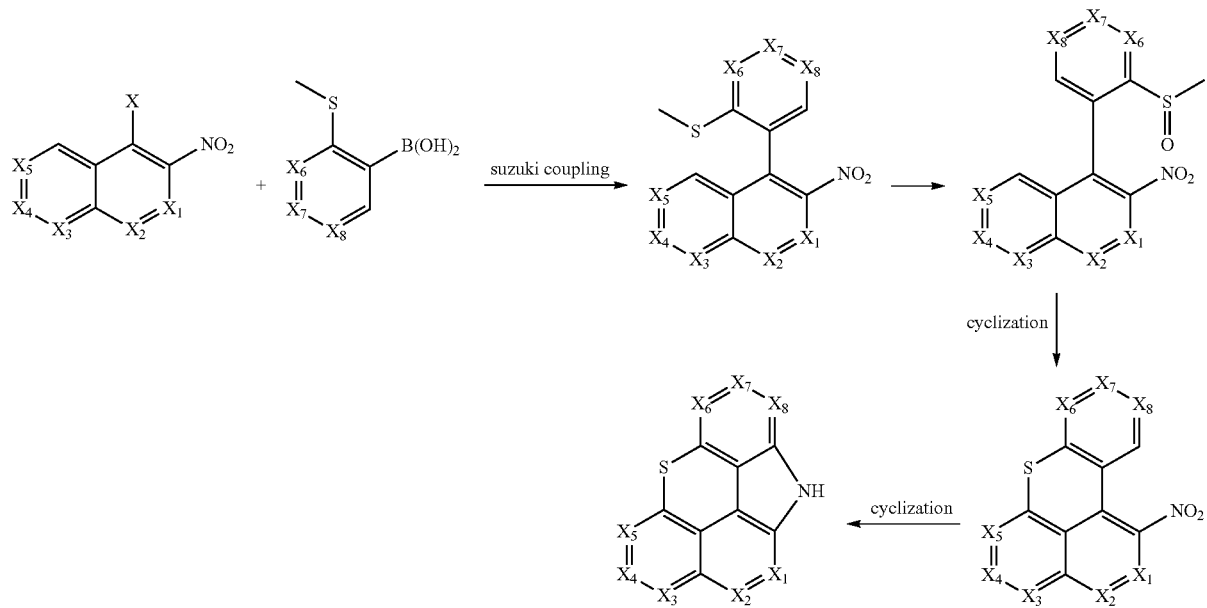
[Reaction Scheme 3]
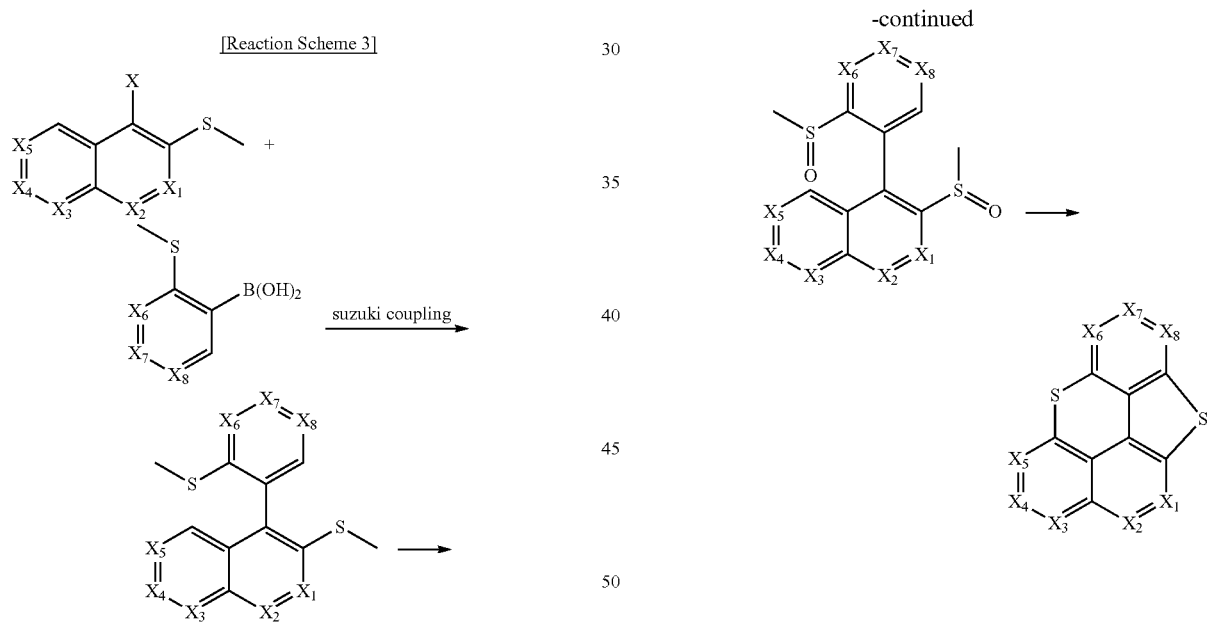
-continued
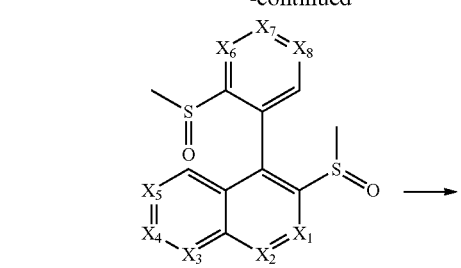
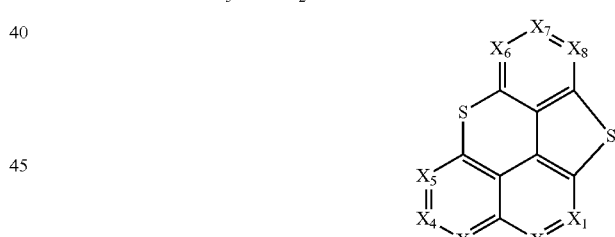
[Reaction Scheme 4]
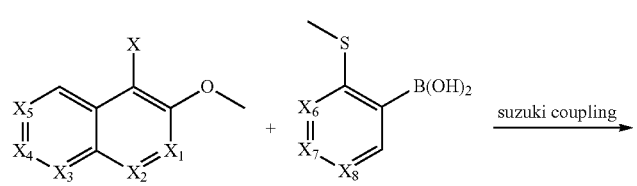
suzuki coupling

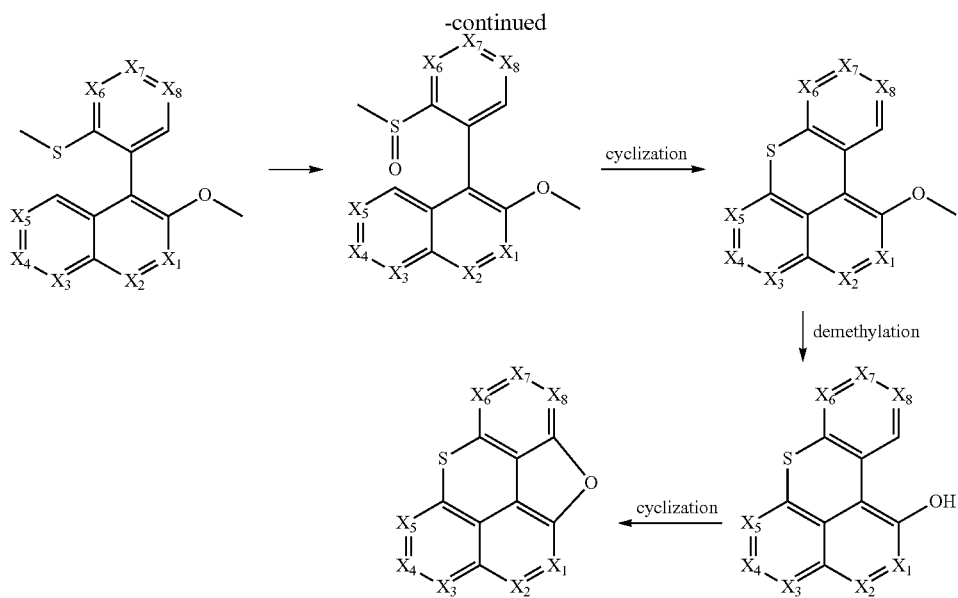
[Reation Scheme 5]
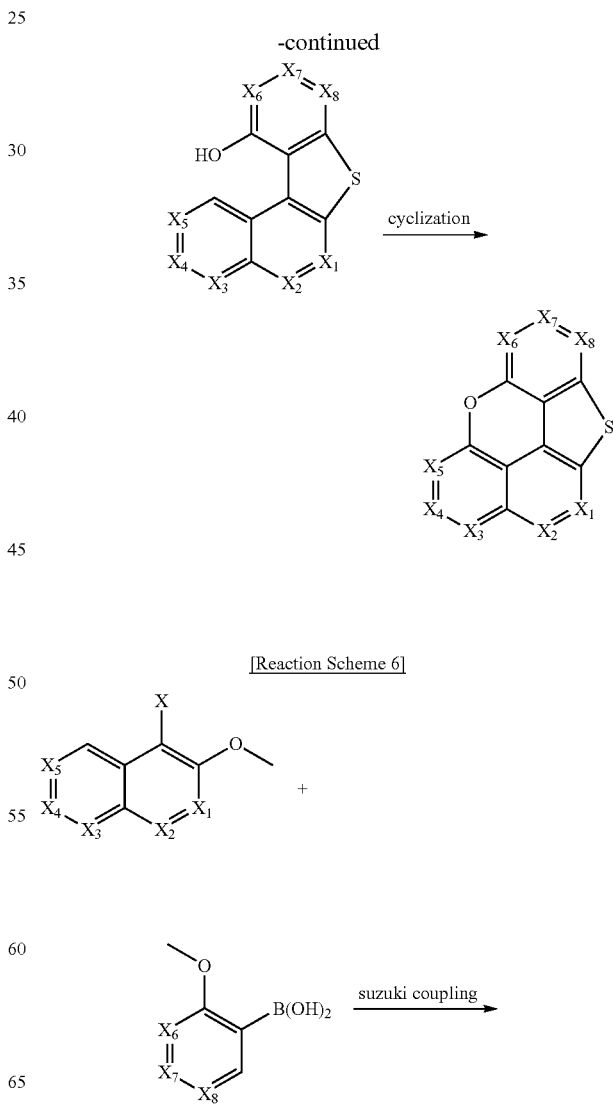
[Reaction Scheme 6]

-continued

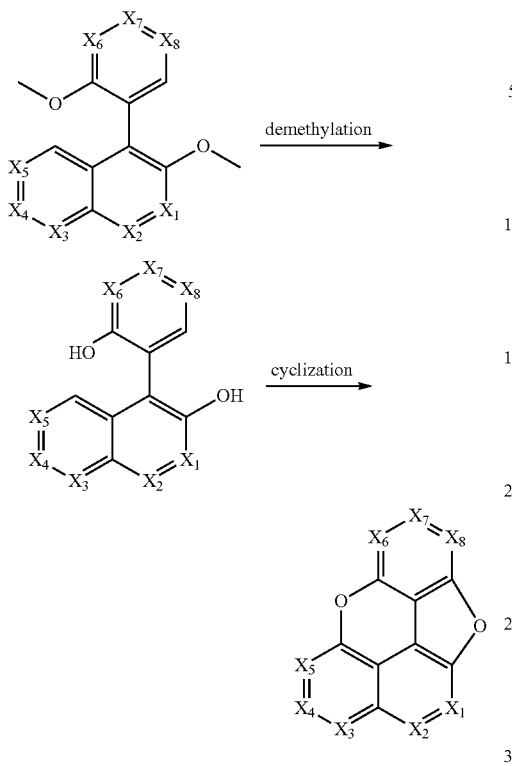

[Reaction Scheme 7]

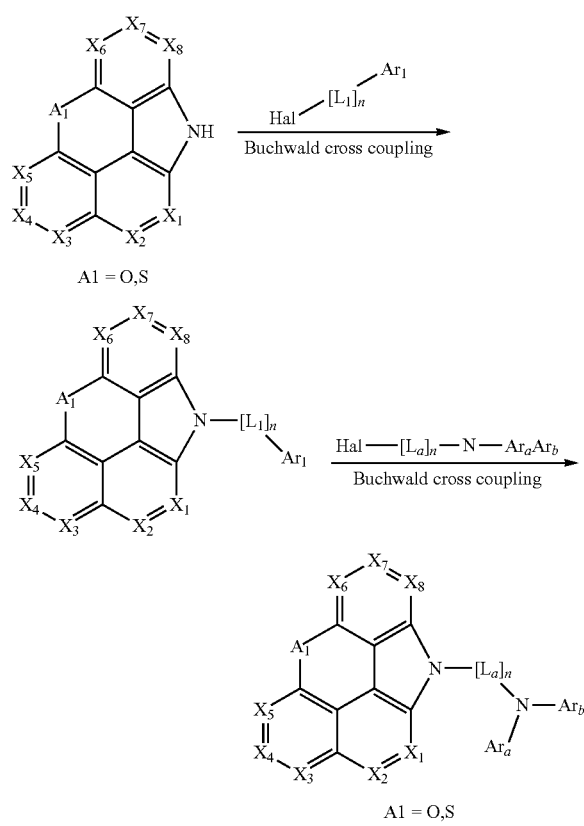

[Reaction Scheme 8]

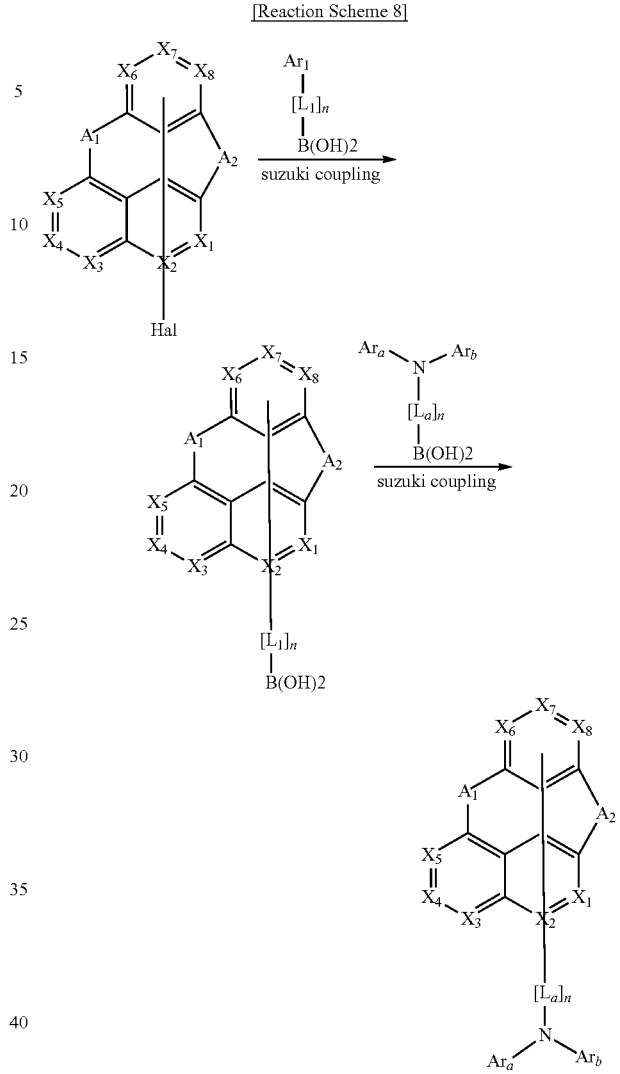

In reaction schemes 1 to 8 above, the definition of the substituents is as defined in formula 1 above, Hal represents a halogen atom, and n represents an integer of 1 or 2.

As described above, exemplary synthesis examples of the compounds represented by formula 1 according to one embodiment are described, but they are based on Suzuki cross-coupling reaction, Buchwald-Hartwig cross coupling reaction, N-arylation reaction, H-mont-mediated etherification reaction, Miyaura borylation reaction, Intramolecular acid-induced cyclization reaction, Pd(II)-catalyzed oxidative cyclization reaction, Grignard reaction, Heck reaction, Cyclic Dehydration reaction, $SN_1$ substitution reaction, $SN_2$ substitution reaction, and Phosphine-mediated reductive cyclization reaction, etc. It will be understood by one skilled in the art that the above reaction proceeds even if other substituents defined in the formula 1 other than the substituents described in the specific synthesis examples are bonded.

The present disclosure may provide an organic electroluminescent material comprising an organic electroluminescent compound of formula 1, and an organic electroluminescent device comprising the organic electroluminescent material.

The organic electroluminescent material may be comprised solely of the organic electroluminescent compound of the present disclosure, or may further comprise conventional materials included in the organic electroluminescent material. When two or more species of materials are included in one layer, the at least two compounds may be a mixture-evaporation or a co-evaporation to form a layer. The organic electroluminescent material according to one embodiment may comprise at least one compound represented by formula 1 above. For example, the compound of formula 1 may be included in a light-emitting layer, if the compound of formula 1 is included in the light-emitting layer, the compound of formula 1 may be included as a host, more specifically as a phosphorescent red host.

The organic electroluminescent material of the present disclosure may further include at least one host compound other than the organic electroluminescent compound of formula 1 above. Preferably, the organic electroluminescent material may further include at least one dopant.

The dopant comprised in the organic electroluminescent material of the present disclosure may be at least one phosphorescent or fluorescent dopant, preferably a phosphorescent dopant. The phosphorescent dopant material applied to the organic electroluminescent device of the present disclosure is not particularly limited, but may be preferably a metallated complex compound(s) of a metal atom(s) selected from iridium (Ir), osmium (Os), copper (Cu), and platinum (Pt), as necessary, more preferably an ortho-metallated complex compound(s) of a metal atom(s) selected from iridium (Ir), osmium (Os), copper (Cu), and platinum (Pt), as necessary, and even more preferably ortho-metallated iridium complex compound(s), as necessary.

The dopant comprised may use the compound represented by the following formula 101, but is not limited thereto:

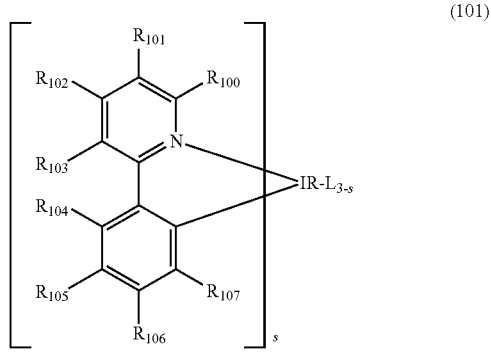

(101)

In formula 101, L is selected from the following structure 1 or 2;

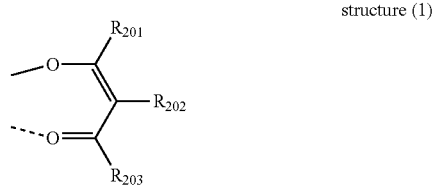

structure (1)

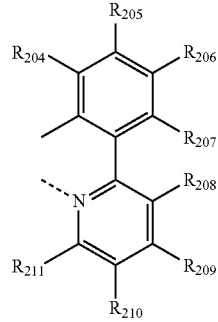

structure (2)

in structures 1 and 2, $R_{100}$ to $R_{103}$ each independently represent, hydrogen, deuterium, halogen, (C1-C30)alkyl unsubstituted or substituted with halogen, a substituted or unsubstituted (C3-C30)cycloalkyl, a substituted or unsubstituted (C6-C30)aryl, cyano, a substituted or unsubstituted (C3-C30) heteroaryl, or a substituted or unsubstituted (C1-C30)alkoxy; or may be linked to the adjacent substituent to form a ring(s), e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline, together with pyridine;

$R_{104}$ to $R_{107}$ each independently represent, hydrogen, deuterium, halogen, (C1-C30)alkyl unsubstituted or substituted with halogen, a substituted or unsubstituted (C3-C30)cycloalkyl, a substituted or unsubstituted (C6-C30)aryl, a substituted or unsubstituted (C3-C30) heteroaryl, cyano, or a substituted or unsubstituted (C1-C30)alkoxy; or may be linked to the adjacent substituent to form a ring(s), e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine, together with benzene;

$R_{201}$ to $R_{211}$ each independently represent, hydrogen, deuterium, halogen, (C1-C30)alkyl unsubstituted or substituted with halogen, a substituted or unsubstituted (C3-C30)cycloalkyl, or a substituted or unsubstituted (C6-C30)aryl; or may be linked to the adjacent substituent to form a ring(s); and s represents an integer of 1 to 3.

Specifically, the specific examples of the dopant compound include the following, but are not limited thereto.

D-1 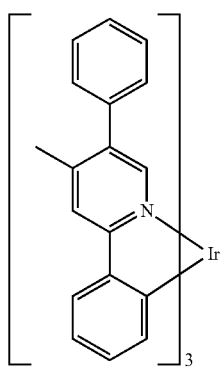
D-2 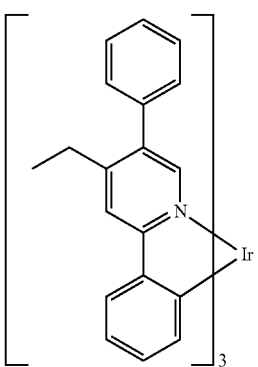
D-3 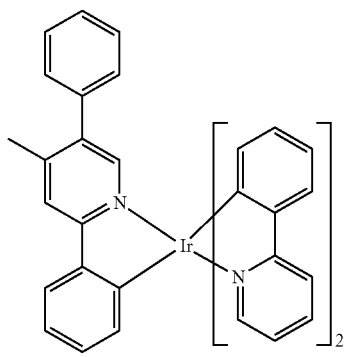
D-4 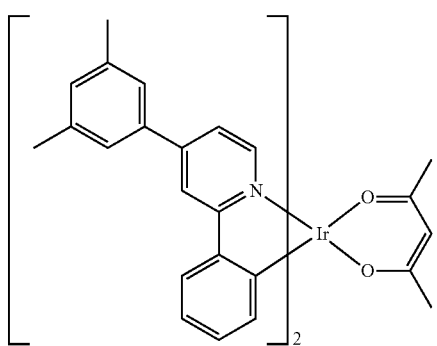
-continued
D-5 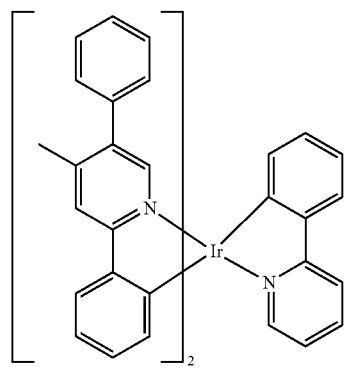
D-6 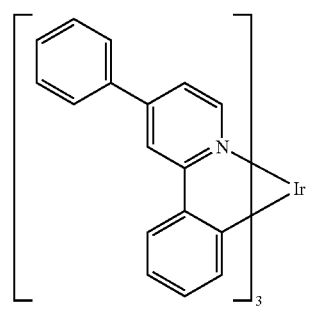
D-7 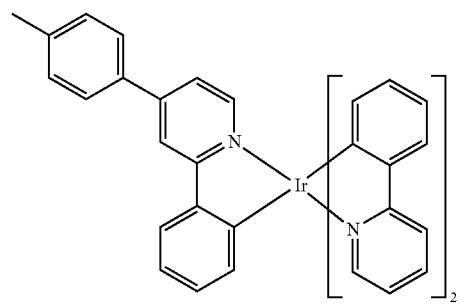
D-8 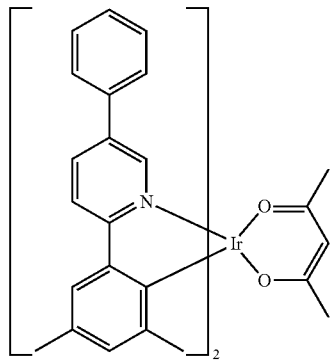

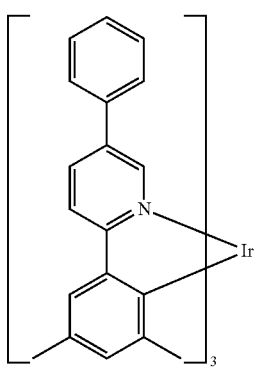
D-9
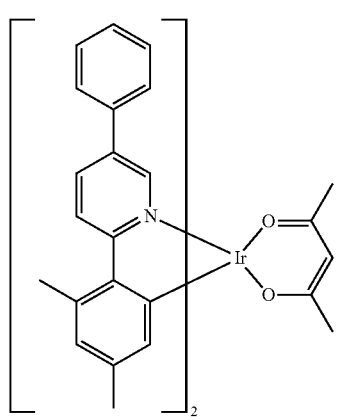
D-10
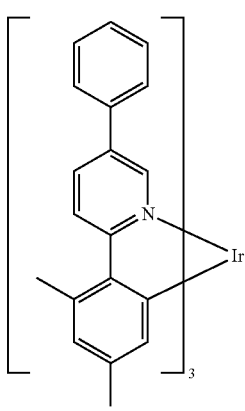
D-11
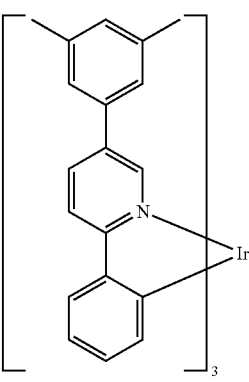
D-12
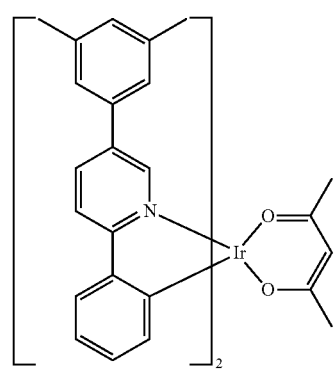
D-13
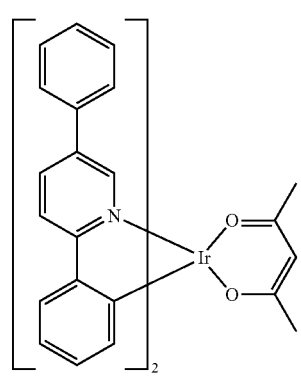
D-14
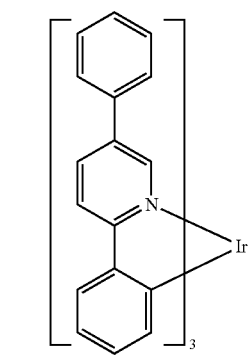
D-15
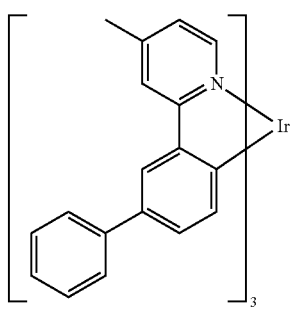
D-16

D-17
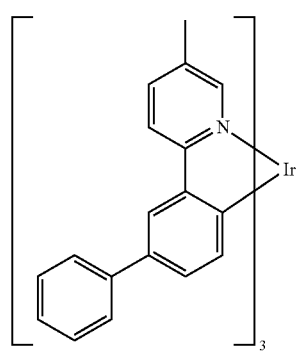
D-18
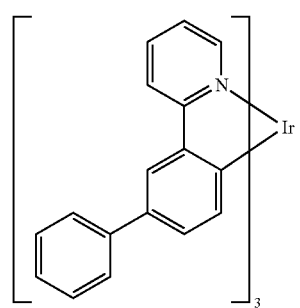
D-19
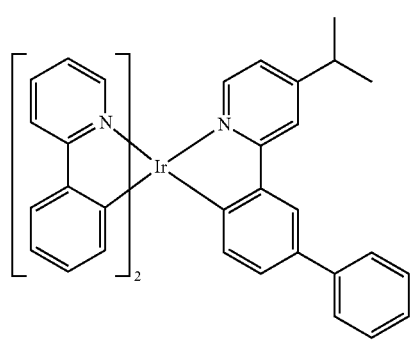
D-20
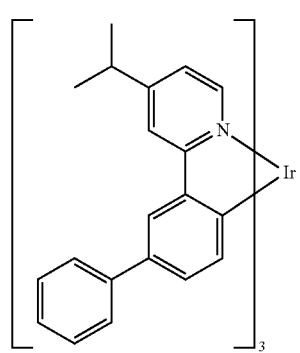
D-21
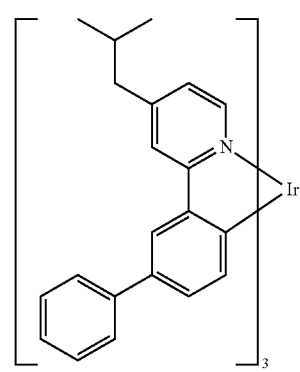
D-22
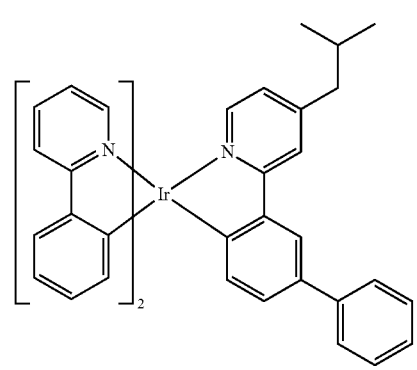
D-23
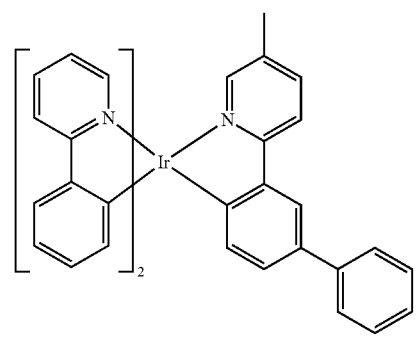
D-24
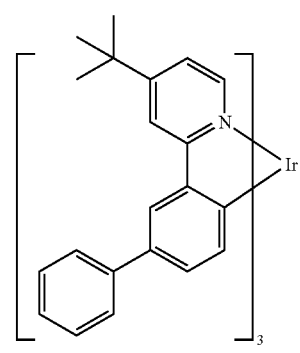

D-25
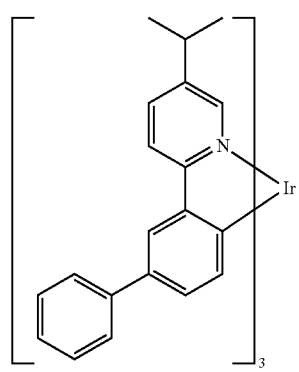
D-26
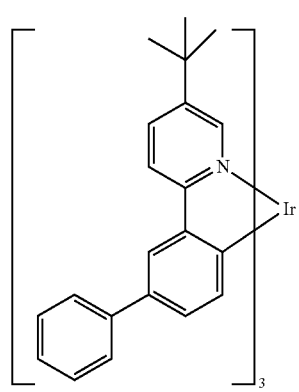
D-27
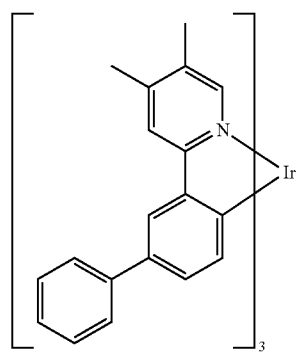
D-28
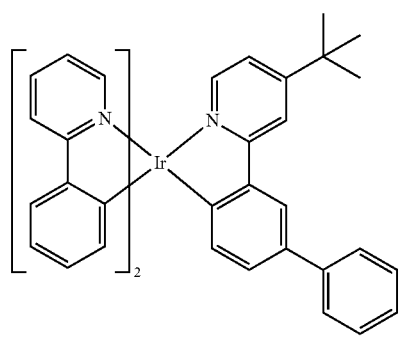
D-29
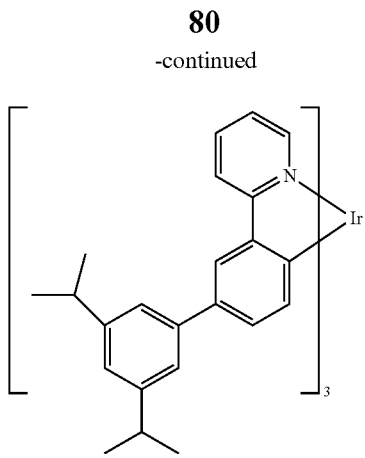
D-30
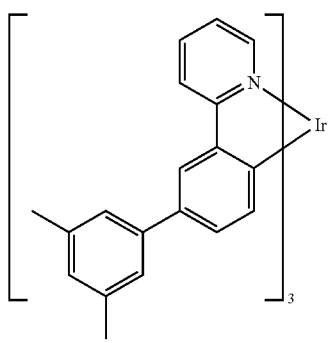
D-31
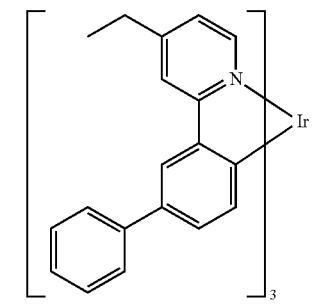
D-32
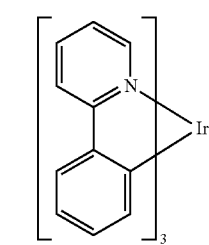
D-33
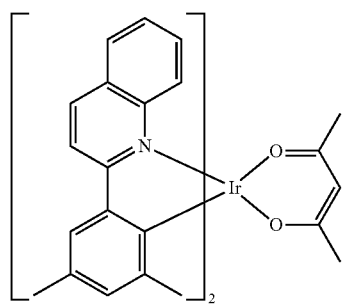

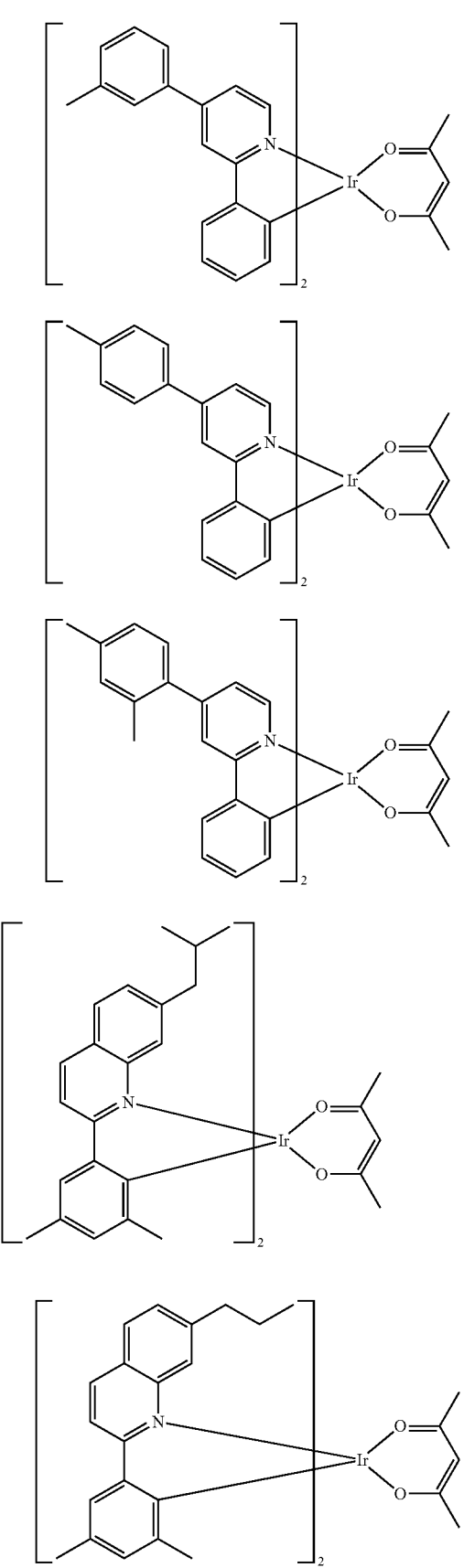
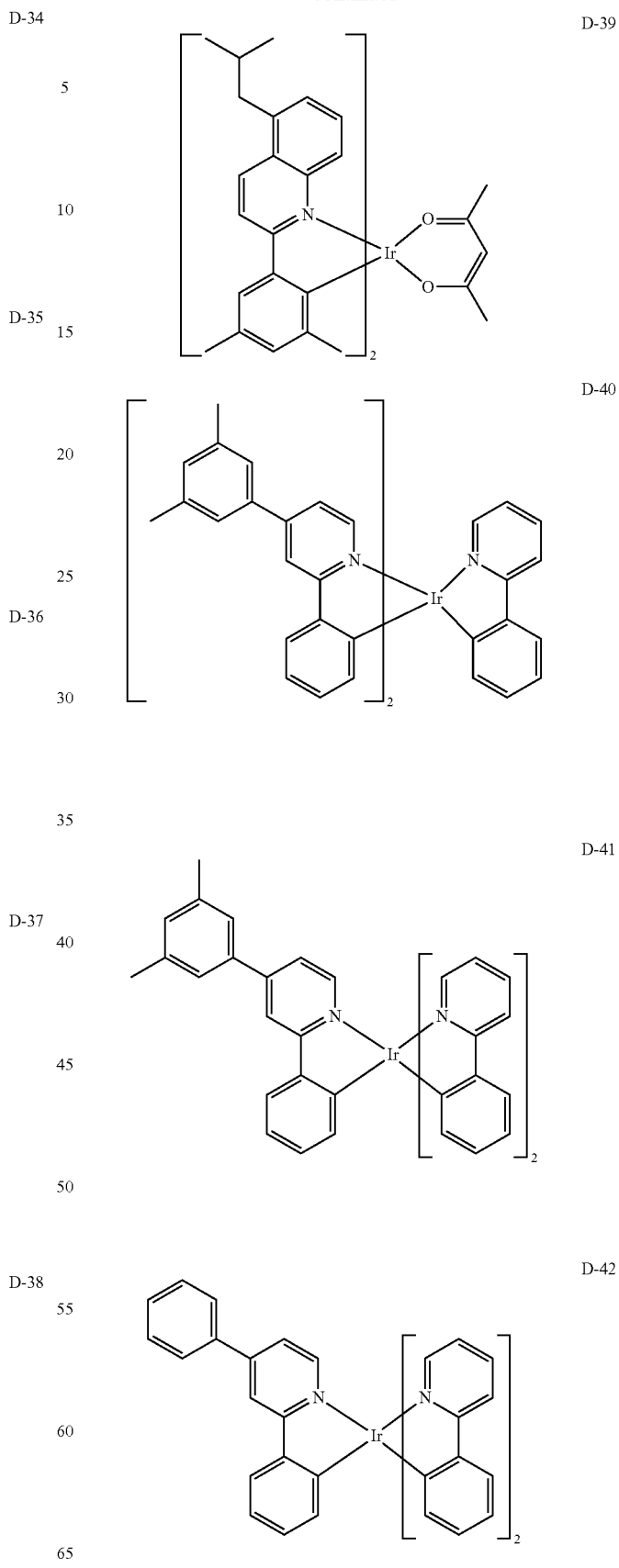

D-43
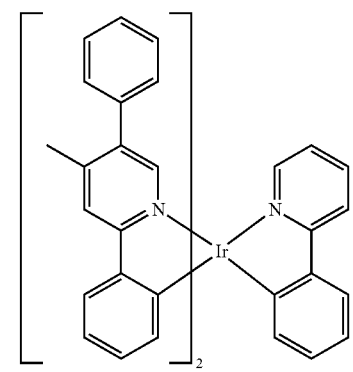
D-44
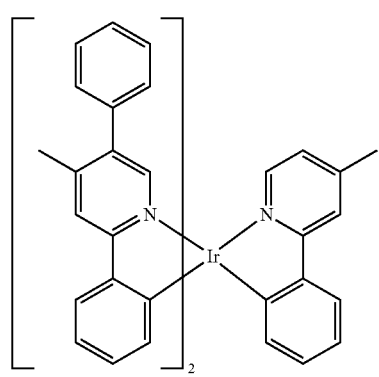
D-45
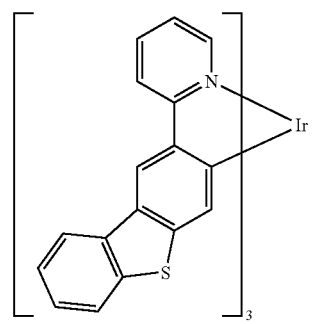
D-46
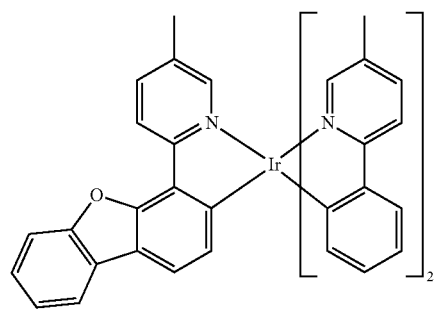
D-47
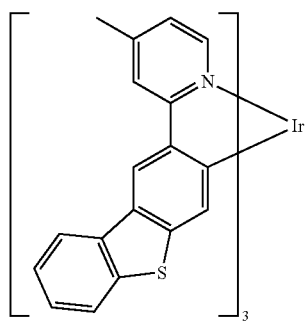
D-48
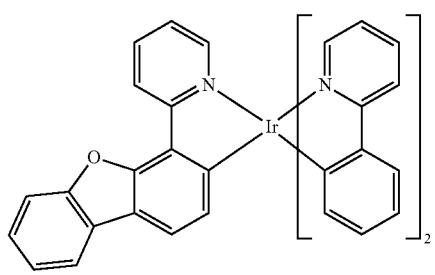
D-49
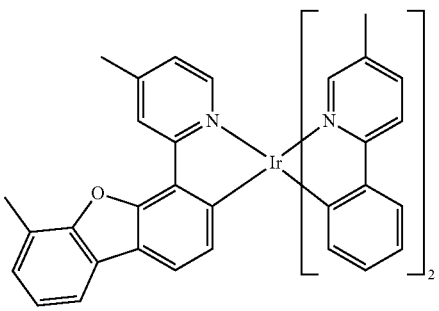
D-50
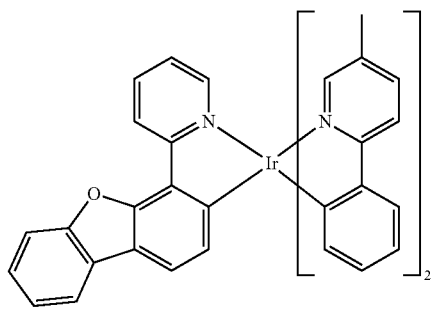
D-51
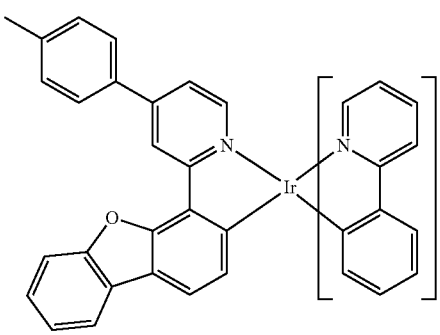

D-52 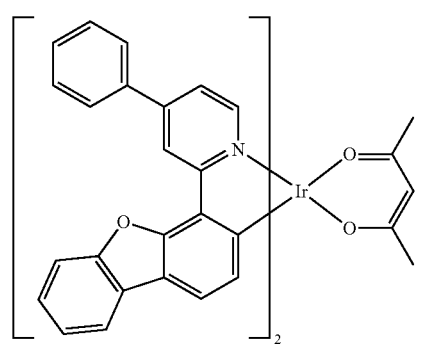
D-53 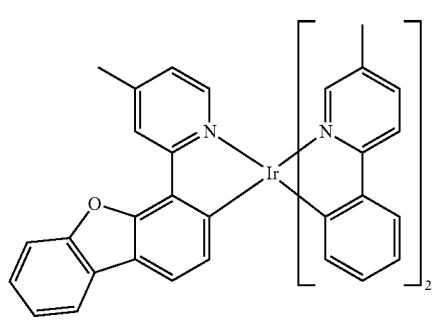
D-54 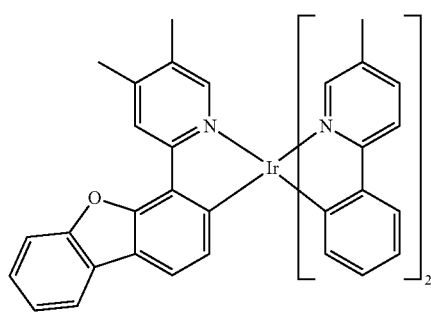
D-55 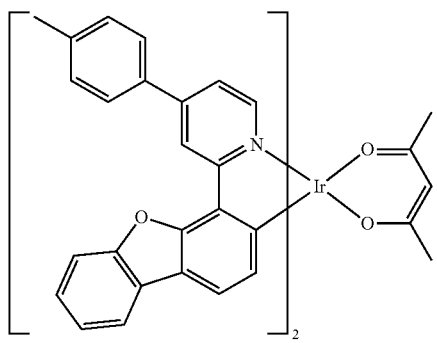
D-56 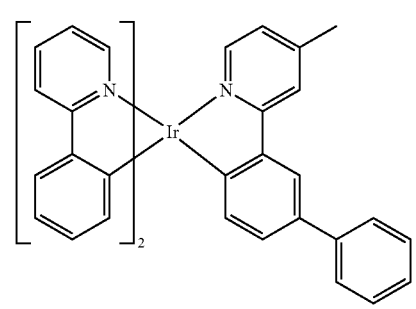
D-57 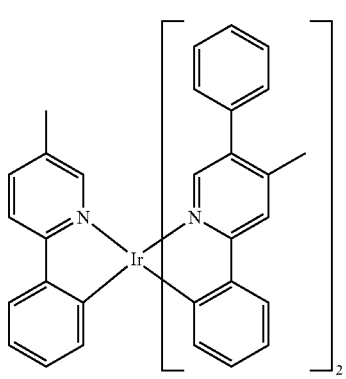
D-58 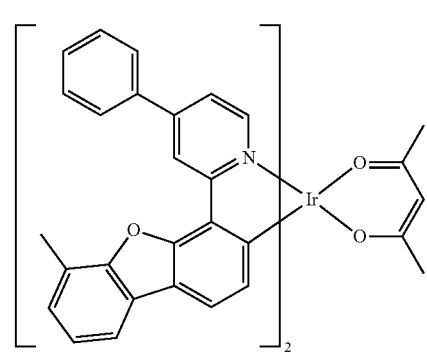
D-59 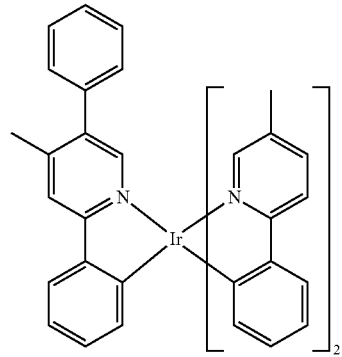
D-60 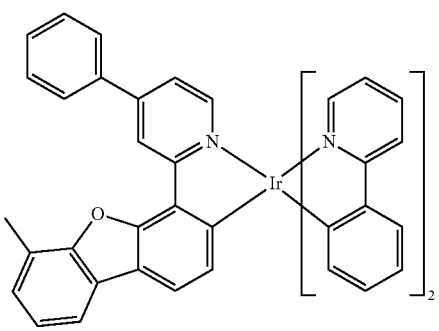

D-61
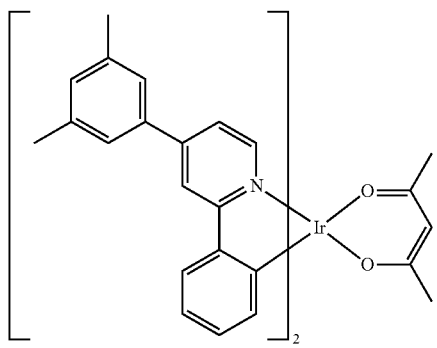
D-62
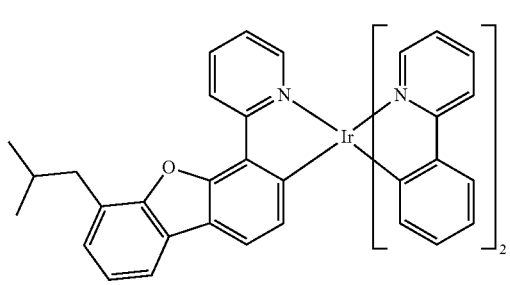
D-63
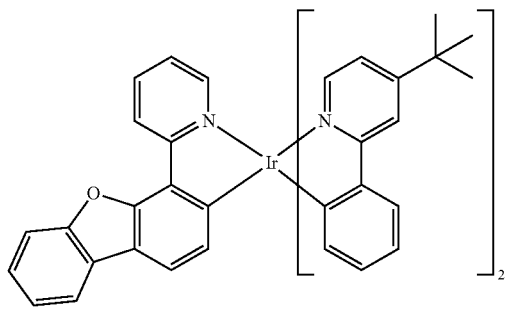
D-64
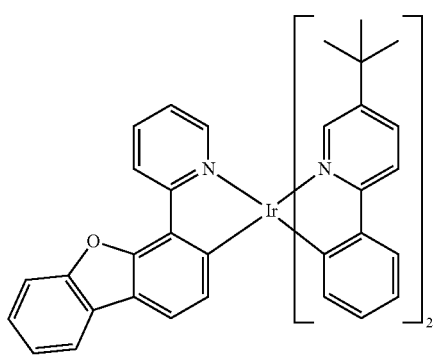
D-65
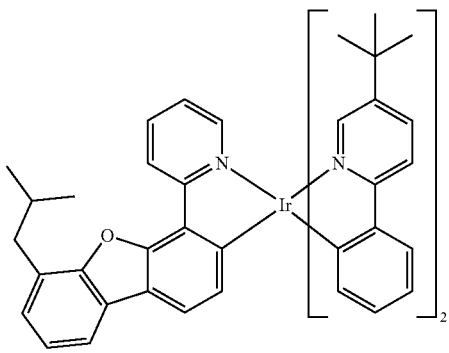
D-66
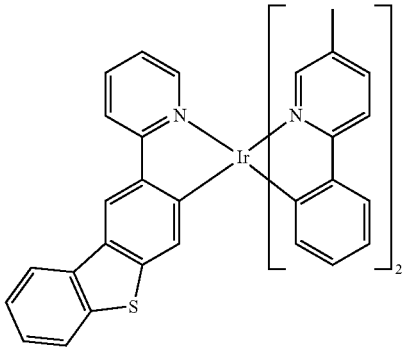
D-67
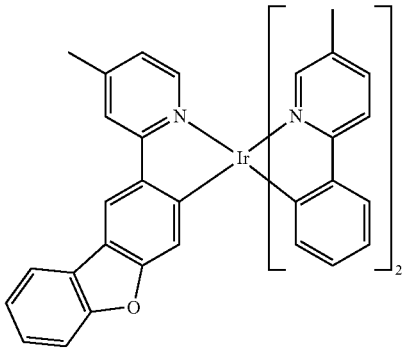
D-68
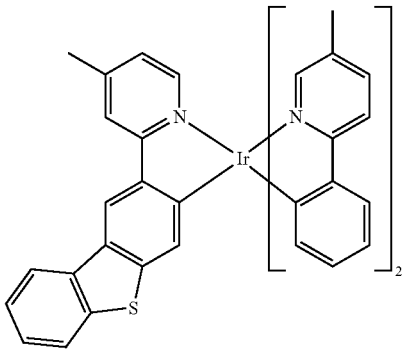

D-69
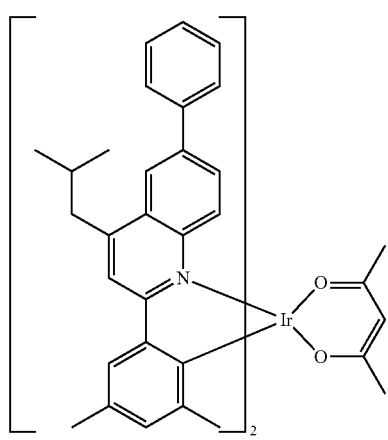
D-70
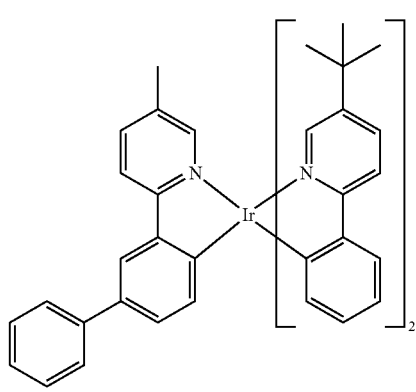
D-71
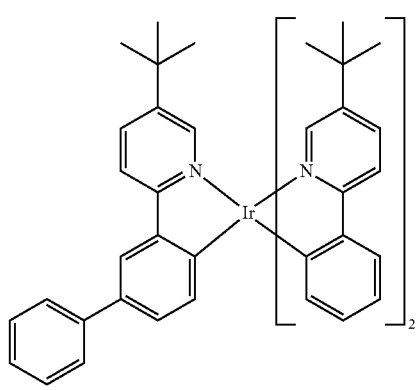
D-72
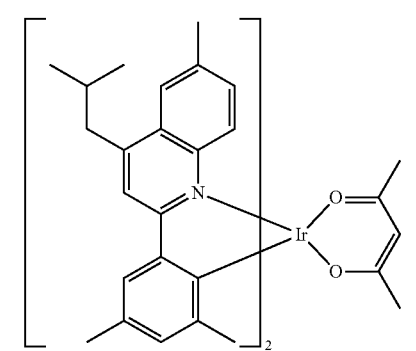
D-73
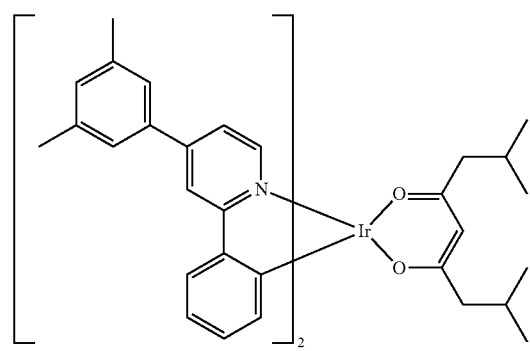
D-74
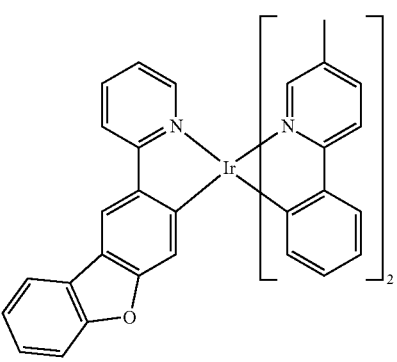
D-75
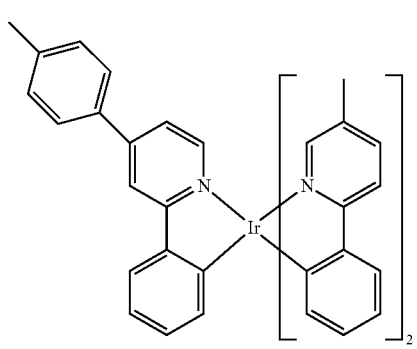
D-76
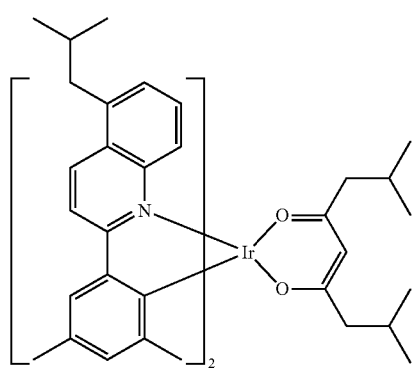

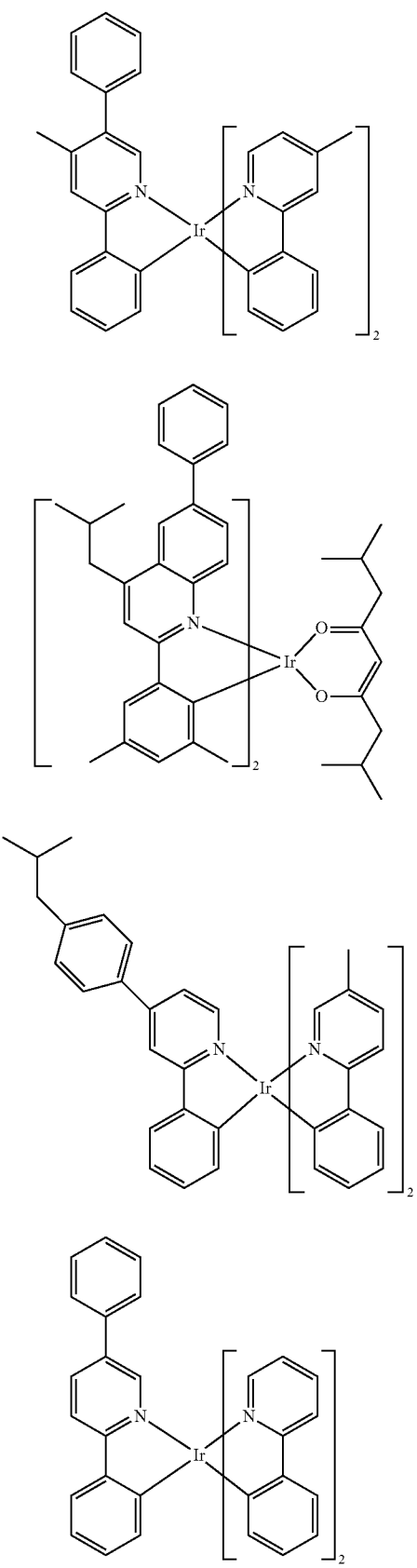
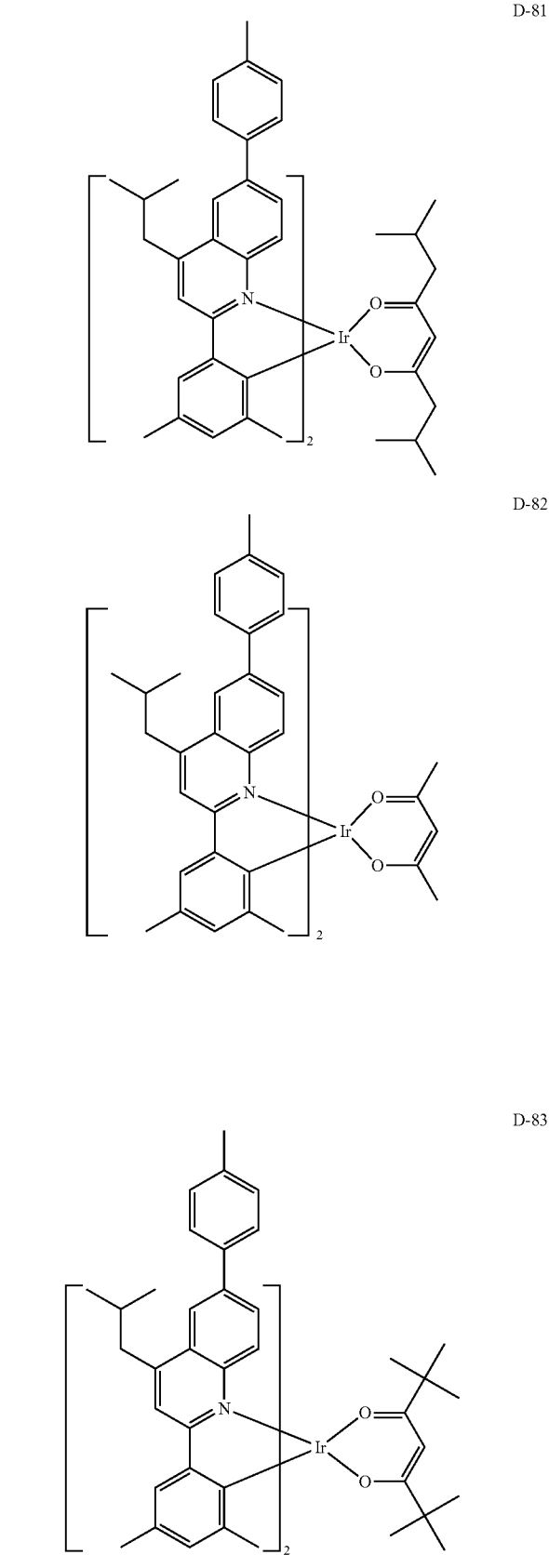

-continued
D-84
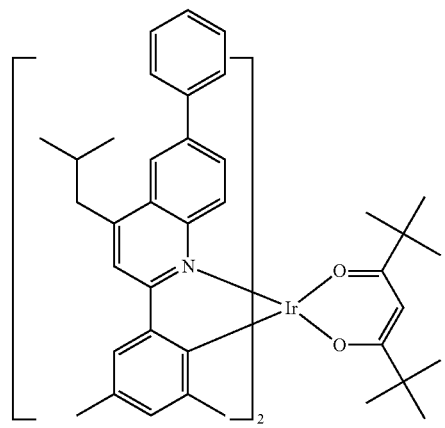
D-85
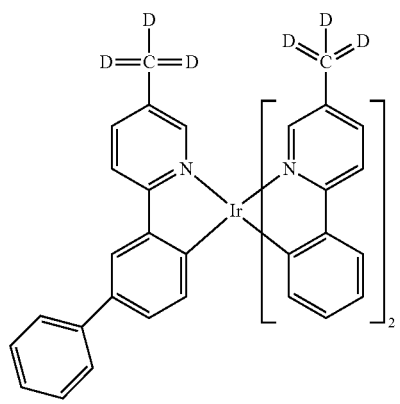
D-86
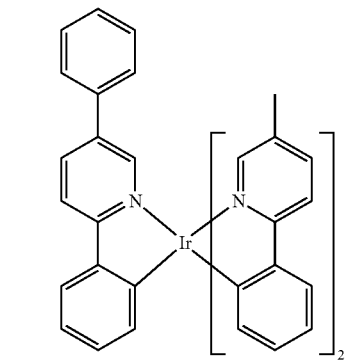
D-87
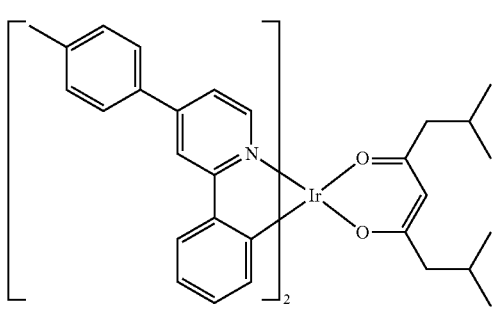
-continued
D-88
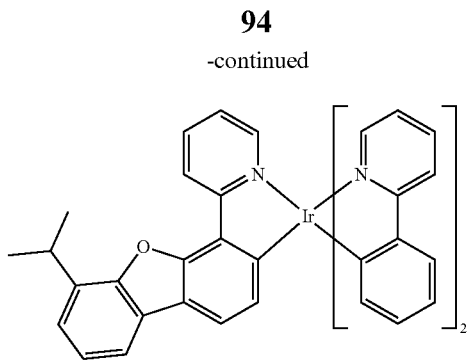
D-89
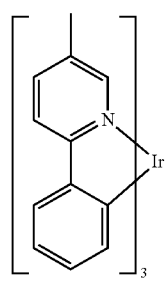
D-90
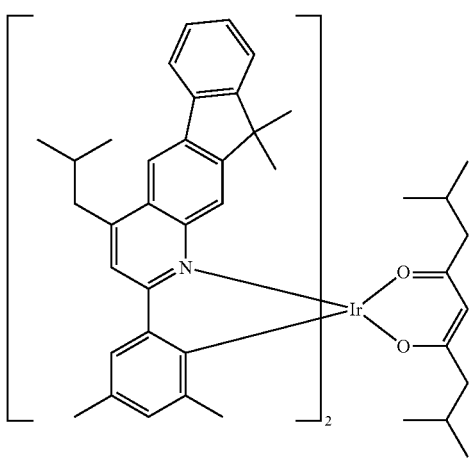
D-91
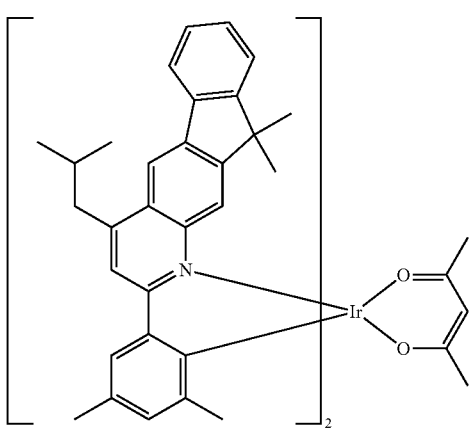

-continued
D-92
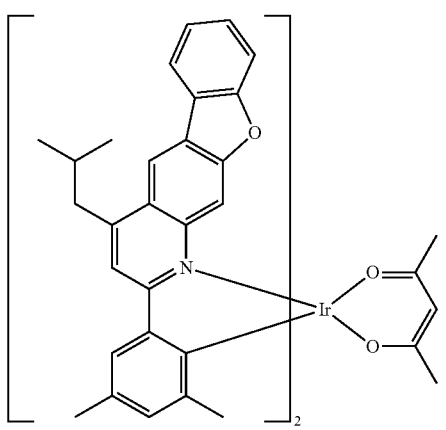
D-93
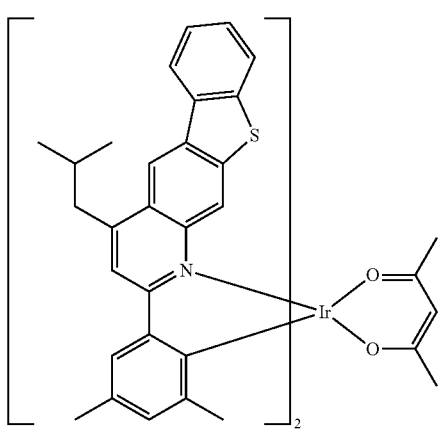
D-94
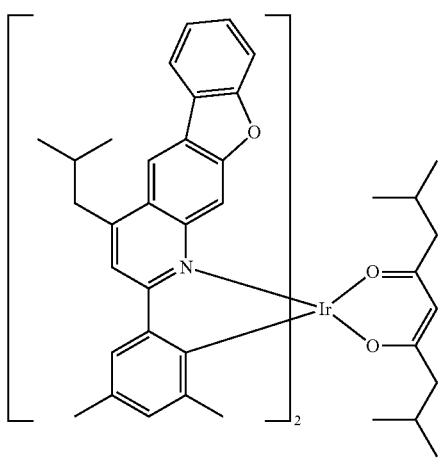
-continued
D-95
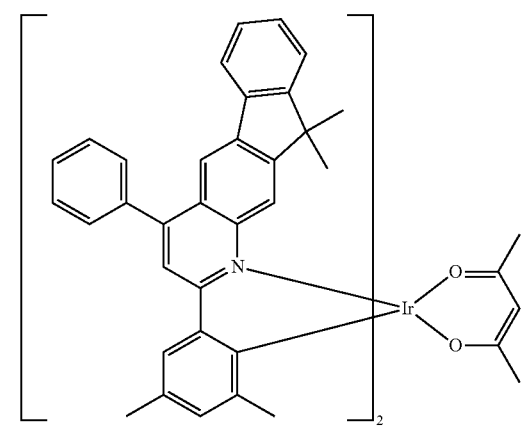
D-96
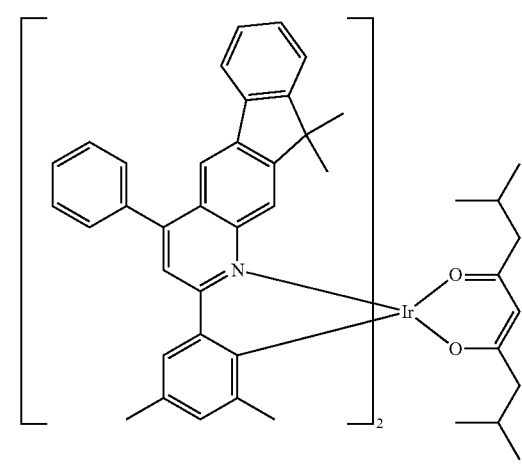
D-97
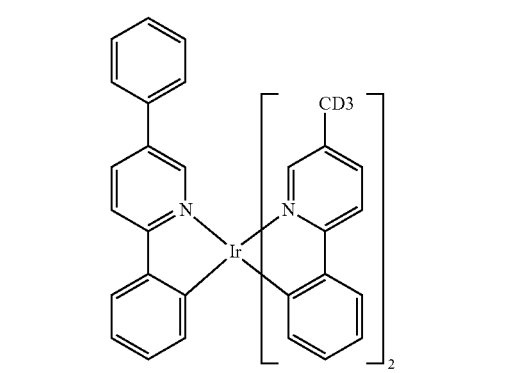
D-98
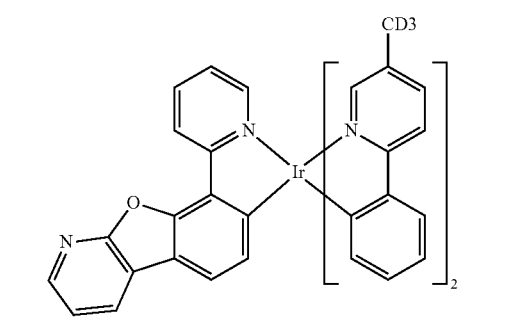

D-99
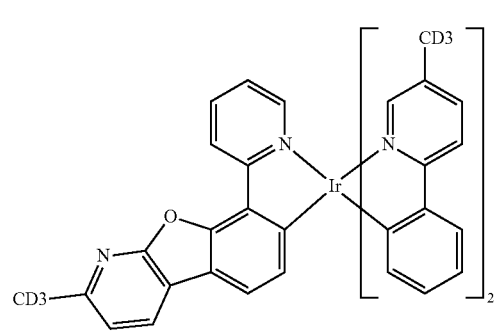
D-100
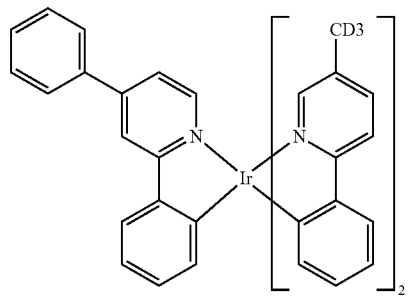
D-101
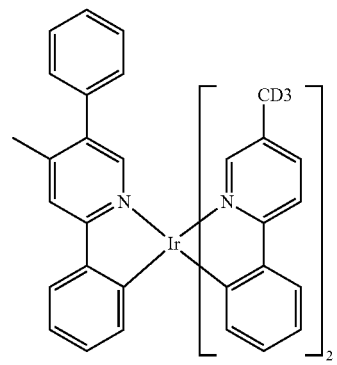
D-102
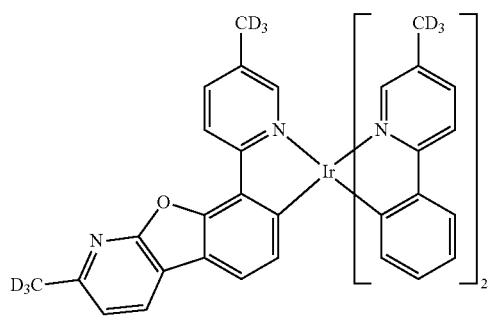
D-103
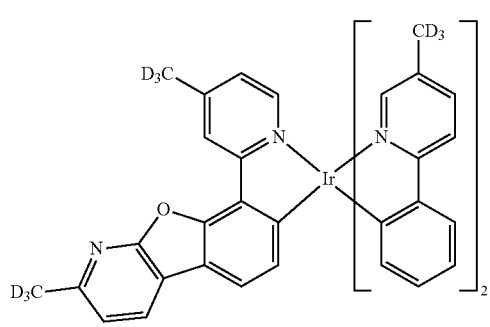
D-104
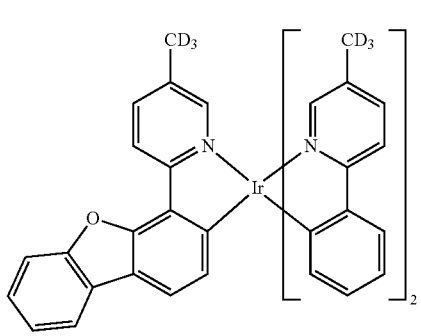
D-105
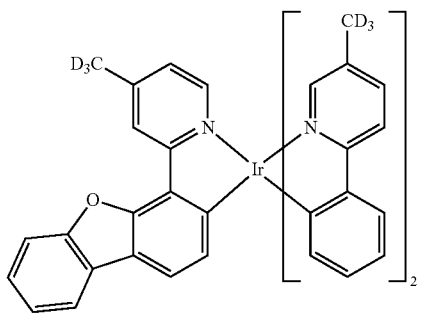
D-106
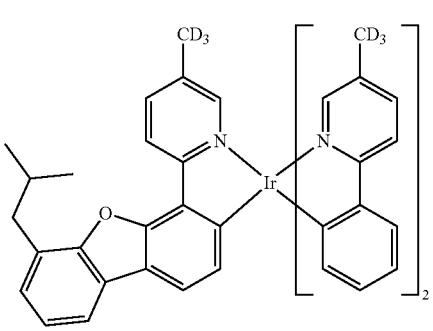
D-107
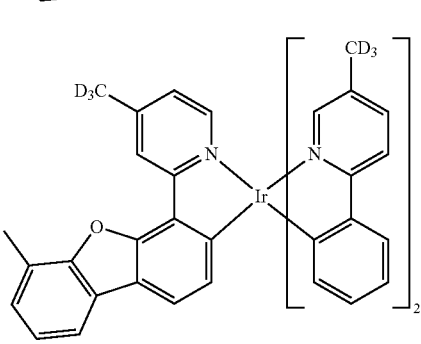
D-108
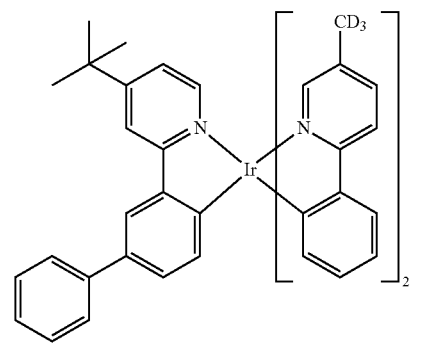

D-109

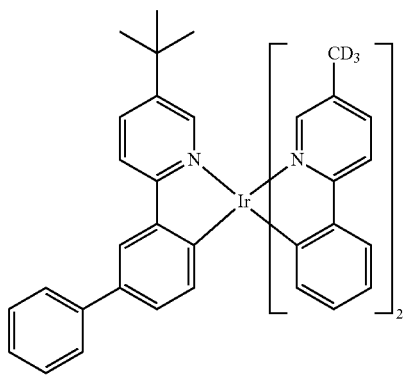

D-110

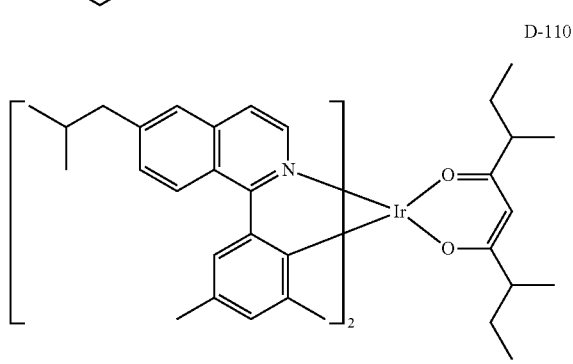

D-111

D-112

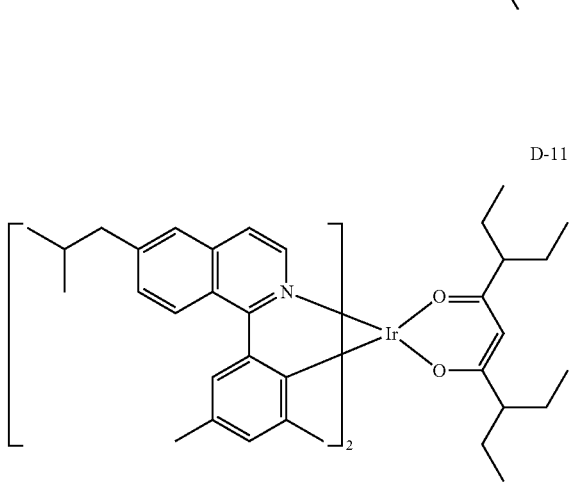

D-113

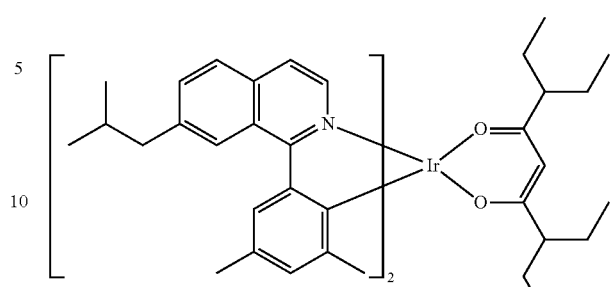

D-114

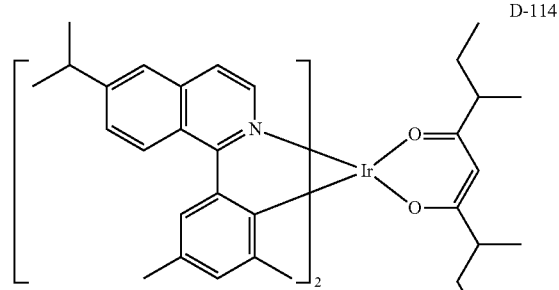

D-115

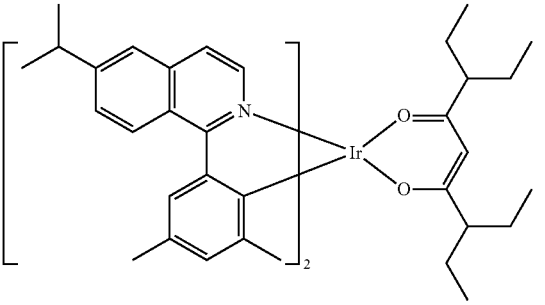

Hereinafter, the organic electroluminescent device to which the aforementioned organic electroluminescent compound or the organic electroluminescent material is applied will be described.

The organic electroluminescent device according to one embodiment may comprise a first electrode; a second electrode; and at least one organic layer between the first and second electrodes.

The compound represented by formula 1 of the present disclosure may be included in one or more layers constituting the organic electroluminescent device. According to one embodiment, the organic layer includes a light-emitting layer containing an organic electroluminescent compound according to the present disclosure. For example, the light-emitting layer may include solely of the organic electroluminescent compound of the present disclosure or at least two species of the organic electroluminescent compound of the present disclosure, and may further comprise conventional materials included in the organic electroluminescent material.

In addition, the organic layer may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer in addition to the light-emitting layer. Each layer may further consist of several layers. Also, the organic layer may further comprise at least one compound(s) selected from the group consisting of an arylamine-based compound and a styrylarylamine-based compound, and further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising such a metal.

An organic electroluminescent material according to one embodiment may be used as light-emitting materials for a white organic light-emitting device. The white organic light-emitting device has suggested various structures such as a parallel side-by-side arrangement method, a stacking arrangement method, or color conversion material (CCM) method, etc., according to the arrangement of R (Red), G (Green), YG (yellowish green), or B (blue) light-emitting units. In addition, the organic electroluminescent material according to one embodiment may also be applied to the organic electroluminescent device comprising a QD (quantum dot).

One of the first electrode and the second electrode may be an anode and the other may be a cathode. Wherein, the first electrode and the second electrode may each be formed as a transmissive conductive material, a transflective conductive material, or a reflective conductive material. The organic electroluminescent device may be a top emission type, a bottom emission type, or a both-sides emission type according to the kinds of the material forming the first electrode and the second electrode.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole injection layer may be doped as a p-dopant. Also, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, and wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each layer may use a plurality of compounds. Also, the electron injection layer may be doped as an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as the hole auxiliary layer or the electron blocking layer. The light-emitting auxiliary layer, the hole auxiliary layer, or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a halogenated metal layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a halogenated metal layer or a metal oxide layer is preferably placed on a cathode surface of an electroluminescent medium layer. The operation stability for the organic electroluminescent device may be obtained by the surface layer. Preferably, the chalcogenide includes $SiO_X$ (1≤X≤2), $AlO_X$ (1≤X≤1.5), SiON, SiAlON, etc.; the halogenated metal includes LiF, $MgF_2$, $CaF_2$, a rare earth metal fluoride, etc.; and the metal oxide includes $Cs_2O$, $Li_2O$, MgO, SrO, BaO, CaO, etc.

Further, in the organic electroluminescent device of the present disclosure, preferably, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used.

When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

When forming a layer by the host compound and the dopant compound according to one embodiment, co-evaporation or mixture-evaporation may be used, but are not limited thereto. The co-deposition is a mixed deposition method in which two or more isomer materials are put into respective individual crucible sources and a current is applied to both cells simultaneously to evaporate the materials and to perform mixed deposition; and the mixed deposition is a mixed deposition method in which two or more isomer materials are mixed in one crucible source before deposition, and then a current is applied to one cell to evaporate the materials.

According to one embodiment, the organic electroluminescent device of the present disclosure can be used for the manufacture of display devices such as smartphones, tablets, notebooks, PCs, TVs, or display devices for vehicles, or lighting devices such as outdoor or indoor lighting.

Hereinafter, the preparation method of compounds according to the present disclosure will be explained with reference to the synthesis method of a representative compound or the intermediate compound of the present disclosure in order to understand the present disclosure in detail.

[Example 1] Synthesis of Compound C-1

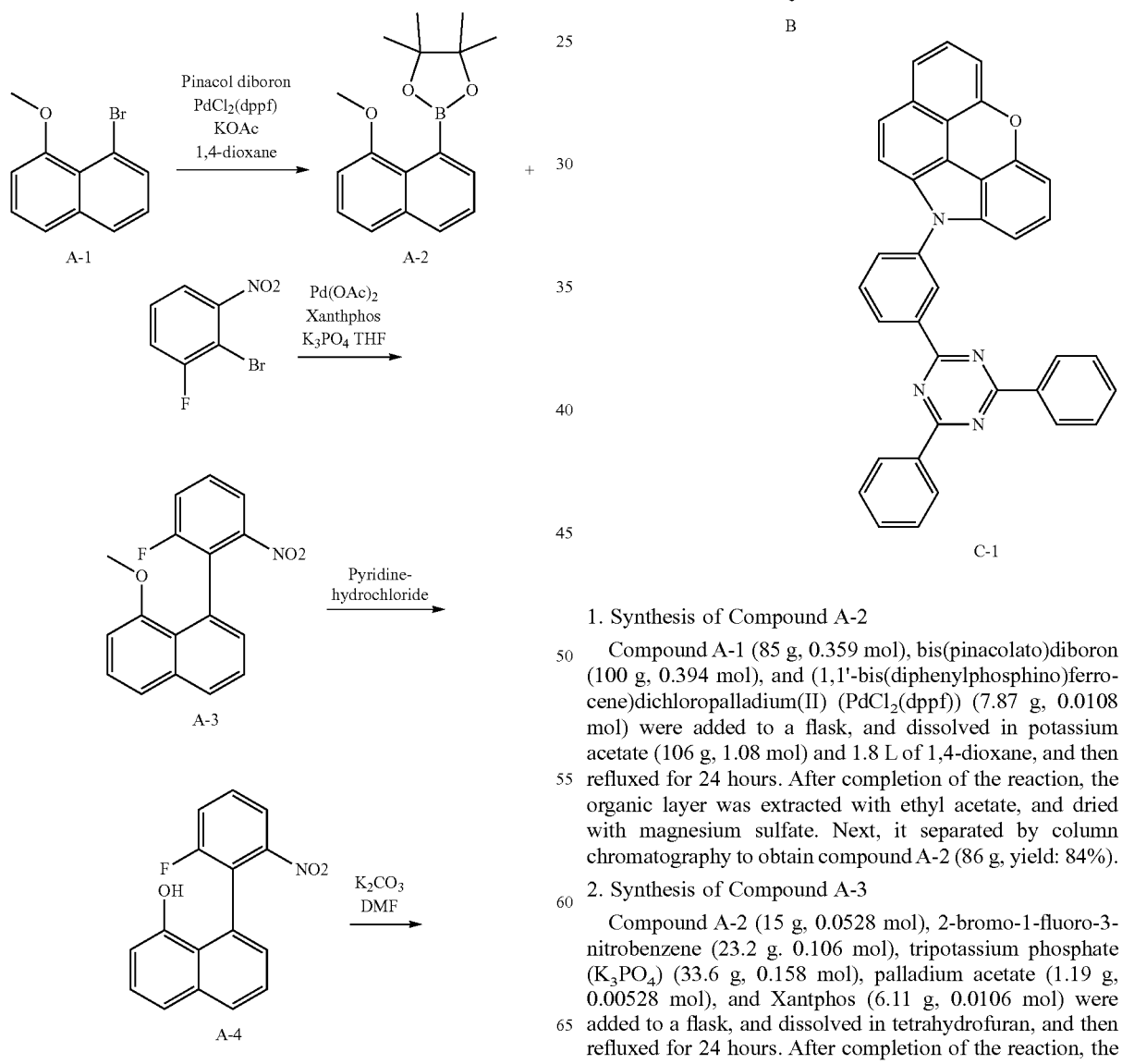

1. Synthesis of Compound A-2

Compound A-1 (85 g, 0.359 mol), bis(pinacolato)diboron (100 g, 0.394 mol), and (1,1'-bis(diphenylphosphino)ferrocene)dichloropalladium(II) (PdCl$_2$(dppf)) (7.87 g, 0.0108 mol) were added to a flask, and dissolved in potassium acetate (106 g, 1.08 mol) and 1.8 L of 1,4-dioxane, and then refluxed for 24 hours. After completion of the reaction, the organic layer was extracted with ethyl acetate, and dried with magnesium sulfate. Next, it separated by column chromatography to obtain compound A-2 (86 g, yield: 84%).

2. Synthesis of Compound A-3

Compound A-2 (15 g, 0.0528 mol), 2-bromo-1-fluoro-3-nitrobenzene (23.2 g, 0.106 mol), tripotassium phosphate (K$_3$PO$_4$) (33.6 g, 0.158 mol), palladium acetate (1.19 g, 0.00528 mol), and Xantphos (6.11 g, 0.0106 mol) were added to a flask, and dissolved in tetrahydrofuran, and then refluxed for 24 hours. After completion of the reaction, the organic layer was extracted with ethyl acetate, and dried with magnesium sulfate. Next, it separated by column chromatography to obtain compound A-3 (10.9 g, yield: 70%).

3. Synthesis of Compound A-4

Compound A-3 (8.5 g, 0.0286 mol) and pyridine-hydrochloride (49.6 g, 0.429 mol) were added to a flask and refluxed at 200° C. for 2 hours. After completion of the reaction, ethyl acetate was added to the mixture and dissolved, and then neutralized with aqueous calcium carbonate solution. Thereafter, the organic layer was extracted, and dried with magnesium sulfate. Next, it separated by column chromatography to obtain compound A-4 (5.5 g, yield: 67.9%).

4. Synthesis of Compound A-5

Compound A-4 (5.5 g, 0.0194 mol) and potassium carbonate (1.34 g, 0.00971 mol) were added to a flask, and dissolved in 129 mL of dimethylformamide (DMF), and then heated at 150° C. for 2 hours. After completion of the reaction, the organic layer was extracted with ethyl acetate, and dried with magnesium sulfate. Next, it separated by column chromatography to obtain compound A-5 (4 g, yield: 78.3%).

5. Synthesis of Compound A-6

Compound A-5 (4 g, 0.0152 mol) and triphenylphosphine (PPh₃) (9.96 g, 0.038 mol) were added to a flask, and dissolved in 1,2-dichlorobenzene (o-DCB), and then refluxed for 24 hours. After completion of the reaction, the solvent was removed by distillation, and dissolved in ethyl acetate. The organic layer was extracted, and dried with magnesium sulfate. Next, it separated by column chromatography to obtain compound A-6 (3.2 g, yield: 91.1%).

6. Synthesis of Compound C-1

Compound A-6 (3.2 g, 0.0138 mol), compound B (8.06 g, 0.0208 mol), tris(dibenzylideneacetone)dipalladium(0) (0.630 g, 0.000692 mol), S-phos (0.568 g, 0.00138 mol), and sodium tert-butoxide (3.99 g, 0.0415 mol) were added to a flask and dissolved in 70 mL of o-xylene, and then refluxed for 2 hours. After completion of the reaction, the organic layer was separated with ethyl acetate, and dried with magnesium sulfate. Next, it separated by column chromatography to obtain compound C-1 (3 g, yield: 40%),

|  | MW | M.P |
|---|---|---|
| Example 1 | 538.61 | 299° C. |

[Example 2] Synthesis of Compound C-3

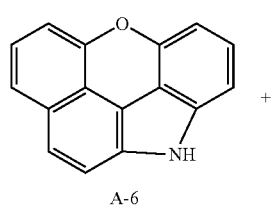

A-6

+

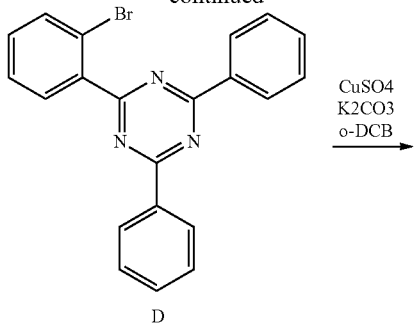

D

CuSO4
K2CO3
o-DCB
→

-continued

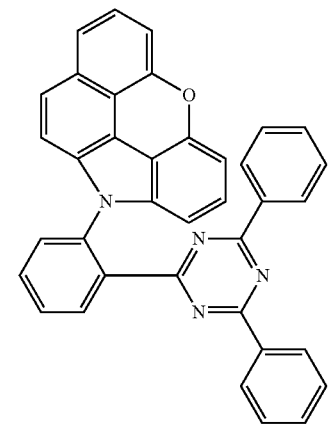

C-3

Compound A-6 (2.3 g, 0.00995 mol), compound D (3.86 g, 0.00995 mol), copper (II) sulfate (0794 g, 0.00497 mol), and potassium carbonate (2.75 g, 0.0199 mol) were added to a flask, and dissolved in 66.3 mL of o-dichlorobenzene, and then refluxed for 24 hours. After completion of the reaction, the solvent was removed by distillation, and dissolved in ethyl acetate. The organic layer was separated, and dried with magnesium sulfate. Next, it separated by column chromatography to obtain compound C-3 (2.2 g, yield: 41.1%).

|  | MW | Tg | M.P |
|---|---|---|---|
| Example 2 | 538.61 | 82.57 | 200.3 |

Hereinafter, the luminescent properties of an organic electroluminescent device comprising an organic electroluminescent compound of the present disclosure will be explained in order to understand the present disclosure in detail.

[Device Examples 1 and 2] Preparation of OLEDs Comprising the Host Compound According to the Present Disclosure OLEDs according to the present disclosure were produced. First, a transparent electrode indium tin oxide (ITO) thin film (10 Ω/sq) on a glass substrate for an OLED (GEOMATEC CO., LTD., Japan) was subjected to an ultrasonic washing with acetone and isopropanol, sequentially, and thereafter was stored in isopropanol and then used. Next, the ITO substrate was mounted on a substrate holder of a vacuum vapor deposition apparatus. Compound HI-1 was introduced into a cell of the vacuum vapor deposition apparatus, and compound HT-1 was then introduced into another cell of the vacuum vapor deposition apparatus. The two materials were evaporated at different rates and was deposited in a doping amount of 3 wt %, respectively, to form a hole injection layer having a thickness of 10 nm on the ITO substrate. Next, compound HT-1 was introduced into a cell of the vacuum vapor deposition apparatus and was evaporated by applying an electric current to the cell, thereby forming a first hole transport layer having a thickness of 80 nm on the first hole injection layer. Next, compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: The compound shown in the following Table 1 was introduced into a cell of the vacuum vapor deposition apparatus as a host, and compound D-39 was introduced into another cell as a dopant. The two materials were evaporated at different rates, and was deposited in a doping amount of 3 wt %, respectively, to form a light-emitting layer having a thickness of 40 nm on the hole transport layer. Next, compound ET-1 and compound EI-1 in another two cells were deposited at a rate of 1:1 to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, OLEDs were produced.

[Comparative Example 1] Preparation of OLED Comprising the Conventional Host Compound An OLED was produced in the same manner as in Device Example 1, except that compound CBP was used as the host of the light-emitting layer.

The driving voltage, the luminous efficiency, and the light-emitting color at a luminance of 1,000 nits, of the organic electroluminescent device according to Device Examples 1 and 2 and Comparative Example 1 produced as described above, were measured, and the results thereof are shown in the following Table 1.

TABLE 1

|  | Host | Driving Voltage (V) | Luminous Efficiency (cd/A) | Light-Emitting Color |
|---|---|---|---|---|
| Comparative Example 1 | CBP | 9.0 | 14.3 | Red |
| Device Examples 1 | C-1 | 3.2 | 28.9 | Red |
| Device Examples 2 | C-3 | 3.9 | 34.3 | Red |

From the results of the properties of the devices of Device Examples 1 and 2, and Comparative Example 1 above, it can be confirmed that by using the organic electroluminescent compound according to the present disclosure as a host compound, an organic electroluminescent device exhibits significantly low driving voltage and high luminous efficiency, compared to the organic electroluminescent device comprising a conventional host compound.

The compounds used in Device Examples and Comparative Example above are shown in the following Table 2.

TABLE 2

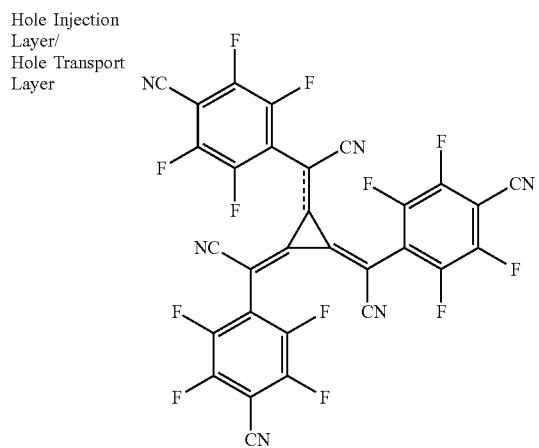

Hole Injection Layer/ Hole Transport Layer     HI-1

TABLE 2-continued
HT-1
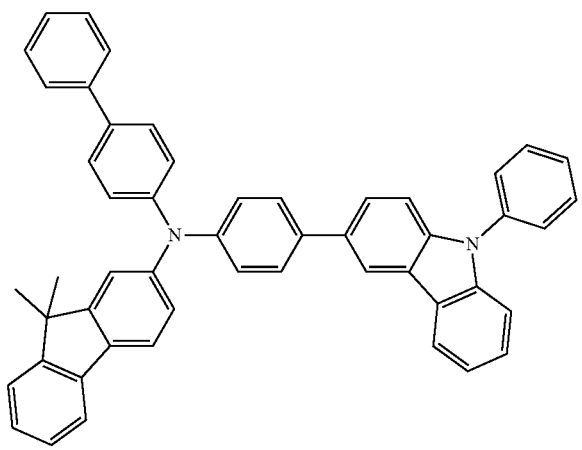
HT-2
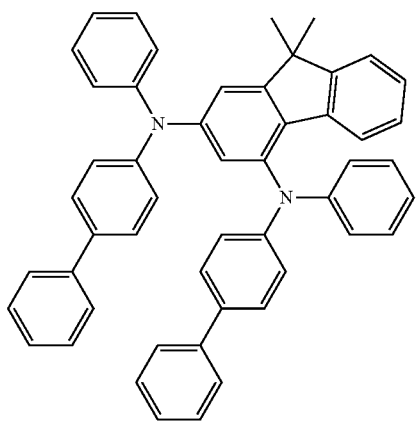
Light-Emitting Layer
CBP
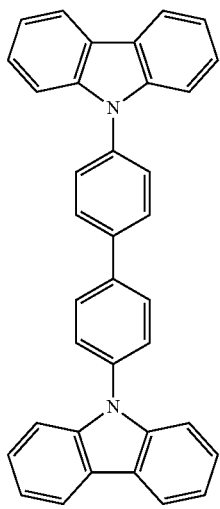

TABLE 2-continued
C-1
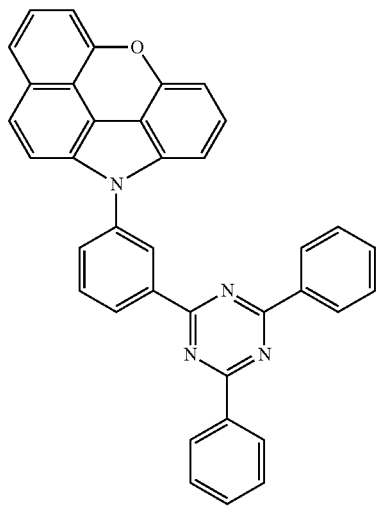
C-3
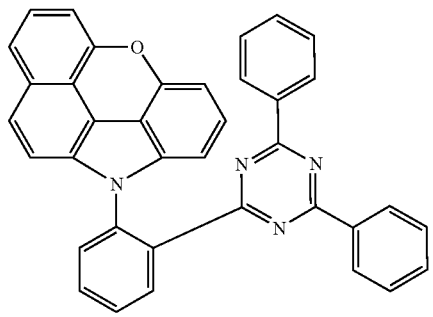
D-39
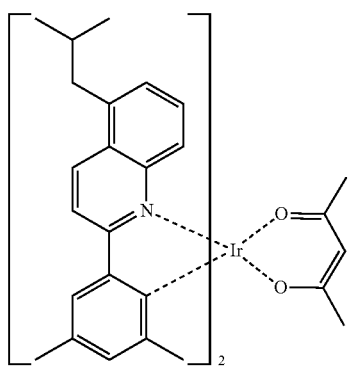
Electron
Transport
Layer/
Electron
Injection Layer
ET-1
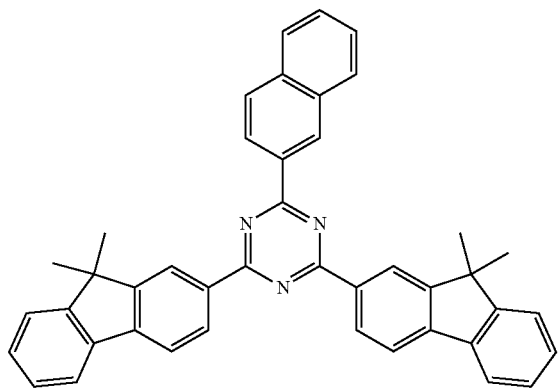

TABLE 2-continued

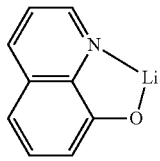

EI-1

The invention claimed is:

1. An organic electroluminescent compound represented by the following formula 1:

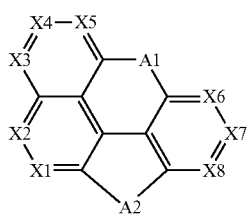

(1)

wherein the formula 1 is represented by any one of the following formulas 2-1 to 2-2:

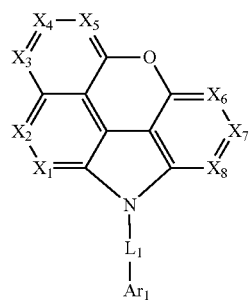

(2-1)

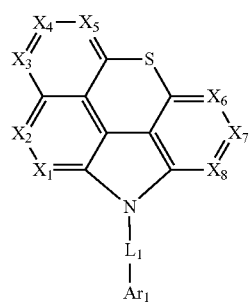

(2-2)

wherein $X_1$ to $X_8$ each independently represent, N or $CR_1$;

$L_1$ represents a single bond, a substituted or unsubstituted (C6-C30)arylene, or a substituted or unsubstituted (3- to 30-membered)heteroarylene;

$Ar_1$ and $R_1$ each independently represent, hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30) alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and an (C6-C30) aromatic ring, or -$L_a$-N—($Ar_a$)($Ar_b$); or may be linked to the adjacent substituent to form a ring(s);

$L_a$ represents a single bond, a substituted or unsubstituted (C6-C30)arylene, or a substituted or unsubstituted (3- to 30-membered)heteroarylene; and $Ar_a$ and $Ar_b$ each independently represent, hydrogen, a substituted or unsubstituted (C1-C30)alkyl, a substituted or unsubstituted (C2-C30)alkenyl, a substituted or unsubstituted fused ring of (C3-C30) aliphatic ring and an (C6-C30) aromatic ring, a substituted or unsubstituted (C6-C30)aryl, or a substituted or unsubstituted (3- to 30-membered)heteroaryl.

2. The organic electroluminescent compound according to claim 1, wherein $L_1$ represents a single bond, a substituted or unsubstituted (C6-C30)arylene, or a substituted or unsubstituted (5- to 30-membered)heteroarylene;

$Ar_1$ represents a substituted or unsubstituted (C6-C30) aryl, a substituted or unsubstituted (5- to 30-membered) heteroaryl, a substituted or unsubstituted fused ring of (C5-C18) aliphatic ring and an (C6-C18) aromatic ring, or -$L_a$-N—($Ar_a$)($Ar_b$);

$L_a$ represents a single bond or a substituted or unsubstituted (C6-C30)arylene; and $Ar_a$ and $Ar_b$ each independently represent, a substituted or unsubstituted (C6-C30)aryl or a substituted or unsubstituted (5- to 30-membered)heteroaryl.

3. The organic electroluminescent compound according to claim 1, wherein a substituent of the substituted (C1-C30) alkyl, the substituted (C2-C30)alkenyl, the substituted (C6-C30)aryl(ene), the substituted (3- to 30-membered)heteroaryl(ene), the substituted (C3-C30)cycloalkyl, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, and the substituted fused ring of (C3-C30) aliphatic ring and (C6-C30) aromatic ring, each independently represents, at least one selected from the group consisting of deuterium, halogen, cyano, carboxyl, nitro, hydroxy, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered)heterocycloalkyl, (C6-C30)aryloxy, (C6-C30)arylthio, (5- to 30-membered)heteroaryl unsubstituted or substituted with (C6-C30)aryl, (C6-C30)aryl unsubstituted or substituted with (5- to 30-membered)heteroaryl, tri(C1-C30)alkylsilyl, tri(C6-C30)arylsilyl, di(C1-C30)alkyl(C6-C30)arylsilyl, (C1-C30)alkyldi(C6-C30)arylsilyl, a fused ring of an (C3-C30) aliphatic ring and an (C6-C30) aromatic ring, amino, mono- or di-(C1-C30)alkylamino, mono- or di-(C2-C30)alkenylamino, (C1-C30)alkyl(C2-C30)alkenylamino, a substituted or unsubstituted mono- or di-(C6-C30)arylamino, (C1-C30)alkyl(C6-C30)arylamino, mono- or di-(3- to 30-membered)heteroarylamino, (C1-C30)alkyl (3- to 30-membered)heteroarylamino, (C2-C30)alkenyl(C6-C30)arylamino, (C2-C30)alkenyl(3- to 30-membered)heteroarylamino, (C6-C30)aryl(3- to 30-membered)heteroarylamino, (C1-C30)alkylcarbonyl, (C1-C30)alkoxycarbonyl, (C6-C30)arylcarbonyl, di(C6-C30)arylboronyl, di(C1-C30)alkylboronyl, (C1-C30)alkyl(C6-C30)arylboronyl, (C6-C30)ar(C1-C30)alkyl, and (C1-C30)alkyl(C6-C30)aryl.

4. The organic electroluminescent compound according to claim 1, wherein the compounds represented by the formula 2-1 and 2-2 are selected from the following compounds:

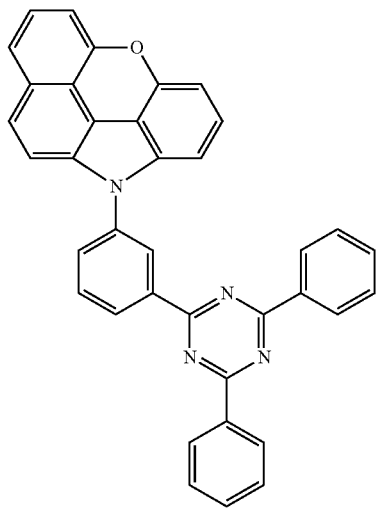
C-1

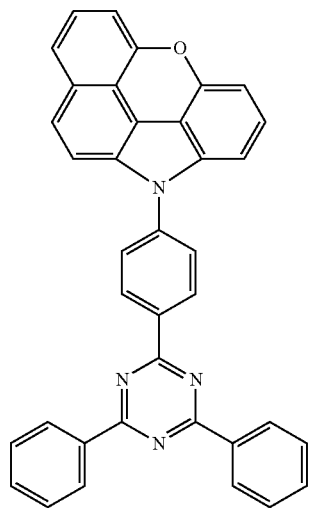
C-2

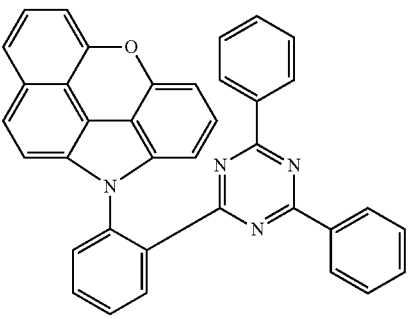
C-3

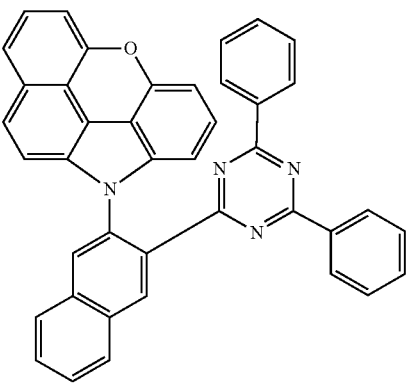
C-4

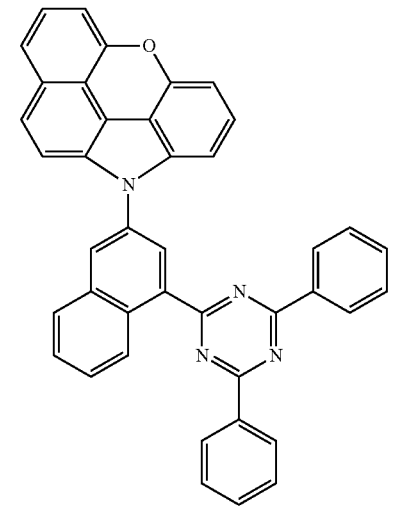
C-5

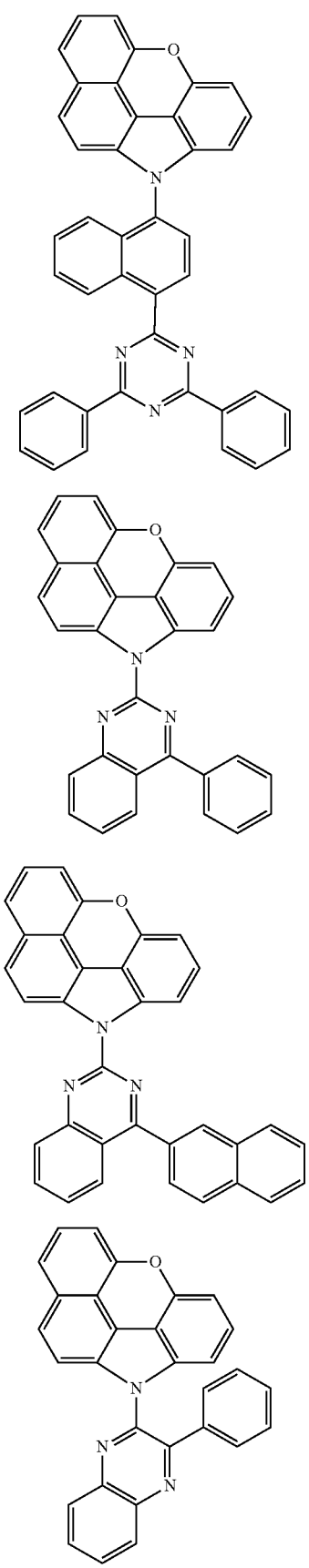
C-6
C-7
C-8
C-9
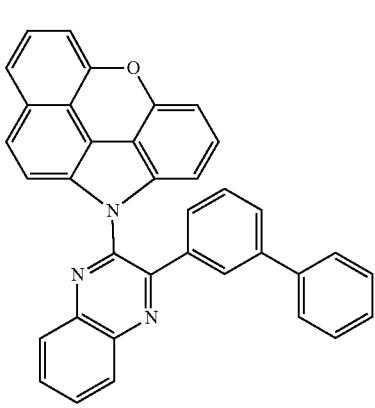
C-10
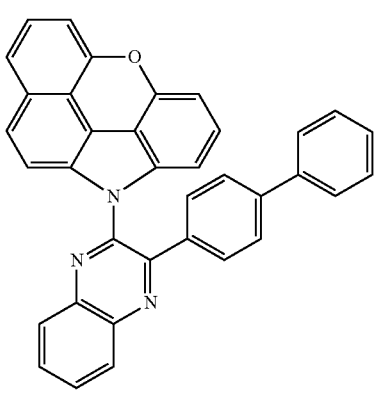
C-11
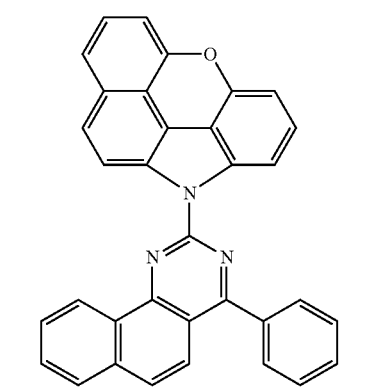
C-12
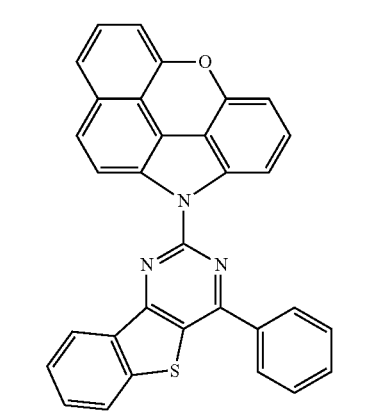
C-13

-continued
C-14
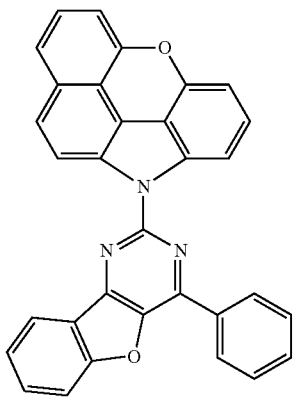
C-15
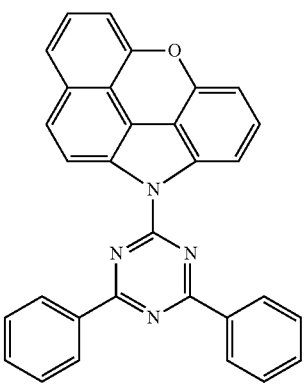
C-16
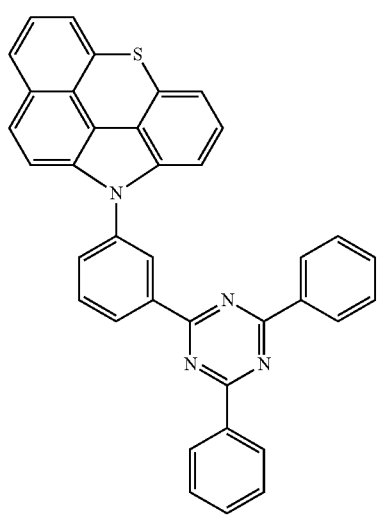
-continued
C-17
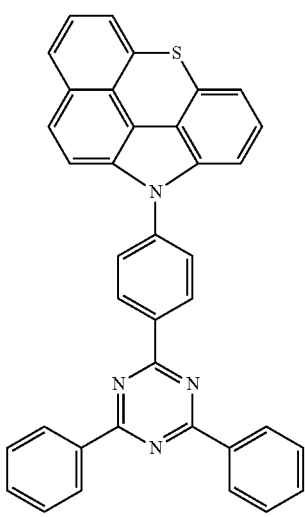
C-18
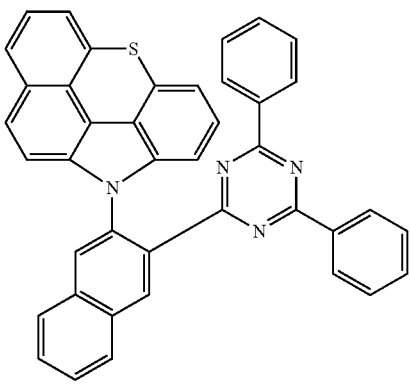
C-19

C-20
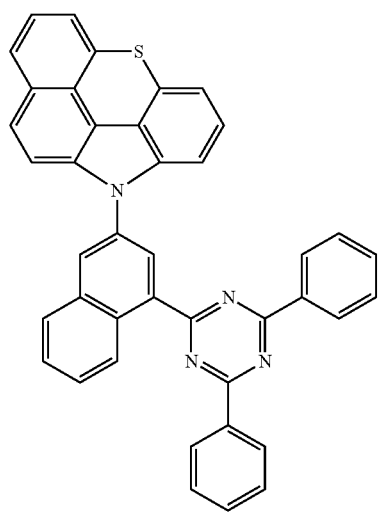
C-21
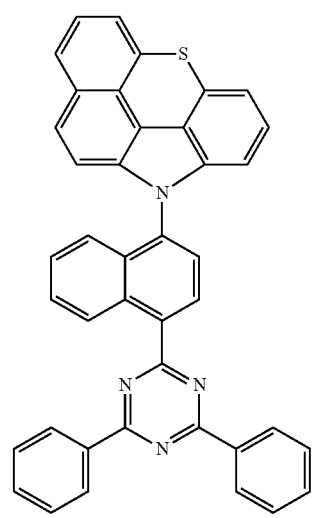
C-22
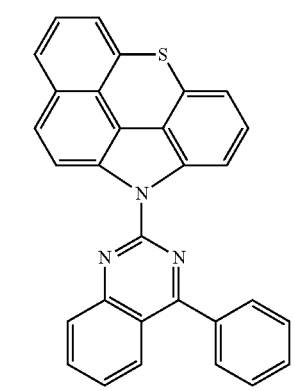
C-23
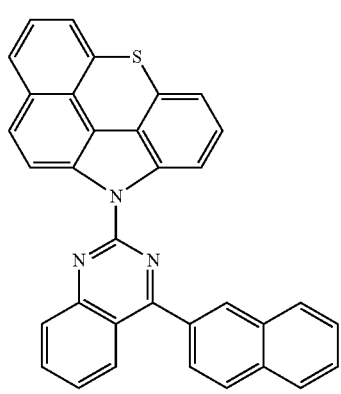
C-24
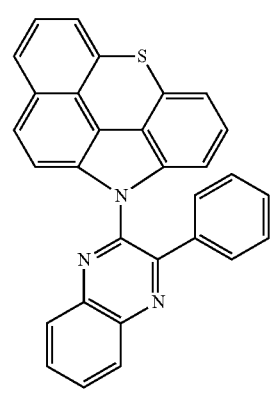
C-25
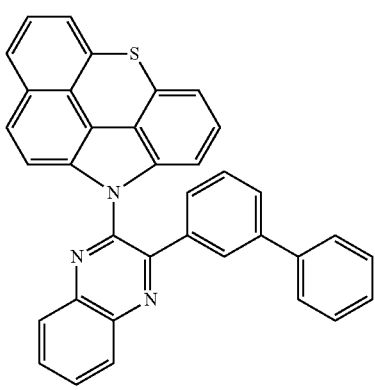
C-26
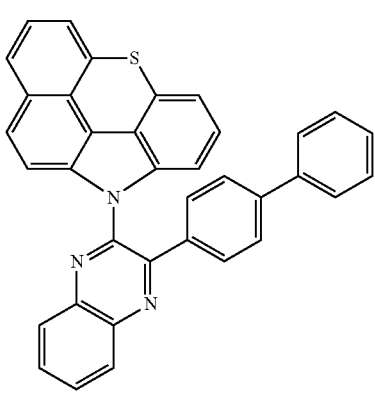

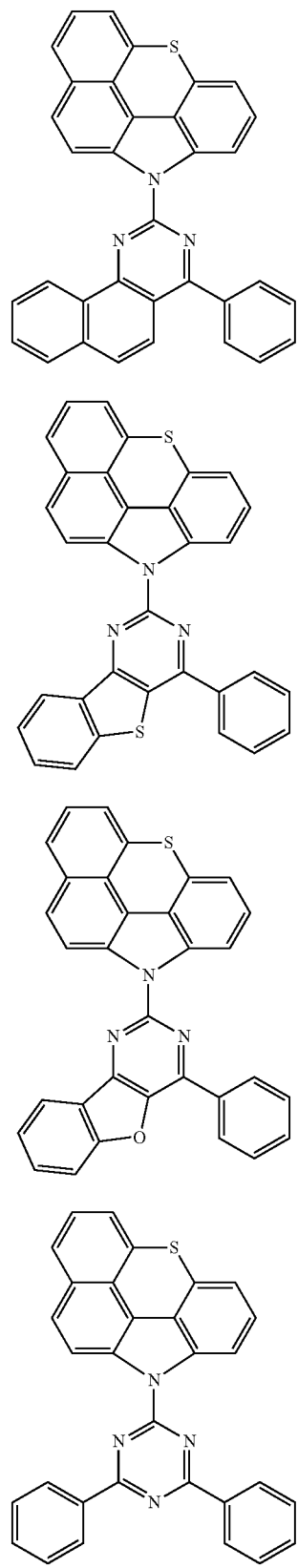
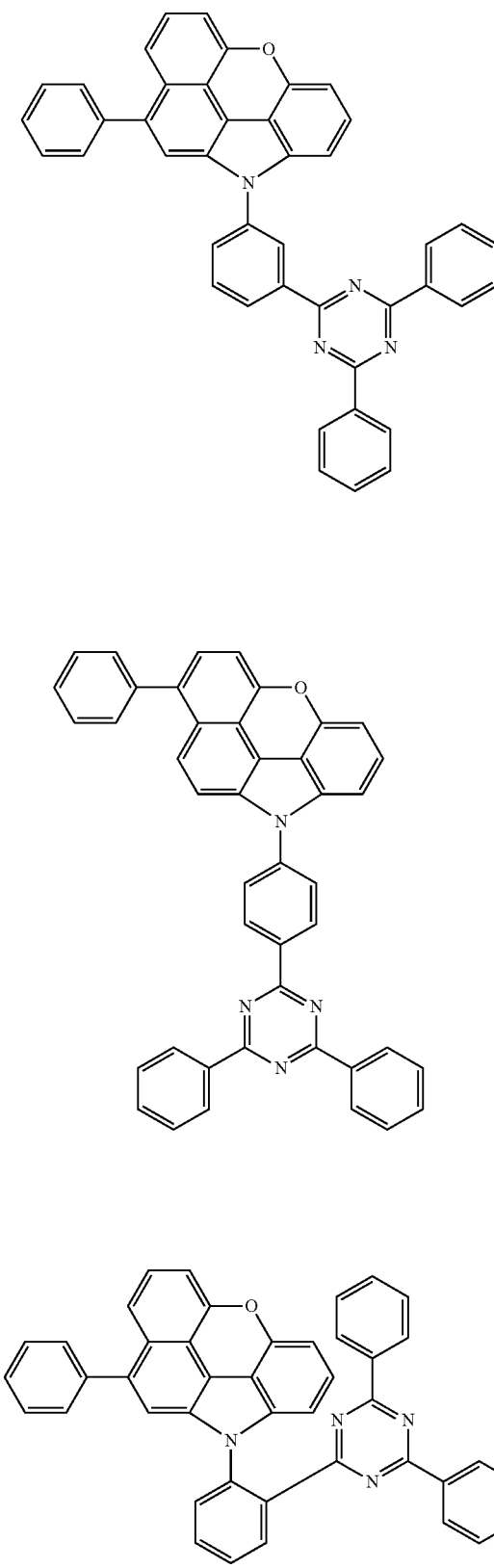

-continued
C-119
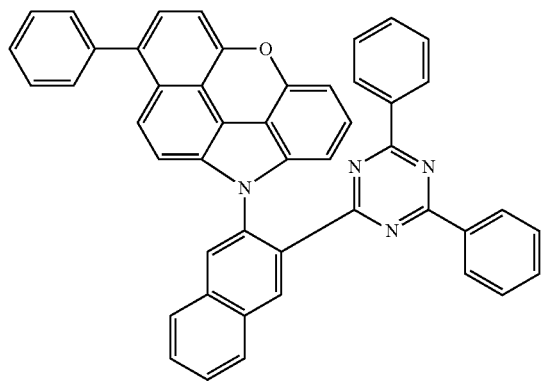
C-120
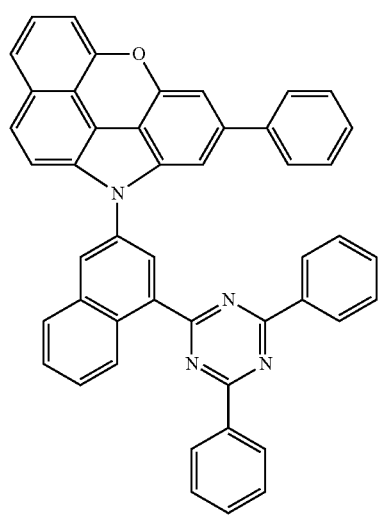
C-121
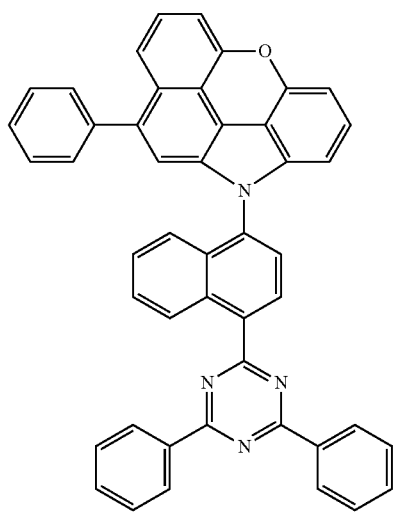
-continued
C-122
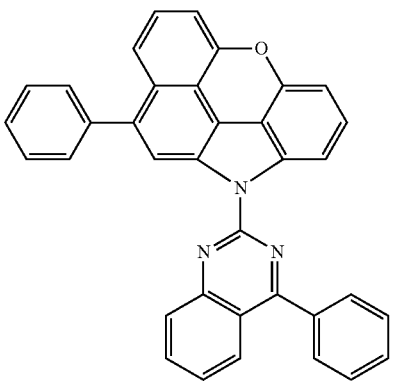
C-123
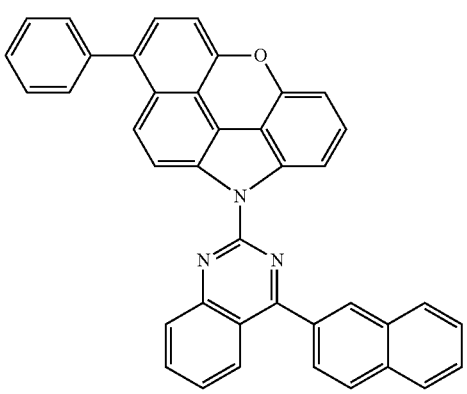
C-124
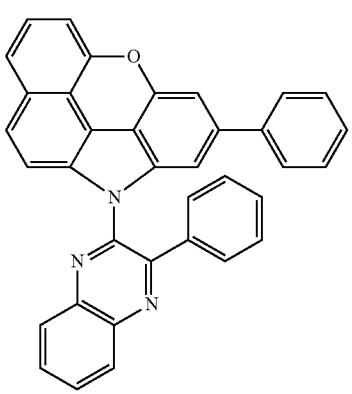
C-125
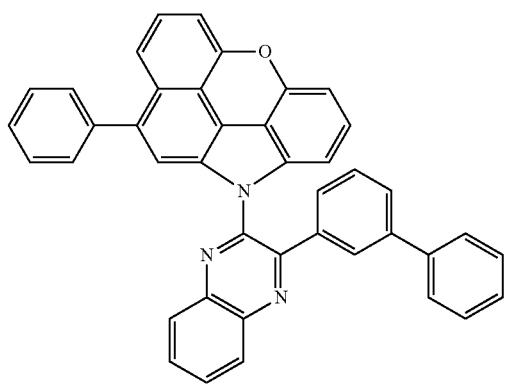

C-126
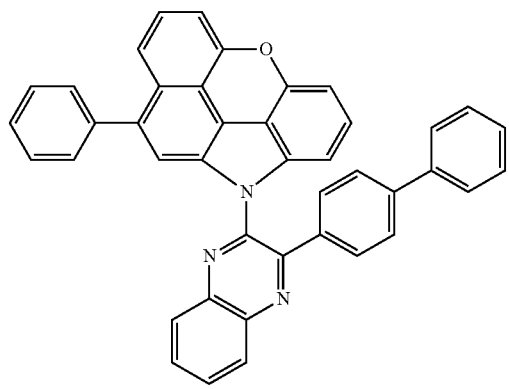
C-127
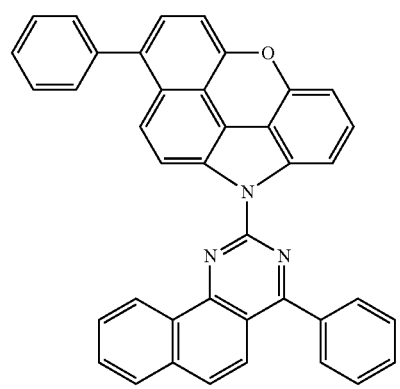
C-128
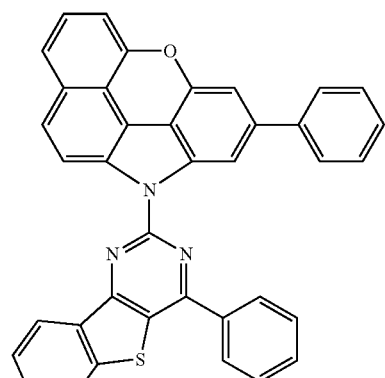
C-129
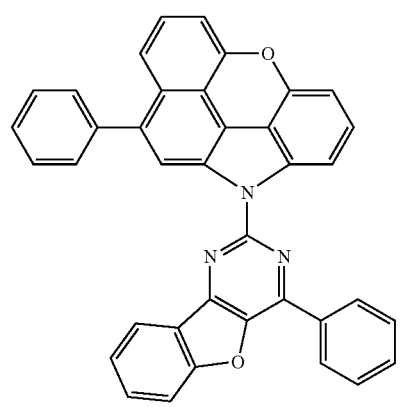
C-130
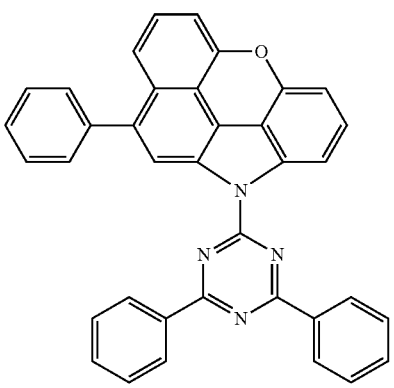
C-131
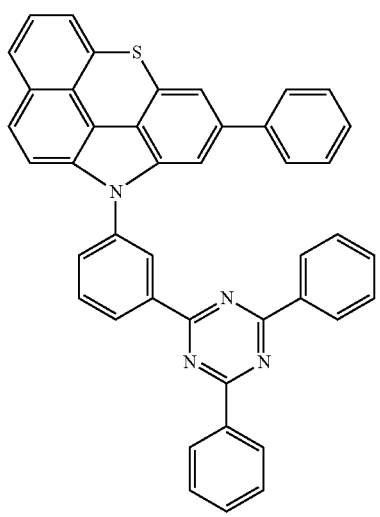
C-132
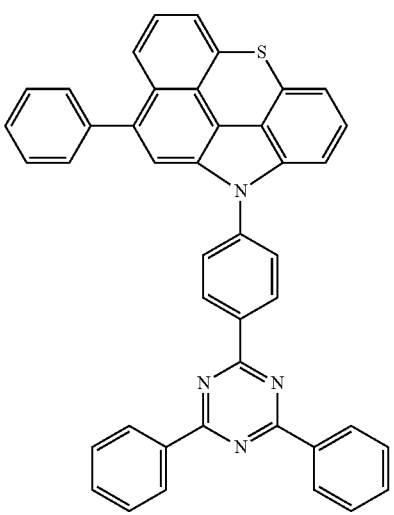

-continued
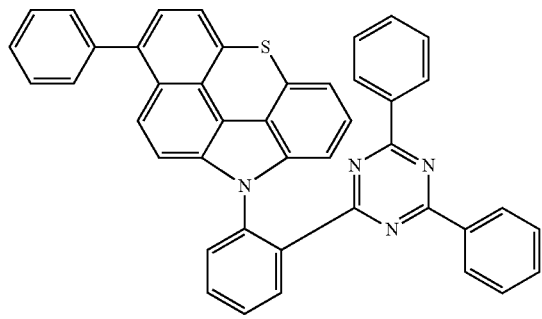
C-133
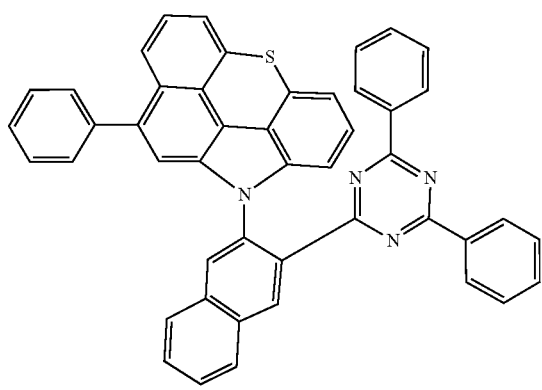
C-134
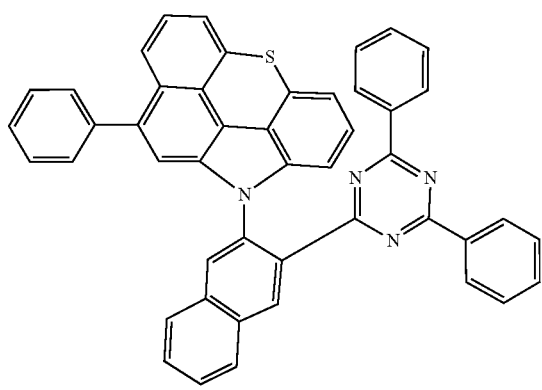
C-135
-continued
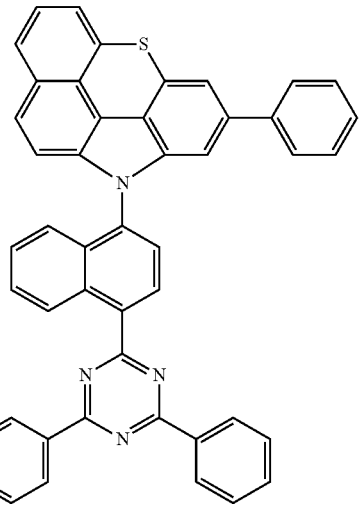
C-136
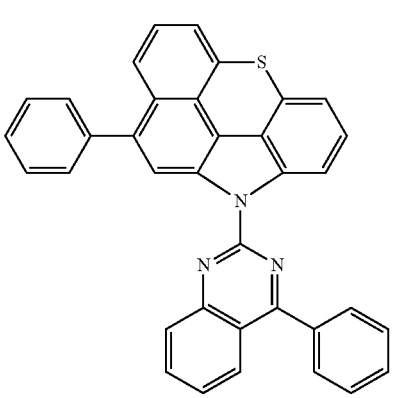
C-137
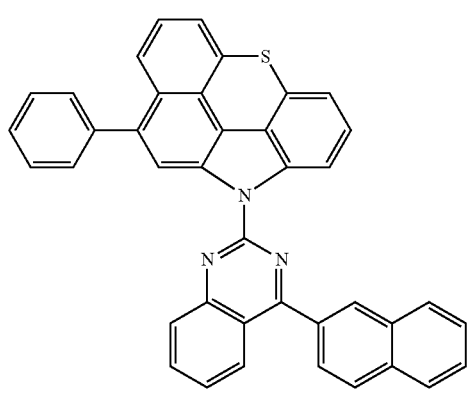
C-138
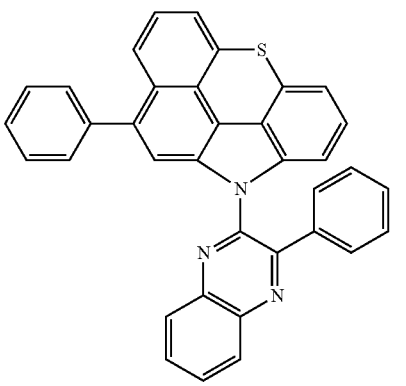
C-139

-continued
C-140
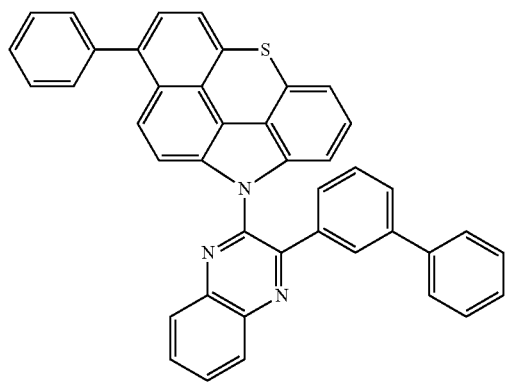
C-141
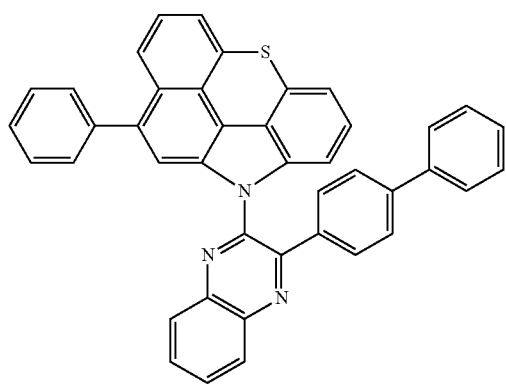
C-142
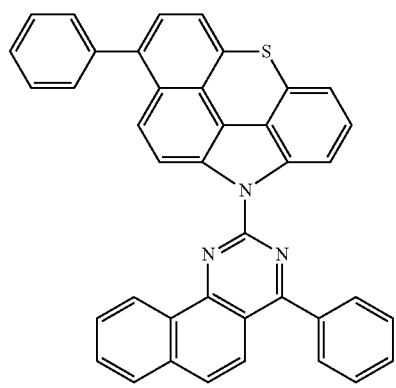
C-143
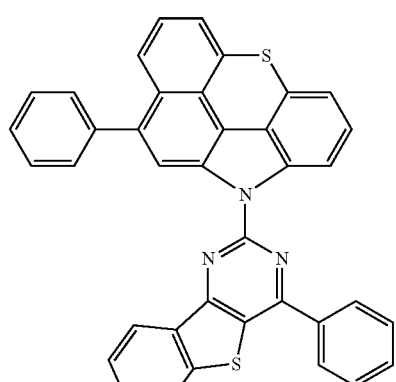
C-144
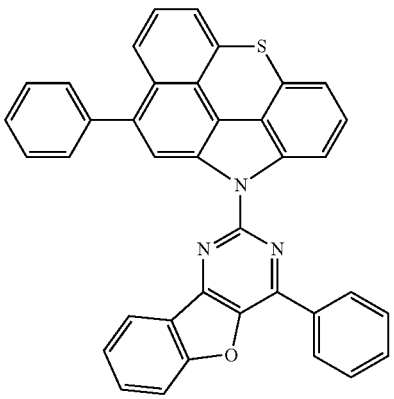
C-145
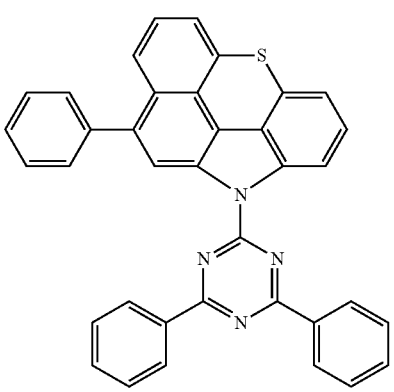
C-146
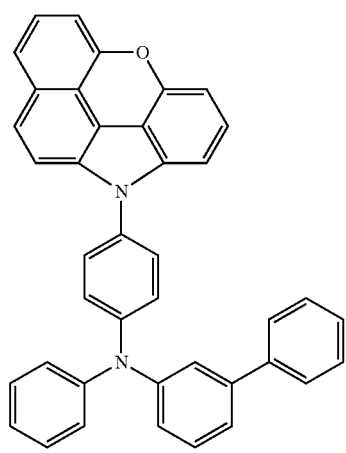

C-147
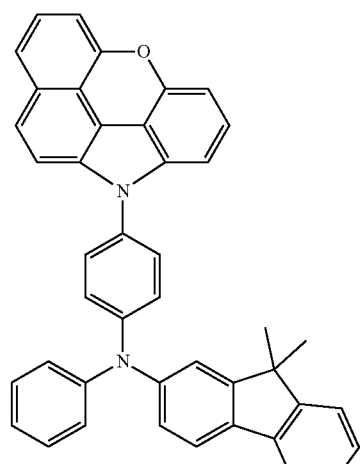
C-148
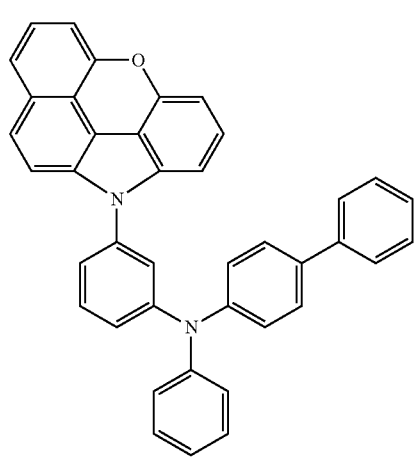
C-149
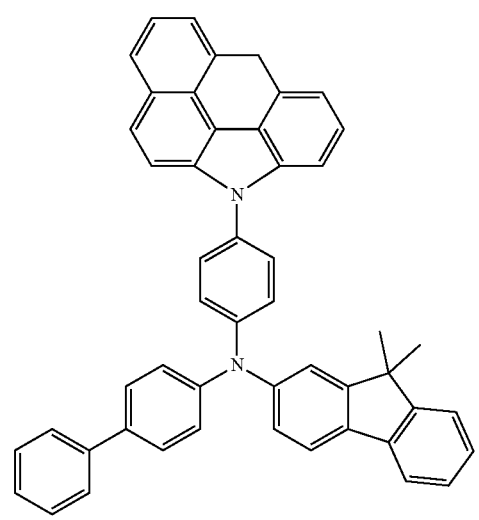
C-150
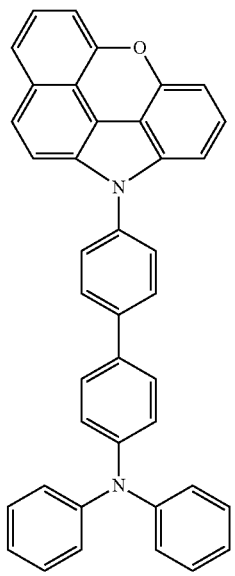
C-151
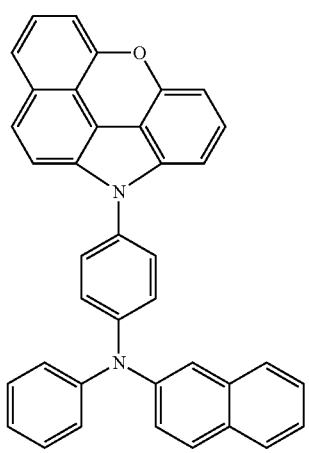
C-152
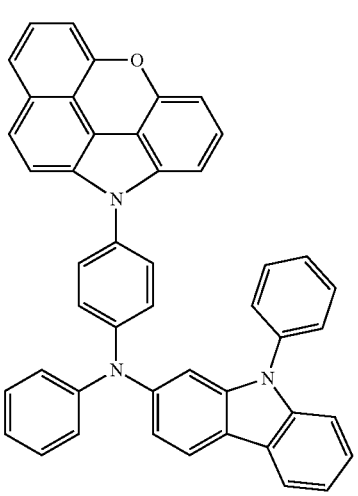

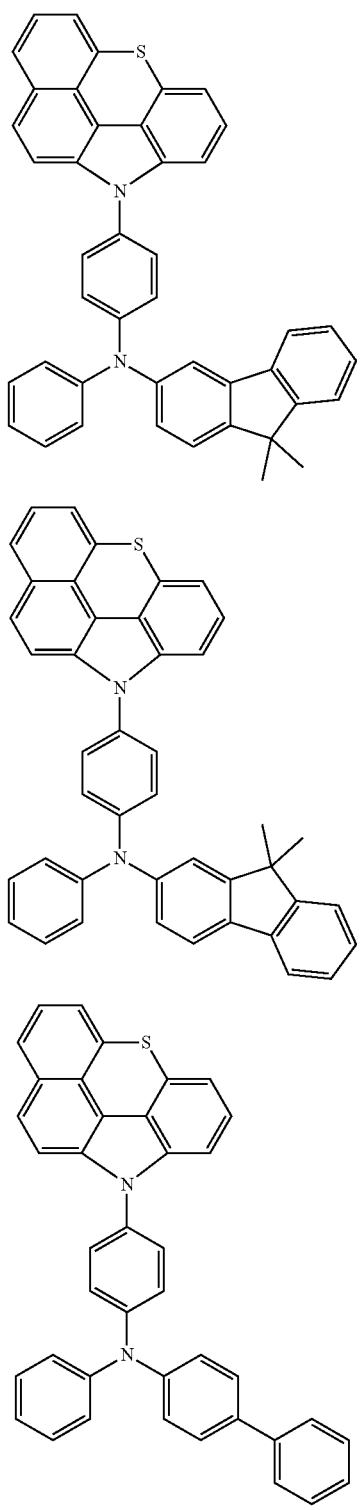
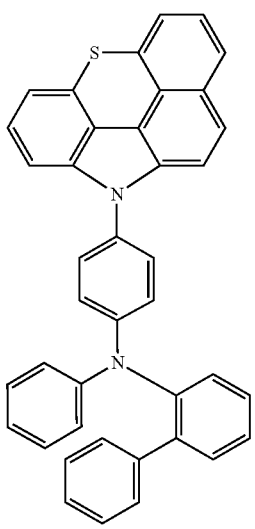
and
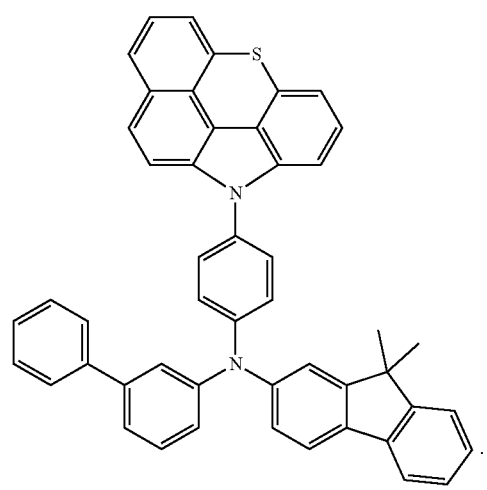
5. An organic electroluminescent device comprising the organic electroluminescent compound according to claim 1.
6. The organic electroluminescent device according to claim 5, wherein the organic electroluminescent compound is contained in a light-emitting layer.
* * * * *